US010022436B2

(12) United States Patent
Henderson

(10) Patent No.: US 10,022,436 B2
(45) Date of Patent: Jul. 17, 2018

(54) MICRONEEDLE COMPOSITIONS AND METHODS OF USING SAME

(71) Applicant: Verndari, Inc., Sacramento, CA (US)

(72) Inventor: Daniel R. Henderson, Sacramento, CA (US)

(73) Assignee: VERNDARI, INC., Sacramento, CA (US)

( * ) Notice: Subject to any disclaimer, the term of this patent is extended or adjusted under 35 U.S.C. 154(b) by 0 days.

(21) Appl. No.: 15/403,989

(22) Filed: Jan. 11, 2017

(65) Prior Publication Data

US 2017/0196966 A1 Jul. 13, 2017

Related U.S. Application Data

(60) Provisional application No. 62/277,312, filed on Jan. 11, 2016.

(51) Int. Cl.
| | |
|---|---|
| A61K 39/145 | (2006.01) |
| C12N 7/00 | (2006.01) |
| A61K 48/00 | (2006.01) |
| A61K 9/00 | (2006.01) |
| A61K 39/00 | (2006.01) |

(52) U.S. Cl.
CPC .......... *A61K 39/145* (2013.01); *A61K 9/0021* (2013.01); *A61K 48/005* (2013.01); *C12N 7/00* (2013.01); *A61K 2039/53* (2013.01); *A61K 2039/645* (2013.01); *C12N 2760/16134* (2013.01); *C12N 2760/16234* (2013.01); *C12N 2770/36143* (2013.01)

(58) Field of Classification Search
None
See application file for complete search history.

(56) References Cited

U.S. PATENT DOCUMENTS

| | | | |
|---|---|---|---|
| 5,762,939 A | 6/1998 | Smith et al. | |
| 5,858,368 A | 1/1999 | Smith et al. | |
| 5,976,552 A | 11/1999 | Volvovitz | |
| 6,015,686 A | 1/2000 | Dubensky, Jr. et al. | |
| 6,103,526 A | 8/2000 | Smith et al. | |
| 6,133,029 A | 10/2000 | Gruber et al. | |
| 6,242,259 B1 | 6/2001 | Polo et al. | |
| 6,245,532 B1 | 6/2001 | Smith et al. | |
| 6,329,201 B1 | 12/2001 | Polo et al. | |
| 6,334,856 B1 | 1/2002 | Allen et al. | |
| 6,451,592 B1 | 9/2002 | Dubensky, Jr. et al. | |
| 6,485,729 B1 | 11/2002 | Smith et al. | |
| 6,503,231 B1 | 1/2003 | Prausnitz et al. | |
| 6,611,707 B1 | 8/2003 | Prausnitz et al. | |
| 6,951,649 B2 | 10/2005 | Smith et al. | |
| 6,982,087 B2 | 1/2006 | Johnston et al. | |
| 7,182,747 B2 | 2/2007 | Kwon | |
| 7,226,439 B2 | 6/2007 | Prausnitz et al. | |
| 7,419,674 B2 | 9/2008 | Chulay et al. | |
| 7,744,900 B2 | 6/2010 | Dubensky, Jr. et al. | |
| 7,763,589 B2 | 7/2010 | Sallberg et al. | |
| 7,771,979 B2 | 8/2010 | Polo et al. | |
| 8,460,913 B2 | 6/2013 | Kamrud et al. | |
| 8,647,864 B2 | 2/2014 | Polo et al. | |
| 9,255,126 B2 | 2/2016 | Polo et al. | |
| 9,302,903 B2 | 4/2016 | Park et al. | |
| 9,364,426 B2 | 6/2016 | Gill et al. | |
| 9,517,205 B2 | 12/2016 | O'Hagan et al. | |
| 9,801,935 B2 | 10/2017 | O'Hagan et al. | |
| 2002/0071848 A1 | 6/2002 | Smith et al. | |
| 2003/0148262 A1* | 8/2003 | Polo ..................... | C07K 14/005 435/5 |
| 2003/0232058 A1 | 12/2003 | Dubensky et al. | |
| 2004/0022681 A1 | 2/2004 | Hantschel et al. | |
| 2004/0115167 A1 | 6/2004 | Cormier et al. | |
| 2004/0141984 A1 | 7/2004 | Bachmann et al. | |
| 2006/0280644 A1 | 12/2006 | Sellers et al. | |
| 2008/0125743 A1 | 5/2008 | Yuzhakov | |
| 2009/0246215 A1 | 10/2009 | Bachmann et al. | |
| 2010/0027174 A1 | 2/2010 | Galy et al. | |
| 2010/0152701 A1 | 6/2010 | McAllister et al. | |

(Continued)

FOREIGN PATENT DOCUMENTS

| | | |
|---|---|---|
| EP | 1171617 A2 | 1/2002 |
| EP | 1383556 A1 | 1/2004 |

(Continued)

OTHER PUBLICATIONS

Zimmer, Review RNA Replicons—A New Approach for Influenza Virus Immunoprophylaxis, 2010, vol. 2, pp. 413-434.*
Bachy, V. et al. Langerin negative dendritic cells promote potent CD8+ T-cell priming by skin delivery of live adenovirusvaccine microneedle arrays. Proc Natl Acad Sci U S A. Feb. 19, 2013;110(8):3041-6.
Chahal, J.S. et al. Dendrimer-RNA nanoparticles generate protective immunity against lethal Ebola, H1N1 influenza, and Toxoplasma gondii challenges with a single dose. Proc Natl Acad Sci U S A. Jul. 19, 2016;113(29):E4133-42.
Chong, R.H., et al. Gene silencing following siRNA delivery to skin via coated steel microneedles: In vitro and in vivo proof-of-concept. J Control Release. Mar. 28, 2013;166(3):211-9.
Geall, A.J., et al. Nonviral delivery of self-amplifying RNA vaccines. Proc Natl Acad Sci U S A. Sep. 4, 2012;109(36):14604-9.

(Continued)

*Primary Examiner* — Benjamin P Blumel
(74) *Attorney, Agent, or Firm* — Wilson Sonsini Goodrich & Rosati

(57) ABSTRACT

Described herein, are microneedle devices comprising a recombinant alphavirus replicon encoding an exogenous polypeptide, wherein the recombinant alphavirus replicon is coated onto or embedded into a plurality of microneedles. Also described herein are methods of preparing a microneedle device comprising a recombinant alphavirus replicon encoding an exogenous polypeptide. Also disclosed herein are methods of inducing an immune response in an individual comprising contacting the individual with a microneedle device comprising a recombinant alphavirus replicon encoding an exogenous polypeptide.

27 Claims, 19 Drawing Sheets

(56) References Cited

U.S. PATENT DOCUMENTS

| | | |
|---|---|---|
| 2010/0285135 A1 | 11/2010 | Wendorf et al. |
| 2010/0330121 A1 | 12/2010 | Dubensky, Jr. et al. |
| 2011/0002958 A1 | 1/2011 | Perri et al. |
| 2011/0064767 A1 | 3/2011 | Leberre et al. |
| 2011/0200582 A1 | 8/2011 | Baryza et al. |
| 2011/0300205 A1 | 12/2011 | Geall et al. |
| 2012/0016309 A1 | 1/2012 | Binks et al. |
| 2013/0004427 A1 | 1/2013 | El-Sayed et al. |
| 2013/0149375 A1 | 6/2013 | Geall |
| 2013/0177639 A1 | 7/2013 | Geall et al. |
| 2013/0177640 A1 | 7/2013 | Geall et al. |
| 2013/0183355 A1 | 7/2013 | Jain et al. |
| 2013/0195968 A1 | 8/2013 | Geall et al. |
| 2013/0295043 A1 | 11/2013 | Kallen et al. |
| 2013/0315955 A1 | 11/2013 | Holtz et al. |
| 2014/0030292 A1 | 1/2014 | Franti et al. |
| 2014/0193484 A1 | 7/2014 | Bertholet et al. |
| 2014/0227346 A1 | 8/2014 | Geall et al. |
| 2014/0242152 A1 | 8/2014 | Geall et al. |
| 2014/0271829 A1 | 9/2014 | Lilja et al. |
| 2014/0303232 A1 | 10/2014 | Baryza et al. |
| 2014/0309277 A1 | 10/2014 | Baryza et al. |
| 2015/0024002 A1 | 1/2015 | Perri et al. |
| 2015/0038897 A1 | 2/2015 | Daddona et al. |
| 2015/0175975 A1 | 6/2015 | Nasar et al. |
| 2015/0202281 A1 | 7/2015 | Renner et al. |
| 2015/0299728 A1 | 10/2015 | Rayner et al. |
| 2016/0108372 A1 | 4/2016 | Tratschin et al. |
| 2016/0129105 A1 | 5/2016 | Von Der Mülbe et al. |

FOREIGN PATENT DOCUMENTS

| | | |
|---|---|---|
| EP | 1392341 A2 | 3/2004 |
| EP | 1604688 A1 | 12/2005 |
| EP | 2055312 A1 | 5/2009 |
| EP | 2332573 A1 | 6/2011 |
| EP | 2338510 A1 | 6/2011 |
| EP | 3047856 A1 | 7/2016 |
| EP | 3061826 A1 | 8/2016 |
| WO | WO-9748440 A1 | 12/1997 |
| WO | WO-9846262 A1 | 10/1998 |
| WO | WO-0061770 A2 | 10/2000 |
| WO | WO-02056907 A2 | 7/2002 |
| WO | WO-2004016282 A1 | 2/2004 |
| WO | WO-2006130826 A1 | 12/2006 |
| WO | WO-2006138719 A2 | 12/2006 |
| WO | WO-2007081430 A2 | 7/2007 |
| WO | WO-2012006369 A2 | 1/2012 |
| WO | WO-2012051211 A2 | 4/2012 |
| WO | WO-2013055905 A1 | 4/2013 |
| WO | WO-2013137831 A1 | 9/2013 |
| WO | WO-2014005959 A1 | 1/2014 |
| WO | WO-2014108515 A1 | 7/2014 |
| WO | WO-2015024667 A1 | 2/2015 |
| WO | WO-2015034924 A1 | 3/2015 |
| WO | WO-2015063112 A1 | 5/2015 |
| WO | WO-2015110656 A1 | 7/2015 |
| WO | WO-2015189205 A1 | 12/2015 |
| WO | WO-2016073410 A1 | 5/2016 |
| WO | WO-2016118725 A1 | 7/2016 |
| WO | WO-2016135675 A1 | 9/2016 |

OTHER PUBLICATIONS

Gonzalez-Gonzalez, E. et al. Silencing of reporter gene expression in skin using siRNAs and expression of plasmid DNA delivered by a soluble protrusion array device (PAD). Mol Ther. Sep. 2010;18(9):1667-74.

Haigh, O. et al. CXCL1 gene silencing in skin using liposome-encapsulated siRNA delivered by microprojection array. J Control Release. Nov. 28, 2014;194:148-56.

Lara, M.F., et al. Inhibition of CD44 gene expression in human skin models, using self-delivery short interfering RNA administered by dissolvable microneedle arrays. Hum Gene Ther. Aug. 2012;23(8):816-23.

Pearson, F.E. et al. Induction of CD8(+) T cell responses and protective efficacy following microneedle-mediated delivery of a live adenovirus-vectored malaria vaccine. Vaccine. Jun. 22, 2015;33(28):3248-55.

Sahin, U. et al. mRNA-based therapeutics—developing a new class of drugs. Nat Rev Drug Discov. Oct. 2014;13(10):759-80.

Ulmer, J.B., Geall, A.J., Recent innovations in mRNA vaccines. Curr Opin Immunol. Aug. 2016;41:18-22.

Zaric, M. et al. Microneedle-mediated delivery of viral vectored vaccines. Expert Opin Drug Deliv. Sep. 7, 2016:1-11.

Criscione, et al. Self-assembly of pH-resistant fluorinated dendrimer-based particulates for drug delivery and noninvasive imaging. Biomaterials 30(2009):3946-3955.

International Application No. PCT/US17/13043 International Search Report and Written Opinion dated Jun. 2, 2017.

Ameri M., et al.; Demonstrated Solid-State Stability of Parathyroid Hormone PTH(1-34) Coated on a Novel Transdermal Microprojection Delivery System; Pharmaceutical Research, vol. 26, No. 11, Nov. 2009.

Ameri M., et al.; Human Growth Hormone Delivery with a Microneedle Transdermal System: Preclinical Formulation, Stability, Delivery and PK of Therapeutically Relevant Doses; Pharmaceutics 2014, 6, 220-234.

Ameri M., et al.; Parathyroid Hormone PTH(1-34) Formulation that Enables Uniform Coating on a Novel Transdermal Microprojection Delivery System; Pharmaceutical Research, vol. 27, No. 2, Feb. 2010.

Bragazzi NL; Fluzone® intra-dermal (Intanza®/Istivac® Intradermal): An updated overview; Hum Vaccin Immunother. Oct. 2, 2016;12(10):2616-2627. doi: 10.1080/21645515.2016.1187343. Epub May 31, 2016.

Brazzoli M., et al.; Induction of Broad-Based Immunity and Protective Efficacy by Self-amplifying mRNA Vaccines Encoding Influenza Virus Hemagglutinin.; J Virol. Oct. 14, 2015;90(1):332-44.

Chu L., et al.; Enhanced Stability of Inactivated Influenza Vaccine Encapsulated in Dissolving Microneedle Patches; Pharm Res (2016) 33:868-878.

Edens C; A microneedle patch containing measles vaccine is immunogenic in non-human primates. Vaccine. Sep. 8, 2015;33(37):4712-8.

Edens C; Inactivated polio vaccination using a microneedle patch is immunogenic in the rhesus macaque. Vaccine. Sep. 8, 2015;33(37):4683-90.

International Application No. PCT/US2017045161 International Search Report dated Nov. 13, 2017.

Kalomiraki M., et al; Dendrimers as tunable vectors of drug delivery systems and biomedical and ocular applications. Int J Nanomedicine. Dec. 22, 2015;11:1-12.

Kim YC; Microneedle delivery of trivalent influenza vaccine to the skin induces long-term cross-protection. J Drug Target. Dec. 2016;24(10):943-951.

Koutsonanosa D., et al.; Enhanced immune responses by skin vaccination with influenzasubunit vaccine in young hosts; Vaccine. Sep. 8, 2015;33(37):4675-82.

Larraneta E; Microneedles: A New Frontier in Nanomedicine Delivery; Pharm Res. May 2016;33(5):1055-73.

Ljungberg K., Liljeström P.; Self-replicating alphavirus RNA vaccines.; Expert Rev Vaccines. Feb. 2015;14(2):177-94.

Magini D., et al.; Self-Amplifying mRNA Vaccines Expressing Multiple Conserved Influenza Antigens Confer Protection against Homologous and Heterosubtypic Viral Challenge.; PLoS One. Aug. 15, 2016;11(8):e0161193.

Marquez-Miranda et al.; Effect of Terminal Groups of Dendrimers in the Complexation with Antisense Oligonucleotides and Cell Uptake Nanoscale Research Letters (2016) 11:66.

Uddin J., Inkjet printing of transdermal microneedles for the delivery of anticancer agents; International Journal of Pharmaceutics 494 (2015) 593-602.

(56) References Cited

OTHER PUBLICATIONS

Vrdolijak A., Induction of broad immunity by thermostabilised vaccines incorporated in dissolvable microneedles using novel fabrication methods; Journal of Controlled Release 225 (2016) 192-204.

Wang Y; Skin Vaccination against Rotavirus Using Microneedles: Proof of Concept in Gnotobiotic Piglets. PLoS One. Nov. 8, 2016;11(11):e0166038.

Gill, H. S. et al. Coated microneedles for transdermal delivery. J. Control Release, 117(2):227-237 (Feb. 12, 2007).

Kim, Yeu-Chun, et al. Enhanced Memory Responses to Season H1N1 Influenza Vaccination of the Skin with the Use of Vaccine-Coated Microneedles. The Journal of Infectious Diseases 201:190-198 (Jan. 15, 2010).

\* cited by examiner

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
taatacgact cactataggg                                              20

MICRONEEDLE COMPOSITIONS AND METHODS OF USING SAME

CROSS REFERENCE TO RELATED APPLICATIONS

This application claims the benefit of U.S. Provisional Application No. 62/277,312, filed on Jan. 11, 2016, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Jan. 31, 2017, is named 47750701201_SL.txt and is 514 bytes in size.

BACKGROUND OF THE INVENTION

Delivery of compositions to a target cell or tissue faces various transport barriers. Nucleic acids that encode gene products, such as proteins, and non-coding RNA (e.g., siRNAs) can be delivered directly to a desired vertebrate subject, or can be delivered ex vivo to cells obtained or derived from the subject, and the cells can be re-implanted into the subject. Delivery of such nucleic acids to a vertebrate subject is desirable for many purposes, such as, for gene therapy, to induce an immune response against an encoded polypeptide, or to regulate the expression of endogenous genes. The use of this approach has been hindered because free DNA is not readily taken up by cells and free RNA is rapidly degraded in vivo. Moreover, delivery can also be problematic. For instance, subcutaneous or intramuscular injections using hypodermic needles can cause pain, trauma, and anxiety in a subject.

Delivery of one or more polypeptides, whether directly as protein or indirectly by an encoding polynucleotide, has many useful applications, including vaccination. Vaccination has proven an effective means to fight and even eradicate infectious diseases. The influenza vaccine, for example, is currently recommended by the CDC as the primary method for preventing influenza. However, influenza virus has a high rate of mutation and antigenic variation and a new vaccine is typically produced each year based upon the predicted circulating pathogenic strains. This poses a number of challenges. For instance, the effectiveness of the vaccine is only as good as the prediction. If the prediction of the dominant strain is incorrect, the vaccine will have limited effectiveness for most people. Further, it can take months to produce enough influenza vaccine to vaccinate a population.

SUMMARY OF THE INVENTION

Disclosed herein, in some embodiments, are microneedle devices for administering an RNA molecule, comprising: (a) a substrate comprising a plurality of microneedles; and (b) a composition comprising an RNA encoding an exogenous polypeptide coated onto or embedded into the plurality of microneedles. In some embodiments, the RNA molecule is a recombinant alphavirus replicon. In some embodiments, the RNA molecule is dehydrated. In some embodiments, the plurality of microneedles are dissolvable, biosoluble, or biodegradable. In some embodiments, the exogenous polypeptide is a foreign or a self-antigen. In some embodiments, the self-antigen is an antigen associated with a cancer. In some embodiments, the foreign antigen is an antigen associated with an infectious agent. In some embodiments, the recombinant alphavirus replicon is present in an amount effective to induce an immune response to the foreign or self-antigen. In some embodiments, the exogenous polypeptide is an influenza virus HA or NA polypeptide. In some embodiments, the influenza virus HA polypeptide is an influenza A virus HA polypeptide or an influenza B virus HA polypeptide. In some embodiments, the influenza virus HA polypeptide is from a viral strain of a group 1 influenza A virus subtype selected from H1, H2, H5, H6, H8, H9, H11, H12, H13, H16, H17, or H18. In some embodiments, the influenza virus HA polypeptide is from a viral strain of a group 2 influenza A virus subtype selected from H3, H4, H7, H10, H14, or H15. In some embodiments, the influenza virus HA polypeptide is from a viral strain of an influenza B virus. In some embodiments, the influenza virus HA polypeptide is from a viral strain of an influenza A virus H1 subtype. In some embodiments, the influenza virus HA polypeptide is from a viral strain of an influenza A virus H3 subtype. In some embodiments, the influenza virus HA polypeptide is from a viral strain of an influenza B virus Yamagata or Victoria lineage. In some embodiments, the recombinant alphavirus replicon encodes an exogenous polypeptide comprising: (a) an HA polypeptide from a viral strain of an influenza A virus H1 subtype; (b) an HA polypeptide from a viral strain of an influenza A virus H3 subtype; (c) an HA polypeptide from a viral strain of an influenza B virus Yamagata lineage; (d) an HA polypeptide from a viral strain of an influenza B virus Victoria lineage; or (e) any combinations thereof. In some embodiments, the recombinant alphavirus replicon encodes at least two exogenous polypeptides comprising: (a) an HA polypeptide from a viral strain of an influenza A virus H1 subtype; (b) an HA polypeptide from a viral strain of an influenza A virus H3 subtype; (c) an HA polypeptide from a viral strain of an influenza B virus Yamagata lineage; or (d) an HA polypeptide from a viral strain of an influenza B virus Victoria lineage. In some embodiments, each of the exogenous polypeptides are encoded on a single recombinant alphavirus replicon. In some embodiments, the exogenous polypeptides are encoded on different recombinant alphavirus replicons. In some embodiments, the exogenous polypeptide is a hepatitis B virus surface antigen (HBsAg). In some embodiments, the recombinant alphavirus replicon encodes an exogenous polypeptide comprising: (a) an antigen from a polio virus; (b) an antigen from *Clostridium tetani*; (c) an antigen from a rabies virus; or (d) any combinations thereof. In some embodiments, the recombinant alphavirus replicon encodes an exogenous polypeptide comprising: (a) an antigen from a polio virus; (b) an antigen from *Clostridium tetani*; and (c) an antigen from a rabies virus. In some embodiments, each of the exogenous polypeptides are encoded on a single recombinant alphavirus replicon. In some embodiments, the exogenous polypeptides are encoded on different recombinant alphavirus replicons. In some embodiments, the recombinant alphavirus replicon encodes an exogenous polypeptide comprising: (a) an antigen from a Marburg virus; (b) an antigen from an Ebola Sudan virus; (c) an antigen from an Ebola Zaire virus; or (d) any combinations thereof. In some embodiments, the recombinant alphavirus replicon encodes an exogenous polypeptide comprising: (a) an antigen from a Marburg virus; (b) an antigen from an Ebola Sudan virus; and (c) an antigen from an Ebola Zaire virus. In some embodiments, each of the exogenous polypeptides are encoded on a single recombinant alphavirus replicon. In some embodiments, the exogenous polypeptides are encoded on different recombinant alphavirus replicons. In some embodiments, the microneedle device is effective in inducing an immune response to the exogenous polypeptide after storage for at least one month at room temperature. In some embodiments, a second bioactive agent coated onto or embedded into the plurality of microneedles. In some embodiments, the second bioactive agent is a polypeptide. In some embodiments, the second bioactive agent enhances an immune response in an individual. In some embodiments, the second bioactive agent is an adjuvant. In some embodiments, the recombinant alphavirus replicon is formulated as a dendrimer-replicon nanoparticle. In some embodiments, the dendrimer is a PAMAM dendrimer. In some embodiments, the PAMAM dendrimer comprises amino surface reactive groups. In some embodiments, the PAMAM dendrimer is a G5 or G9 PAMAM dendrimer comprising amino surface reactive groups. In some embodiments, the PAMAM dendrimer comprises modified amino surface reactive groups. In some embodiments, the modified amino surface reactive groups are modified with a fluorinating agent, an N-hydroxysuccinimide ester, or an amino acid. In some embodiments, the N-hydroxysuccinimide ester is an N-hydroxysuccinimide ester of PEG or an N-hydroxysuccinimide ester of a cell penetrating peptide. In some embodiments, the fluorinating agent is heptafluoro butyric acid anhydride. In some embodiments, the amino acid is arginine or histidine. In some embodiments, the dendrimer-replicon nanoparticle is formulated by a microfluidic mixing device. In some embodiments, the recombinant alphavirus replicon is coated onto the plurality of microneedles using a microfluidic dispensing device.

Disclosed herein, in some embodiments, are microneedle devices for administering an RNA molecule, comprising: (a) a substrate comprising a plurality of microneedles; and (b) a pharmaceutical composition comprising a recombinant alphavirus replicon encoding an exogenous polypeptide and a pharmaceutically acceptable carrier or excipient coated onto or embedded into the plurality of microneedles.

Disclosed herein, in some embodiments, are methods of delivering a polypeptide to an individual in need thereof, comprising administering to the individual any one of the microneedle devices described herein. Also disclose herein, in some embodiments, are methods of preparing a microneedle device, comprising: (a) obtaining a substrate comprising a plurality of microneedles; and (b) coating or embedding a composition comprising an RNA molecule encoding an exogenous polypeptide onto or into the plurality of microneedles. In some embodiments, the RNA molecule is a recombinant alphavirus replicon. In some embodiments, the recombinant alphavirus replicon is dehydrated. In some embodiments, the recombinant alphavirus replicon is dehydrated prior to being coated onto or embedded into the plurality of microneedles. In some embodiments, the recombinant alphavirus replicon is dehydrated after being coated onto or embedded into the plurality of microneedles. In some embodiments, the plurality of individual microneedles are dissolvable, biosoluble, or biodegradable. In some embodiments, the recombinant alphavirus replicon is formulated as a dendrimer-replicon nanoparticle. In some embodiments, the dendrimer is a PAMAM dendrimer. In some embodiments, the PAMAM dendrimer comprises amino surface reactive groups. In some embodiments, the PAMAM dendrimer is a G5 or G9 PAMAM dendrimer comprising amino surface reactive groups. In some embodiments, the dendrimer-replicon nanoparticle is produced by a microfluidic mixing device. In some embodiments, the recombinant alphavirus replicon is coated onto the plurality of microneedles using a microfluidic dispensing device.

Also disclosed herein, in some embodiments, are methods of inducing an immune response in an individual in need thereof, comprising: (a) contacting the dermal surface of the individual with a microneedle device comprising (i) a plurality of microneedles comprising a recombinant alphavirus replicon encoding an exogenous polypeptide coated onto or embedded into the plurality of microneedles, and (b) delivering the recombinant alphavirus replicon to the individual, thereby inducing an immune response in the individual. In some embodiments, the recombinant alphavirus replicon is dehydrated. In some embodiments, the plurality of individual microneedles are dissolvable, biosoluble, or biodegradable. In some embodiments, the exogenous polypeptide is a foreign or a self-antigen. In some embodiments, the self-antigen is an antigen associated with a cancer. In some embodiments, the foreign antigen is an antigen associated with an infectious agent. In some embodiments, the recombinant alphavirus replicon is present in an amount effective to alone induce an immune response to the foreign or self-antigen. In some embodiments, the exogenous polypeptide is an influenza virus HA or NA polypeptide. In some embodiments, the influenza virus HA polypeptide is an influenza A virus HA polypeptide or an influenza B virus HA polypeptide. In some embodiments, the influenza virus HA polypeptide is from a viral strain of a group 1 influenza A virus subtype selected from H1, H2, H5, H6, H8, H9, H11, H12, H13, H16, H17, or H18. In some embodiments, the influenza virus HA polypeptide is from a viral strain of a group 2 influenza A virus subtype selected from H3, H4, H7, H10, H14, or H15. In some embodiments, the influenza virus HA polypeptide is from a viral strain of an influenza B virus. In some embodiments, the influenza virus HA polypeptide is from a viral strain of an influenza A virus H1 subtype. In some embodiments, the influenza virus HA polypeptide is from a viral strain of an influenza A virus H3 subtype. In some embodiments, the influenza virus HA polypeptide is from a viral strain of an influenza B virus Yamagata or Victoria lineage. In some embodiments, the recombinant alphavirus replicon encodes an exogenous polypeptide selected from: (a) an HA polypeptide from a viral strain of an influenza A virus H1 subtype; (b) an HA polypeptide from a viral strain of an influenza A virus H3 subtype; (c) an HA polypeptide from a viral strain of an influenza B virus Yamagata lineage; (d) an HA polypeptide from a viral strain of an influenza B virus Victoria lineage; or (e) any combinations thereof. In some embodiments, the recombinant alphavirus replicon encodes at least two exogenous polypeptides selected from: (a) an HA polypeptide from a viral strain of an influenza A virus H1 subtype; (b) an HA polypeptide from a viral strain of an influenza A virus H3 subtype; (c) an HA polypeptide from a viral strain of an influenza B virus Yamagata lineage; or (d) an HA polypeptide from a viral strain of an influenza B virus Victoria lineage. In some embodiments, each of the exogenous polypeptides are encoded on a single recombinant alphavirus replicon. In some embodiments, the exogenous polypeptides are encoded on different recombinant alphavirus replicons. In some embodiments, the exogenous polypeptide is a hepatitis B virus surface antigen (HBsAg). In some embodiments, the recombinant alphavirus replicon is formulated as a dendrimer-replicon nanoparticle. In some embodiments, the dendrimer is a PAMAM dendrimer. In some embodiments, the PAMAM dendrimer comprises amino surface reactive groups. In some embodiments, the dendrimer is a G5 or G9 PAMAM dendrimer comprising amino surface reactive groups. In some embodiments, the dendrimer-replicon nanoparticle is formulated by a microfluidic mixing device. In some embodiments, the recombinant alphavirus replicon is coated onto the plurality of microneedles using a microfluidic dispensing device. In some embodiments, the recombinant alphavirus replicon is present in an amount effective to induce an immune response in the individual to the exogenous polypeptide. In some embodiments, a second bioactive agent packaged in or on the microneedles. In some embodiments, the second bioactive agent is a polypeptide. In some embodiments, the second bioactive agent enhances an immune response. In some embodiments, the second bioactive agent is an adjuvant. In some embodiments, the dermal surface is pretreated prior to contacting the individual with the microneedle device. In some embodiments, the individual is contacted with a second microneedle device comprising a plurality of microneedles, wherein each microneedle comprises the recombinant alphavirus replicon encoding the exogenous polypeptide coated onto or embedded into the microneedle. In some embodiments, the individual is administered a second composition comprising the alphavirus replicon encoding the exogenous polypeptide by a second route of administration. In some embodiments, the second route of administration is oral. In some embodiments, oral administration of the second composition is administered prior to contacting the individual with the microneedle device. In some embodiments, oral administration of the second composition is administered after contacting the individual with the microneedle device.

Also disclosed herein, in some embodiments, are methods of monitoring an immune response in an individual comprising: (a) administering to the individual the microneedle device of any one of claims 1-46; and (b) assaying a sample from the individual to determine a level of an immune response in the individual against the exogenous polypeptide.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
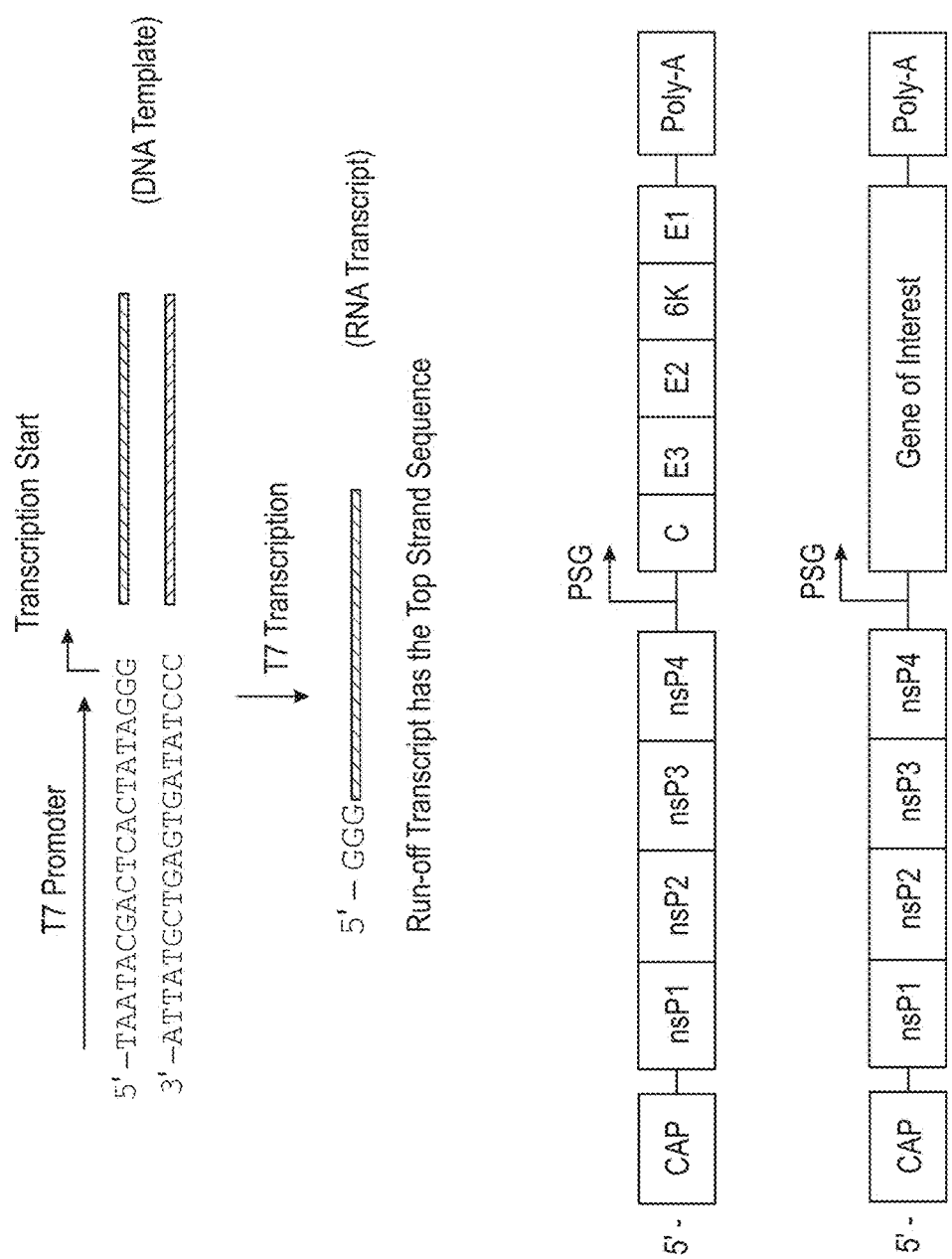
FIG. 1 illustrates an exemplary method of producing recombinant alphavirus replicons for transdermal administration to a subject. A linear DNA template comprises a sequence (SEQ ID NO: 1) that encodes a recombinant alphavirus replicon encoding an exogenous polypeptide. The T7 RNA polymerase transcribes the DNA sequence into an RNA transcript. A wild-type alphavirus replicon cassette containing four non-structural (nsP1, nsP2, nsP3, nsP4) and five structural genes (capsid, E3, E2, 6K, E1) is also illustrated. Typically, one or more, but preferably all, of the structural genes are excluded from the recombinant alphavirus replicon encoding an exogenous polypeptide. After generation of the recombinant alphavirus replicon, it is packaged into or onto a microneedle or microneedle array. The microneedle is applied to the skin of a subject for intradermal administration of the replicon.
Figure 2:
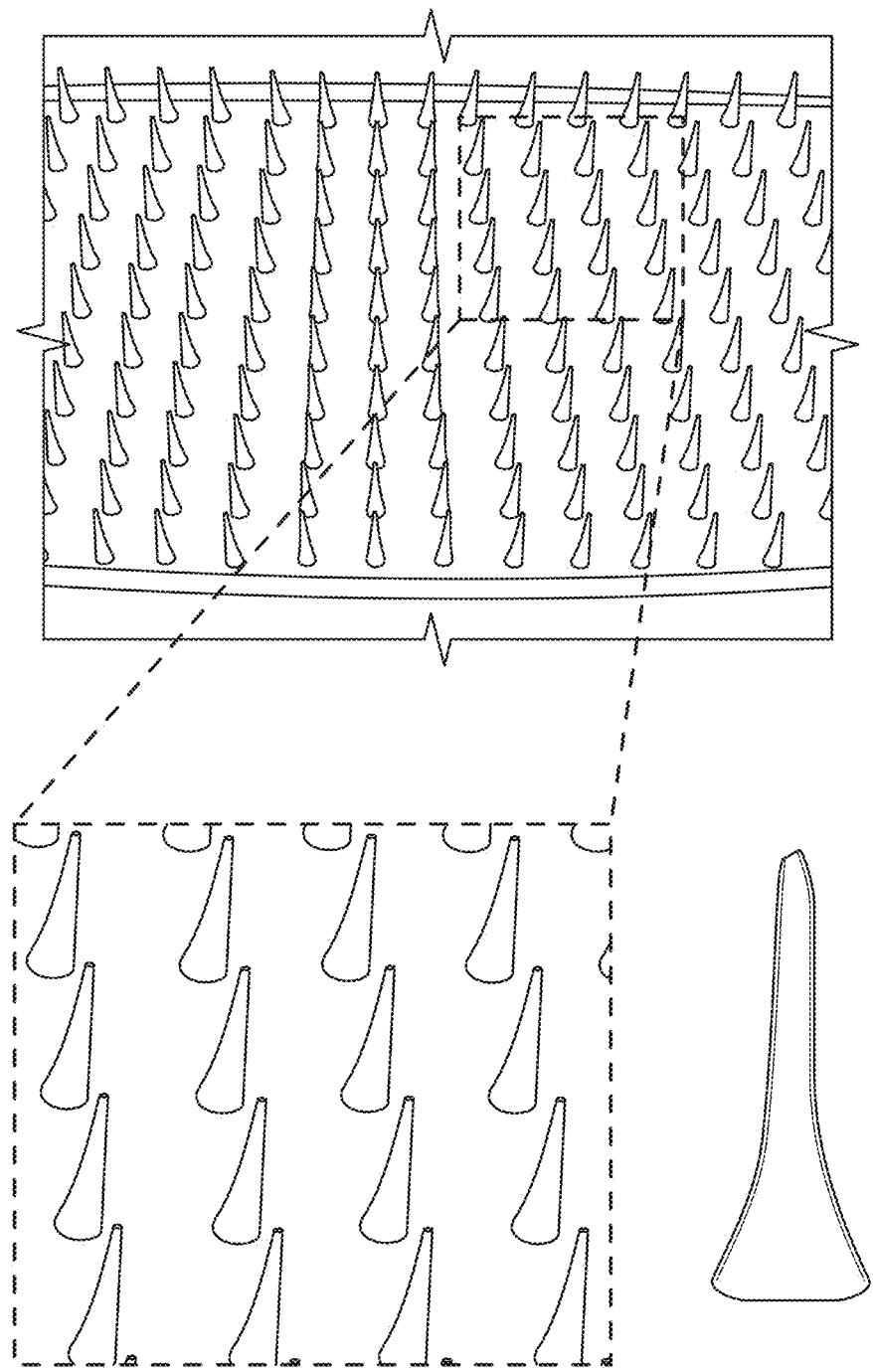
FIG. 2 shows an illustration of a microneedle useful for delivery of a bioactive agent. In some embodiments, needles have a height of about 1500 microns and a base with a diameter of about 670 microns. In some embodiments, microneedles are provided in an array, such as an array on a patch having an area of about 1 cm².

Disclosed herein, in some embodiments, are compositions comprising self-replicating RNAs or replicon RNAs that are formulated for delivery to a subject in need thereof, methods of preparing the same, and methods of administering the compositions to a subject in need thereof, such as for vaccination or gene therapy.

In some embodiments, the compositions comprise a bioactive agent (e.g., a polypeptide, or a recombinant alphavirus replicon or RNA molecule that encodes an exogenous polypeptide), coated onto or embedded into a microneedle or microneedle array. In some embodiments, the bioactive agent is coated onto or embedded into the microneedle and the bioactive agent is in a dehydrated form. In some embodiments, the bioactive agent comprises a recombinant alphavirus replicon. In some embodiments, the recombinant alphavirus replicons are embedded into a microneedle. In some embodiments, the recombinant alphavirus replicons are coated onto a microneedle. In some embodiments, the recombinant alphavirus replicons are coated onto a microneedle by dipping, followed by dehydration of the coated alphavirus replicon. In some embodiments, the recombinant alphavirus replicons are coated onto a microneedle by a microfluidic dispensing device, followed by dehydration of the coated alphavirus replicon. In some embodiments, the microfluidic dispensing device is a Bio-Dot printer, or similar device. In some embodiments, the alphavirus replicons are formulated into an alphavirus replicon-dendrimer nanoparticle. In some embodiment, the dendrimer is a PAMAM dendrimer. In some embodiments, the dendrimer is a PAMAM dendrimer with amino surface reactive groups. In some embodiments, the PAMAM dendrimer with amino surface reactive groups is a G5 or G9 PAMAM dendrimer. In some embodiments, the dendrimer is a PAMAM dendrimer that comprises modified (e.g., fluorinated) amino surface reactive groups. In some embodiments, the alphavirus replicon-dendrimer nanoparticle is formulated by hand mixing. In some embodiments, the alphavirus replicon-dendrimer nanoparticle is formulated by a microfluidic mixing device. In some embodiments, the microfluidic mixing device is a Precision NanoSystems NanoAssemblr, or similar device.

Certain Terminology

The terms "polynucleotide," "nucleotide," "nucleotide sequence," "nucleic acid," and "oligonucleotide" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. In some embodiments, a polynucleotide comprises one or more modified nucleotides, such as methylated nucleotides and nucleotide analogs. In some embodiments, modifications to the nucleotide structure are imparted before or after assembly of the polymer. In some embodiments, the sequence of nucleotides is interrupted by non-nucleotide components. In some embodiments, the polynucleotide is further modified after polymerization, such as by conjugation with a labeling component.

The terms "polypeptide," "peptide," and "protein" are used interchangeably herein to refer to polymers of amino acids of any length. In some embodiments, a polypeptide is any protein, peptide, protein fragment, or component thereof. In some embodiments, a polypeptide is a protein naturally occurring in nature or a protein that is ordinarily not found in nature. In some embodiments, a polypeptide consists largely of the standard twenty protein-building amino acids or it is modified to incorporate non-standard amino acids. In some embodiments, a polypeptide is modified, typically by the host cell, for example, by adding any number of biochemical functional groups, including phosphorylation, acetylation, acylation, formylation, alkylation, methylation, lipid addition (e.g., palmitoylation, myristoylation, prenylation, etc.) and carbohydrate addition (e.g., N-linked and O-linked glycosylation, etc.). In some embodiments, polypeptides undergo structural changes in the host cell such as the formation of disulfide bridges or proteolytic cleavage.

In general, "sequence identity" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Any suitable technique is contemplated by the disclosure herein. In some embodiments, two or more sequences (polynucleotide or amino acid) are compared by determining their "percent identity." In some embodiments, ranges of desired degrees of sequence identity are approximately 80% to 100% and integer values there between. In some embodiments, the percent identities between a disclosed sequence and a claimed sequence are at least 80%, at least 85%, at least 90%, at least 95%, or at least 98%.

The terms "subject," "individual," and "patient" are used interchangeably herein to refer to a vertebrate, preferably a mammal, more preferably a human. In some embodiments, mammals include, but are not limited to: murines, simians, humans, farm animals, sport animals, and pets. In some embodiments, tissues, cells, and their progeny of a biological entity obtained in vivo or cultured in vitro are encompassed. None of these terms, as used herein, entail supervision of a medical professional.

As used herein, the term "about" is used to indicate that a value includes the standard deviation of error for the device or method being employed to determine the value.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an," and "the" include plural referents unless the context clearly dictates otherwise. In this application, the use of "or" means "and/or" unless stated otherwise. Furthermore, use of the term "including" as well as other forms, such as "include," "includes," and "included," is not intended to be limited solely to the recited items. The section headings used herein are for organizational purposes only and are not to be construed as limiting the subject matter described.

Microneedles and Microneedle Arrays

Disclosed herein, in some embodiments, are microneedle devices for administering a recombinant alphavirus replicon or RNA molecule encoding an exogenous polypeptide comprising: a substrate comprising a plurality of microneedles; and a composition comprising a recombinant alphavirus replicon or RNA molecule encoding an exogenous polypeptide coated onto or embedded into the plurality of microneedles. Also disclosed herein, in some embodiments, are methods of preparing a microneedle device, comprising: obtaining a substrate comprising a plurality of microneedles; and coating or embedding a recombinant alphavirus replicon encoding an exogenous polypeptide onto or into the plurality of microneedles. Also disclosed herein, in some embodiments, are methods of inducing an immune response in an individual in need thereof, comprising: (a) contacting the dermal surface of an individual with a microneedle device comprising (i) a plurality of microneedles comprising a recombinant alphavirus replicon encoding an exogenous polypeptide coated onto or embedded into the plurality of microneedles, and (b) delivering the recombinant alphavirus replicon to the individual, thereby inducing an immune response in the individual.

Microneedles are structures of typically micrometer to millimeter size, and preferably designed to pierce the skin and deliver a composition to the epidermis or dermis of a subject. Microneedles offer some advantages over traditional sub-cutaneous or intramuscular injections. In some embodiments, microneedles are used to deliver the replicon directly to the immune cells in the skin, which is advantageous for immunization purposes. The amount of replicon needed for microneedle administration, compared to traditional sub-cutaneous or intramuscular injections, is smaller and can reduce production cost and time. In some embodiments, the microneedle is self-administered. In some embodiments, the replicon is dried onto the microneedle, which greatly increases the stability of the composition at room temperature. Microneedle administration is painless, making it a more tolerated form of administration.

In some embodiments, microneedles are solid structures. In some embodiments, microneedles are hollow structures. In some embodiments, bioactive agents for delivery (e.g., polypeptides or recombinant alphavirus replicons or RNA molecules) are released through hollow structures (e.g., a liquid composition is injected or infused into the skin). In some embodiments, bioactive agents (e.g., polypeptides or recombinant alphavirus replicons or RNA molecules) are packaged onto a microneedle (for example, coated onto a surface of the microneedle after formation). In some embodiments, the bioactive agents are packaged onto a microneedle as a dried form. In some embodiments, the bioactive agents are dehydrated after being packaged onto a microneedle. In some embodiments, compositions are packaged into a microneedle (for example, forming part of the microneedle itself, such as by deposition into the interior of the microneedle, or by inclusion in a mixture used to form the microneedle). In some embodiments, the replicon is dissolved in the skin compartment. In some embodiments, the replicon is injected into the skin. In some embodiments, microneedles are formed in an array comprising a plurality of microneedles. In some embodiments, the microneedle array is a 5×5 array of microneedles. In some embodiments, the microneedle array is physically or operably coupled to a solid support or substrate. In some embodiments, the solid support is a patch. In some embodiments, the microneedle array is applied directly to the skin for intradermal administration of a composition.

A microneedle array patch can be any suitable shape or size. In some embodiments, a microneedle array patch is shaped to mimic facial features, e.g., an eyebrow. In some embodiments, a microneedle array patch is the smallest size allowable to deliver a selected amount of bioactive agent.

The size and shape of the microneedles varies as desired. In some embodiments, microneedles include a cylindrical portion physically or operably coupled to a conical portion having a tip. In some embodiments, microneedles have an overall pyramidal shape or an overall conical shape. In some embodiments, the microneedle includes a base and a tip. In some embodiments, the tip has a radius that is less than or equal to about 1 micrometer. In some embodiments, the microneedles are of a length sufficient to penetrate the stratum corneum and pass into the epidermis or dermis. In certain embodiments, the microneedles have a length (from their tip to their base) between about 0.1 micrometer and about 5 millimeters in length, for instance about 5 millimeters or less, 4 millimeters or less, between about 1 millimeter and about 4 millimeters, between about 500 micrometers and about 1 millimeter, between about 10 micrometers and about 500 micrometers, between about 30 micrometers and about 200 micrometers, or between about 250 micrometers to about 1,500 micrometers. In some embodiments, the microneedles have a length (from their tip to their base) between about 400 micrometers to about 600 micrometers.

In some embodiments, the size of individual microneedles is optimized depending upon the desired targeting depth or the strength requirements of the needle to avoid breakage in a particular tissue type. In some embodiments, the cross-sectional dimension of a transdermal microneedle is between about 10 nm and 1 mm, or between about 1 micrometer and about 200 micrometers, or between about 10 micrometers and about 100 micrometers. In some embodiments, the outer diameter of a hollow needle is between about 10 micrometers and about 100 micrometers and the inner diameter of a hollow needle is between about 3 micrometers and about 80 micrometers.

Microneedles can be arranged in a variety of different patterns. In some embodiments, the microneedles are spaced apart in a uniform manner, such as in a rectangular or square grid or in concentric circles. In some embodiments, the microneedles are spaced on the periphery of the substrate, such as on the periphery of a rectangular grid. In some embodiments, the spacing depends on numerous factors, including height and width of the microneedles, the characteristics of a film to be applied to the surface of the microneedles, as well as the amount and type of a substance that is intended to be moved through the microneedles. In some embodiments, the arrangement of microneedles is a "tip-to-tip" spacing between microneedles of about 50 micrometers or more, about 100 micrometers to about 800 micrometers, or about 200 micrometers to about 600 micrometers.

In some embodiments, the microneedle composition is of any suitable material. Example materials include metals, ceramics, semiconductors, organics, polymers, and composites. In some embodiments, materials of construction include, but are not limited to: pharmaceutical grade stainless steel, gold, titanium, nickel, iron, gold, tin, chromium, copper, alloys of these or other metals, silicon, silicon dioxide, and polymers. In some embodiments, the polymer is a biodegradable polymer or a non-biodegradable polymer. Representative biodegradable polymers include, but are not limited to: polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polymethacrylic acid, ethylenevinyl acetate, polytetrafluorethylene and polyesters.

In some embodiments, the microneedle is dissolvable, biosoluble, biodegradable, or any combinations thereof. "Biodegradable" is used to refer to any substance or object that is decomposed by bacteria or another living organism. Any suitable dissolvable, biosoluble, and/or biodegradable microneedles are contemplated for use with the compositions and methods disclosed herein. In some embodiments, the dissolvable, biosoluble, or biodegradable microneedles are composed of water soluble materials. In some embodiments, these materials include chitosan, collagen, gelatin, maltose, dextrose, galactose, alginate, agarose, cellulose (such as carboxymethylcellulose or hydroxypropylcellulose), starch, hyaluronic acid, or any combinations thereof. In some embodiments, a selected material is resilient enough to allow for penetration of the skin. In some embodiments, the dissolvable microneedle dissolves in the skin within seconds, such as within about 5, 10, 15, 20, 25, 30, 45, 50, 60, 120, 180, or more seconds. In some embodiments, the dissolvable microneedle dissolves in the skin within minutes, such as within about 1, 2, 3, 4, 5, 6, 7, 8, 9, 10, 15, 20, 30, 60, 120 or more minutes. In some embodiments, the dissolvable microneedle comprises a dissolvable portion (such as the tip of the microneedle) and a non-dissolvable portion (such as the base of a microneedle), such that a portion of the microneedle structure dissolves in the skin. In some embodiments, the dissolvable microneedle encompasses the entire microneedle, such that the entire microneedle structure dissolves in the skin. In some embodiments, a dissolvable coating is formed on a non-dissolvable support structure such that only the coating dissolves in the skin. In some embodiments, the microneedle is coated with a polymer that is dissolvable, biodegradable, biosoluble, or any combinations thereof.

In some embodiments, replicon compositions are directly coated onto the dissolvable, biodegradable, or biosoluble microneedle. In some embodiments, replicon compositions are contained within the dissolvable, biodegradable, or biosoluble microneedle itself (e.g., by forming part of the dissolvable polymer matrix). In some embodiments, replicon compositions are mixed with a polymer matrix prior to molding and polymerization of microneedle structures.

A variety of methods for manufacturing microneedles are available and any suitable method for manufacturing microneedles or microneedle arrays are contemplated for use with the compositions and methods disclosed herein. In some embodiments, microneedles are manufactured using any suitable method, including, but not limited to: molding (e.g., self-molding, micromolding, microembossing, microinjection, and the like), casting (e.g., die-casting), or etching (e.g., soft microlithography techniques). The method of manufacture used depends on the materials employed.

In some embodiments, a microneedle composition comprises a bioactive agent. In some embodiments, the terms "biologically active" and "bioactive" refers to a composition or compound itself that has a biological effect, or a composition or compound that binds, reacts, modifies, causes, promotes, enhances, blocks, or reduces the activity of a second molecule that has a biological effect. In some embodiments, the second molecule is an endogenous molecule. In some embodiments, the second molecule is an exogenous molecule. In some embodiments, a "biological effect" includes, but is not limited to an effect that: stimulates or causes an immunoreactive response; impacts a biological process in a cell, tissue, or organism (e.g., in an animal); impacts a biological process in a pathogen or parasite; or generates or causes to be generated a detectable signal. In some embodiments, biologically active compositions, complexes, or compounds are used in investigative, therapeutic, prophylactic, and/or diagnostic methods and compositions. In some embodiments, biologically active compositions, complexes, or compounds act to cause or stimulate a desired effect upon a cell, tissue, organ, or organism (e.g., an animal). Non-limiting examples of desired effects include, but are not limited to: modulating, inhibiting, or enhancing gene expression in a cell, tissue, organ, or organism; preventing, treating, or curing a disease or condition in an animal suffering therefrom; limiting the growth of or killing a pathogen in an animal infected thereby; augmenting the phenotype or genotype of an animal; stimulating a prophylactic immunoreactive response in an animal; and diagnosing a disease or disorder in an animal.

In some embodiments, a microneedle composition comprises a bioactive agent. In some embodiments, the bioactive agent is the recombinant alphavirus replicons described herein. In some embodiments, the bioactive agent is an RNA molecule encoding an exogenous polypeptide. In some embodiments, a bioactive agent comprises a polypeptide, such as any of the polypeptides described herein. In some embodiments, the bioactive agent comprises an antigen. In some embodiments, the bioactive agent comprises an epitope of an antigen. In some embodiments, a microneedle composition comprises a recombinant alphavirus replicon encoding an exogenous polypeptide and further comprises a polypeptide. For example, a polypeptide useful as a bioactive agent is an influenza virus antigen, e.g., hemagglutinin (HA). In some embodiments, a replicon composition comprises a replicon RNA encoding an HA protein and a bioactive molecule comprising an epitope of one or more different HA proteins. In some embodiments, a replicon composition comprises a replicon RNA encoding a hepatitis B surface antigen (HBsAg). In some embodiments, a bioactive agent is a polypeptide that enhances an immune response (e.g., an antigen or an adjuvant).

In some embodiments, the microneedle composition comprises 2, 3, 4, 5, 6, 7, 8, 9, 10, or more different bioactive agents. In some embodiments, the microneedle composition comprises 2 different bioactive agents. In some embodiments, the microneedle composition comprises 3 different bioactive agents. In some embodiments, the microneedle composition comprises 4 different bioactive agents. In some embodiments, the microneedle composition comprises 5 different bioactive agents. In some embodiments, the microneedle composition comprises 6 different bioactive agents. In some embodiments, the microneedle composition comprises 7 different bioactive agents. In some embodiments, the microneedle composition comprises 8 different bioactive agents. In some embodiments, the microneedle composition comprises 9 different bioactive agents. In some embodiments, the microneedle composition comprises 10 different bioactive agents. In some embodiments, the bioactive agents are of the same type (e.g., multiple alphavirus replicons, each encoding a different polypeptide). In some embodiments, a single alphavirus replicon encodes multiple bioactive agents (e.g., multiple exogenous polypeptides). In some embodiments, each exogenous polypeptide is encoded by a separate alphavirus replicon. In some embodiments, the bioactive agents are of different type (e.g., comprises an alphavirus replicons and a polypeptide).

In some embodiments, the microneedle composition comprises two bioactive agents. In some embodiments, the microneedle composition comprises two different bioactive agents, such as two different recombinant alphavirus replicons, two different polypeptides, or a recombinant alphavirus replicon and a polypeptide. In some embodiments, the microneedle composition comprises two different recombinant alphavirus replicons, each encoding for a different polypeptide. In some embodiments, the microneedle composition comprises a single recombinant alphavirus replicon that encodes for two different polypeptides. In some embodiments, the microneedle composition comprises a replicon encoding an HA polypeptide from an influenza H1 viral strain and a replicon encoding an HA polypeptide from an influenza H3 viral strain (bivalent vaccine). In some embodiments, a single alphavirus replicon encodes an HA polypeptide from an influenza H1 viral strain and an HA polypeptide from an influenza H3 viral strain. In some embodiments, the HA polypeptide from an influenza H1 viral strain and the HA polypeptide from an influenza H3 viral strain are encoded on a separate alphavirus replicon. In some embodiments, the microneedle composition comprises two bioactive agents, such as a polypeptide and a recombinant alphavirus replicon encoding the same polypeptide (e.g., an influenza H1 polypeptide and a replicon encoding the influenza H1 polypeptide). In some embodiments, the microneedle composition comprises two different bioactive agents, such a polypeptide and a recombinant alphavirus replicon encoding a different polypeptide (e.g., an influenza H1 polypeptide and a replicon encoding an influenza H3 polypeptide).

In some embodiments, the microneedle composition comprises three bioactive agents. In some embodiments, the microneedle composition comprises three different recombinant alphavirus replicons, each encoding for a different polypeptide. In some embodiments, the microneedle composition comprises a single recombinant alphavirus replicon that encodes for three different polypeptides. In some embodiments, the microneedle composition comprises a replicon encoding an HA polypeptide from an influenza H1 viral strain, a replicon encoding an HA polypeptide from an influenza H3 viral strain, and a replicon encoding an HA polypeptide from an influenza B HA viral strain (trivalent vaccine). In some embodiments, a single alphavirus replicon encodes the HA polypeptide from an influenza H1 viral strain, the HA polypeptide from an influenza H3 viral strain, and the HA polypeptide from an influenza B HA viral strain. In some embodiments, the HA polypeptide from an influenza H1 viral strain, the HA polypeptide from an influenza H3 viral strain, and the HA polypeptide from an influenza B HA viral strain are encoded on three separate alphavirus replicons. In some embodiments, the microneedle composition comprises three different bioactive agents, wherein at least one of the bioactive agents is a polypeptide.

In some embodiments, the microneedle composition comprises four bioactive agents. In some embodiments, the microneedle composition comprises four different recombinant alphavirus replicons, each encoding for a different polypeptide. In some embodiments, the microneedle composition comprises a single recombinant alphavirus replicon that encodes for four different polypeptides. In some embodiments, the microneedle composition comprises a replicon encoding an HA polypeptide from an influenza H1 viral strain, a replicon encoding an HA polypeptide from an influenza H3 viral strain, a replicon encoding an HA polypeptide from an influenza B Yamagata lineage viral strain, and a replicon encoding an HA polypeptide from an influenza B Victoria lineage viral strain (quadrivalent vaccine). In some embodiments, a single alphavirus replicon encodes the HA polypeptide from an influenza H1 viral strain, the HA polypeptide from an influenza H3 viral strain, the HA polypeptide from an influenza B Yamagata lineage viral strain, and the HA polypeptide from an influenza B Victoria lineage viral strain. In some embodiments, the HA polypeptide from an influenza H1 viral strain, the HA polypeptide from an influenza H3 viral strain, the HA polypeptide from an influenza B Yamagata lineage viral strain, and the HA polypeptide from an influenza B Victoria lineage viral strain are encoded on four separate alphavirus replicons. In some embodiments, the microneedle composition comprises four different bioactive agents, wherein at least one of the bioactive agents is a polypeptide. In some embodiments, a single alphavirus replicon encodes five exogenous polypeptides, such as any of the exogenous polypeptides disclosed herein.

In some embodiments, a bioactive agent is an adjuvant. Exemplary adjuvants include, without limitation: aluminum salts (e.g., aluminum phosphate, aluminum hydroxide); squalene; saponins (QS21, ISCOMS), saponins complexed to membrane protein antigens (immune stimulating complexes); pluronic polymers with mineral oil, killed Mycobacteria in mineral oil, a water-in-mineral-oil emulsion which contains killed/dried mycobacteria in the oil phase, a weaker formulation without the mycobacteria; Freund's complete adjuvant; Freund's incomplete adjuvant; bacterial products, such as muramyl dipeptide (MDP) and lipopolysaccharide (LPS), MPL as well as lipid A; liposomes, a membrane active glucoside extracted from the tree *Quillia saponaria*, nonionic block copolymer surfactants; non-metabolised synthetic molecules which tend to bind proteins to cell surfaces; Infectious particles; Oil-in-water emulsions (e.g., MF59); CpG (Oligonucleotides)—TLR agonists; and other TLR agonists like imiquimod and immunopeptides.

In some embodiments, bioactive agents are packaged onto microneedles. In some embodiments, bioactive agents are packaged or embedded into microneedles. In some embodiments, the bioactive agent is an RNA molecule encoding an exogenous polypeptide. In some embodiments, the bioactive agent is a recombinant alphavirus replicon. In some embodiments, the alphavirus replicon is dehydrated before packaging into or onto the microneedle. In some embodiments, the alphavirus replicon is dehydrated after packaging into or onto the microneedle. In some embodiments, the microneedle is packaged individually at a unit dose of replicon. In some embodiments, the unit dose is effective in inducing an immune response in a subject to the exogenous polypeptide. In some embodiments, the unit dose is effective in inducing an immune response in a subject to the exogenous polypeptide after storage for at least about one week (e.g., about or more than about 1, 2, 3, 4, 6, 8, 12, or more weeks) at room temperature. In some embodiments, the unit dose is effective in inducing an immune response in a subject to the exogenous polypeptide after storage for at least about one month (e.g., about or more than about 1, 2, 3, 4, 5, 6, 8, 10, 12, or more months) at room temperature. In some embodiments, the recombinant alphavirus replicon is present in an amount effective to induce an immune response in the subject to the exogenous polypeptide. In some embodiments, the recombinant alphavirus replicon is present in an amount effective to alone induce an immune response to the foreign or self-antigen. In some embodiments, the amount of recombinant alphavirus replicon varies depending upon the health and physical condition of the individual to be treated, age, the taxonomic group of individual to be treated (e.g., non-human primate, primate, human, etc.), the capacity of the individual's immune system to synthesize antibodies, the degree of protection desired, the formulation of the vaccine, and other relevant factors. In some embodiments, the polypeptide and RNA content of certain compositions is expressed in terms of an amount of RNA per dose. In some embodiments, a dose has ≤100 µg RNA (e.g., from 10-100 µg, such as about 10 µg, 25 µg, 50 µg, 75 µg or 100 µg). In some embodiments, expression is seen at much lower levels (e.g., ≤1 µg/dose, ≤100 ng/dose, ≤10 ng/dose, ≤1 ng/dose).

Self-Replicating RNA Molecules

In some embodiments, the bioactive agents packaged for delivery into or onto microneedles are replicons. A "replicon" refers to a DNA or RNA molecule that is capable of undergoing self-replication, in whole or in part, such as in a self-replicating nucleic acid molecule. In preferred embodiments, the replicon is an RNA molecule. Replicon RNA can substantially amplify the production of an encoded protein, leading to sustained translation and protein production in a target cell. In some embodiments, RNA replicons are based on or derived from viruses. A variety of suitable viruses (e.g., RNA viruses) are available, including, but not limited to, picornavirus, flavivirus, coronavirus, pestivirus, rubivirus, calcivirus, and hepacivirus. In preferred embodiments, the RNA replicon is derived from an alphavirus. In some embodiments, replicons are positive-stranded so that they are directly translated by the host cell without requiring intermediate replication steps, such as reverse transcription. In some embodiments, replicons are derived from negative-stranded viruses. In some embodiments, the negative-stranded virus derived replicon is from Sendai virus or vesicular stomatitis virus. In some embodiments, when a positive-stranded replicon is delivered to a host cell, it is directly translated, generating an RNA-dependent RNA polymerase which then produces both antisense and sense transcripts from the delivered RNA. In some embodiments, these RNA transcripts are translated directly such that the host cell produces an encoded polypeptide, or they are further transcribed to produce more transcripts that are translated by the host cell to produce more encoded polypeptide.

In preferred embodiments, the replicon is derived from an alphavirus. The alphavirus genus belongs to the Togaviridae family and contains 28 known virus species. The positive-sense alphavirus genome typically contains two open-reading frames and encodes four non-structural proteins (nsP1-4) and five structural proteins (capsid, E3, E2, E1, and 6K). In some embodiments, the alphavirus replicons lack the genes encoding the structural proteins. Excluding the genes encoding the structural proteins will prevent viral replication. In some embodiments, the genes encoding the structural proteins are replaced with mRNA encoding an exogenous polypeptide such that the host cell will produce a large amount of exogenous polypeptide, but will not produce infectious viral particles.

A variety of alphaviruses suitable for the provision of elements of a replicon in accordance with the disclosure are available. In some embodiments, replicon sequences comprise a wild-type alphavirus sequence. In some embodiments, replicon sequences comprise a mutated alphavirus sequence. In some embodiments, a replicon derived from an alphavirus comprises sequence elements (e.g., elements that promote replication of a sequence encoding an exogenous polypeptide) that are at least about 80%, 85%, 90%, 95% or more identical to a reference wild-type alphavirus replicon, or a portion thereof (e.g., non-structural genes or portions thereof). In some embodiments, sequence elements derived from an alphavirus are 500, 1000, 1500, 2000, 3000, 4000, 5000, or more nucleotides in length. Example alphaviruses are available from depositories such as the American Type Culture Collection (ATCC), and include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375). In some embodiments, chimeric alphavirus replicons, which include sequences from multiple different alphaviruses, are used. In some embodiments, the alphavirus replicon is derived from Semliki Forest virus, Sindbis virus, Venezuelan equine encephalomyelitis virus, or any combinations thereof. In preferred embodiments, the alphavirus replicon is derived from a Venezuelan equine encephalomyelitis virus.

In some embodiments, the RNA replicon is used as a vector to deliver a nucleic acid encoding an exogenous transcript or polypeptide to a host cell. In some embodiments, the RNA replicon contains an RNA sequence that, when delivered to a host cell, results in the production of a polypeptide or active transcript. In some embodiments, the RNA sequence contains the genetic code for a selected polypeptide and the RNA replicon is said to "encode" that polypeptide or active RNA. The term "exogenous" is used to refer to any molecule (e.g., polypeptide, nucleic acid, and the like) that is not ordinarily encoded by the viral replicon. In some embodiments, an exogenous sequence is inserted into an alphavirus replicon by way of recombinant techniques or artificial synthesis to produce a recombinant polynucleotide comprising the exogenous sequence. In some embodiments, an exogenous polypeptide is derived from an organism other than the alphavirus from which the alphavirus sequence portions of the recombinant replicon are derived. In some embodiments, the replicon is engineered to encode an exogenous polypeptide such that delivery of the engineered RNA replicon into a host cell results in the production of a large amount of exogenous polypeptide by the host cell.

A variety of methods are available for producing a recombinant replicon. In some embodiments, a recombinant replicon is generated in the laboratory by in vitro transcription (IVT) techniques. In some embodiments, IVT uses a linear DNA template, such as a cDNA, linearized bacterial plasmid, or PCR product. In some embodiments, the template DNA has a promoter sequence specific for a DNA-dependent RNA polymerase enzyme to initiate RNA synthesis. Although any suitable technique is contemplated, DNA templates are typically generated and propagated in a bacterial plasmid or are created synthetically (e.g., PCR or other synthetic DNA methods known in the art). In some embodiments, the linear DNA molecule acts as a template for an in vitro enzymatic reaction using a polymerase (e.g., a bacteriophage RNA polymerase) that results in an RNA transcript ("copy") of the template DNA molecule. Examples of bacteriophage RNA polymerases useful in such processes include T7, T3, and SP6 RNA polymerases. In some embodiments, the template DNA comprises an alphavirus replicon comprising four non-structural genes (e.g., nsP1-4) and a sequence encoding the exogenous polypeptide such that the mRNA transcript comprises the recombinant alphavirus replicon encoding the alphavirus non-structural genes (e.g., nsP1-4) and the exogenous polypeptide. Methods for producing alphavirus replicons are available and any suitable method for producing an alphavirus replicon is contemplated for use with the compositions and methods disclosed herein.

The disclosed recombinant alphavirus replicons in accordance with the present disclosure have various lengths. In some embodiments, the recombinant alphavirus replicons are about 4000, 5000, 6000, 7000, 8000, 9000, 10000, 15000, 20000, 30000, or more nucleotides in length. In some embodiments, the recombinant alphavirus replicon is 5000-25000 nucleotides in length (e.g., 8000-15000 nucleotides, or 9000-12000 nucleotides). In some embodiments, a replicon comprises a 5' cap. In some embodiments, the 5' cap is a 7-methylguanosine. In some embodiments, the 5' cap enhances in vivo translation of the RNA.

In some embodiments, the 5' nucleotide of a replicon has a 5' triphosphate group. In some embodiments, in a capped RNA, the 5' triphosphate group is linked to a 7-methylguanosine via a 5'-to-5' bridge. In some embodiments, a 5' triphosphate enhances RIG-I binding and thus promotes adjuvant effects. In some embodiments, a replicon comprises a 3' poly-A tail. In some embodiments, the replicon includes a poly-A polymerase recognition sequence (e.g., AAUAAA) near its 3' end. In some embodiments, a replicon for delivery to a subject is single-stranded. In some embodiments, single-stranded RNAs initiate an adjuvant effect by binding to TLR7, TLR8, RNA helicases, and/or PKR. In some embodiments, RNA is delivered in double-stranded form (dsRNA) and binds to TLR3. In some embodiments, TLR3 is triggered by dsRNA which is formed either during replication of a single-stranded RNA or within the secondary structure of a single-stranded RNA. In some embodiments, a replicon comprises (in addition to any 5' cap structure) one or more nucleotides having a modified nucleobase. In some embodiments, a self-replicating RNA comprises one or more modified pyrimidine nucleobases, such as pseudouridine and/or 5-methylcytosine residues. In some embodiments, the RNA includes no modified nucleobases. In some embodiments, the RNA includes no modified nucleotides (e.g., all of the nucleotides in the RNA are standard A, C, G and U ribonucleotides, except for any 5' cap structure, which, in some embodiments, comprise a 7'-methylguanosine). In some embodiments, the replicon is an RNA comprising a 5' cap comprising a 7'-methylguanosine, and the first 1, 2, 3, or more 5' ribonucleotides are modified at the 2' OH position of the ribose. A variety of 2' OH ribose modifications are available and contemplated for use with the compositions and methods disclosed herein. Exemplary of 2' OH modifications include, but are not limited to: 2'-O-Me, 2'-MOE, 2'-amino, and 2'-F. In some embodiments, an RNA replicon comprises only phosphodiester linkages between nucleosides. In some embodiments, the RNA replicon comprises phosphoramidate, phosphorothioate, methylphosphonate, or other linkages (such as 2'-4'-locked/bridged sugars (e.g., LNA, ENA, or UNA)).

In some embodiments, RNA replicons encoding exogenous polypeptides are prepared for delivery to a subject in need thereof. In some embodiments, a recombinant alphavirus replicon in accordance with the present disclosure is used for vaccination. In some embodiments, a recombinant alphavirus replicon in accordance with the present disclosure is used for vaccination or gene therapy. In some embodiments, replicons used for vaccination encode one or more antigenic polypeptides (also referred to as an "antigen" or "immunogen") and are capable of generating an immunogenic response in the subject, such as by activating the subject's adaptive immune system mediated by a humoral immune response, cell-mediated immune response, or both. In some embodiments, 1, 2, 3, 4, 5, 6, 7, 8, 9, 10, or more antigens are encoded in one or more replicons (e.g., one replicon encoding multiple antigens, or multiple replicons encoding different antigens). In some embodiments, antigens are foreign antigens or self-antigens. In general, the term "self-antigen" refers to an immunogenic antigen or antigenic determinant which is native to the subject. In some embodiments, the self-antigen is an antigen associated with cancer. A "foreign antigen" refers to those antigens that are not self-antigens, such as antigens derived from an infectious agent, a chemical, pollen, and the like. In some embodiments, a foreign antigen is derived from an infectious agent. Exemplary infectious agents include, but are not limited to, bacteria, virus, protozoa, fungi, prions, helminths and other parasites, and any combinations thereof. In some embodiments, foreign antigens derived from infectious agents in the present disclosure are derived from infectious agents that are pathogenic. In some embodiments, the replicon or polypeptide based vaccine disclosed herein provides a protective effect, such as by reducing the incidence of infection (such as by at least about 10%, 20%, 30%, 40%, 50%, 60%, 70%, 80%, 90%, or more), increasing the average number of infectious particles necessary to establish an infection (such as by at least about 25%, 50%, 100%, 250%, 500%, or more), or decreasing the average duration of an associated disease (such as by at least about 10%, 20%, 30%, 40%, 50%, 60%, 70%, 80%, 90%, or more), among a treated population relative to an untreated population. In some embodiments, protective effects are measured in an appropriate animal model, or through an epidemiological study of treated and untreated populations. In some embodiments, an antigen comprises or consists of about 5, 10, 15, 20, 25, 30, 35, 40, 45, 50, 75, 100, 150, 200, 300, 400, 500, 1000, 2000, 3000, 5000, or more amino acids. In some embodiments, an antigen derived from a particular source typically has about 80%, 90%, 95%, 99%, or more sequence identity at the nucleotide or amino acid level when optimally aligned to the sequence from which it was derived over the length of the antigen.

In some embodiments, the antigen encoded by a recombinant alphavirus replicon of the disclosure is an influenza virus hemagglutinin (HA) protein. In some embodiments, the antigen encoded by a recombinant alphavirus replicon of the disclosure is an influenza virus neuraminidase (NA) protein. In some embodiments, HA is derived from a viral strain of an influenza A, B, or C virus. In some embodiments, the antigen is derived from a viral strain of influenza A virus and comprises one or more HA subtypes including H1, H2, H3, H4, H5, H6, H7, H8, H9, H10, H11, H12, H13, H14, H15, H16, H17, or HA18. In some embodiments, multiple replicons each encoding a different HA are used, such that an immunogenic response to more than one HA is elicited. In some embodiments, a single replicon encoding multiple different HA polypeptides are used, such that an immunogenic response to more than one HA is elicited. In some embodiments, the replicon composition is monovalent (the vaccine protects against one influenza strain, such as one HA subtype antigen, e.g., H1), bivalent (the vaccine protects against two influenza strains, such as two HA subtype antigens, e.g., H1 and H3), trivalent (the vaccine protects against three influenza strains, such three HA subtype antigens, e.g., H1, H3, and a circulating influenza B strain); quadrivalent (the vaccine protects against four influenza strains, such as four HA subtype antigens, e.g., H1, H3, influenza B Yamagata, and influenza B Victoria); or still higher valencies. In some embodiments, the HA antigens are determined based on the dominant influenza strains (or the predicted most dominant strains) causing pathogenesis in any particular season. In some embodiments, the microneedle composition is bivalent and comprises alphavirus replicons that encode an HA polypeptide from a viral strain of an influenza A H1 virus; and an HA polypeptide from a viral strain of an influenza A H3 virus. In some embodiments, the bivalent HA polypeptides are encoded in the same alphavirus replicon. In some embodiments, the bivalent HA polypeptides are encoded on separate alphavirus replicons. In some embodiments, the microneedle composition is trivalent and comprises alphavirus replicons that encode an HA polypeptide from a viral strain of an influenza A H1 virus; an HA polypeptide from a viral strain of an influenza A H3 virus; and an HA polypeptide from a viral strain of a circulating influenza B virus. In some embodiments, the trivalent HA polypeptides are encoded in the same alphavirus replicon. In some embodiments, the trivalent HA polypeptides are encoded on separate alphavirus replicons. In some embodiments, the microneedle composition is quadrivalent and comprises alphavirus replicons that encode an HA polypeptide from a viral strain of an influenza A H1 virus; an HA polypeptide from a viral strain of an influenza A H3 virus; an HA polypeptide from a viral strain of an influenza B Yamagata lineage virus; and an HA polypeptide from a viral strain of an influenza B Victoria lineage virus. In some embodiments, the quadrivalent HA polypeptides are encoded in the same alphavirus replicon. In some embodiments, the quadrivalent HA polypeptides are encoded on separate alphavirus replicons. In some embodiments, the HA subtype chosen for the immunogenic composition is dictated by the most dominant influenza strain(s) (or influenza strain(s) predicted to be the most dominant) during any given season. In some embodiments, the replicon encoding the HA antigen generates an immune response (especially an antibody response), to the influenza virus antigen in a subject when delivered to the subject.

In some embodiments, the polypeptide encoded by the recombinant alphavirus replicon is an antigen derived from hepatitis B virus. In some embodiments, the polypeptide encoded by the recombinant alphavirus replicon is hepatitis B surface antigen (HBsAg).

In some embodiments, the polypeptide encoded by the recombinant alphavirus replicon is an antigen from a polio virus. In some embodiments, the polypeptide encoded by the recombinant alphavirus replicon is an antigen from *Clostridium tetani*. In some embodiments, the polypeptide encoded by the recombinant alphavirus replicon is an antigen from a rabies virus. In some embodiments, the microneedle devices disclosed herein comprise a recombinant alphavirus replicon that encodes an exogenous polypeptide from: (a) an antigen from a polio virus; (b) an antigen from *Clostridium tetani*; and (c) an antigen from a rabies virus. In some embodiments, each of the exogenous polypeptides are encoded on a single recombinant alphavirus replicon. In some embodiments, the exogenous polypeptides are encoded on different recombinant alphavirus replicons. Any suitable polio virus, *Clostridium tetani*; or rabies virus antigens are contemplated by the disclosure herein.

In some embodiments, the polypeptide encoded by the recombinant alphavirus replicon is an antigen from a Marburg virus. In some embodiments, the polypeptide encoded by the recombinant alphavirus replicon is an antigen from an Ebola Sudan virus. In some embodiments, the polypeptide encoded by the recombinant alphavirus replicon is an antigen from an Ebola Zaire virus. In some embodiments, the microneedle devices disclosed herein comprise a recombinant alphavirus replicon that encodes an exogenous polypeptide from: (a) an antigen from a Marburg virus; (b) an antigen from an Ebola Sudan virus; and (c) an antigen from an Ebola Zaire virus. In some embodiments, each of the exogenous polypeptides are encoded on a single recombinant alphavirus replicon. In some embodiments, the exogenous polypeptides are encoded on different recombinant alphavirus replicons. Any suitable Marburg virus, Ebola Sudan virus, or Ebola Zaire virus antigens are contemplated by the disclosure herein.

In some embodiments, the polypeptide encoded by the recombinant alphavirus replicon is an antigen derived from human immunodeficiency virus (HIV). In some embodiments, the HIV antigen is Gp120, Gp160, Gag, Pol, and Nef proteins or portions thereof. Examples of other HIV antigens include Tat, Rev, Vif, Vpr, and Vpu proteins. The replicon encoding an HIV antigen will preferably generate an immune response (such as an antibody response), to the HIV virus epitope in a subject when delivered to the subject.

In some embodiments, the polypeptide encoded by the recombinant alphavirus replicon is an antigen derived from a bacterium. In some embodiments, antigens derived from a bacterium include those derived from any one or more of: *Neisseria meningitidis*, including membrane proteins such as adhesins, autotransporters, toxins, iron acquisition proteins, and factor H binding protein; *Streptococcus pneumoniae* such as the RrgB pilus subunit, the beta-N-acetylhexosaminidase precursor (spr0057), spr0096, General stress protein GSP-781 (spr2021, SP2216), serine/threonine kinase StkP (SP1732), and pneumococcal surface adhesin PsaA; *Streptococcus pyogenes* such as streptococcal group A antigen; *Moraxella catarrhalis*; *Bordetella pertussis* such as pertussis toxin or toxoid (PT), filamentous haemagglutinin (FHA), pertactin, and agglutinogens 2 and 3; *Staphylococcus aureus* such as hemolysin, esxA, esxB, fern chrome-binding protein (sta006) and/or the staOl 1 lipoprotein; *Clostridium tetani* such as tetanus toxoid; *Cornynebacterium diphtheriae* such as diphtheria toxoid; *Haemophilus influenzae*; *Pseudomonas aeruginosa*; *Streptococcus agalactiae*; *Chlamydia trachomatis* such as PepA, LcrE, ArtJ, DnaK, CT398, OmpH-like, L7/L12, OmcA, AtoS, CT547, Eno, HtrA and MurG; *Chlamydia pneumoniae*; *Helicobacter pylori* such as CagA, VacA, NAP, and/or urease; *Escherichia coli* such as immunogens derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC strains include uropathogenic *E. coli* (UPEC) and meningitis/sepsis-associated *E. coli* (MNEC). A useful immunogen for several *E. coli* types is AcfD; *Bacillus anthracis*. In some embodiments, antigens are derived from *Yersinia pestis*; *Staphylococcus epidermis*; *Clostridium perfringens* or *Clostridium botulinums*; *Legionella pneumophila*; *Coxiella burnetii*; *Brucella*, such as *B. abortus, B. canis, B. meliten-* sis, *B. neotomae, B. ovis, B. suis, B. pinnipediae; Francisella*, such as *F. novicida, F. philomiragia, F. tularensis; Neisseria gonorrhoeae; Treponema pallidum; Haemophilus ducreyi; Enterococcus faecalis; Enterococcus faecium; Staphylococcus saprophyticus; Yersinia enterocolitica; Mycobacterium tuberculosis; Rickettsia; Listeria monocytogenes; Vibrio cholerae; Salmonella typhi; Borrelia burgdorferi; Porphyromonas gingivalis*; and *Klebsiella*.

In some embodiments, the polypeptide encoded by the recombinant alphavirus replicon is an antigen derived from a virus. In some embodiments, the viral antigen is derived from any one or more of: Orthomyxovirus; influenza A, B or C virus, such as the hemagglutinin, neuraminidase or matrix M2 proteins; Paramyxoviridae viruses such as those derived from Pneumoviruses (e.g. respiratory syncytial virus, RSV), Rubulaviruses (e.g. mumps virus), Paramyxoviruses (e.g. parainfluenza virus), Metapneumoviruses and Morbilliviruses (e.g. measles); Poxviridae including those derived from Orthopoxvirus such as Variola vera, including but not limited to, Variola major and Variola minor; Picornavirus such as those derived from Enteroviruses, Rhinoviruses, Heparnaviruses, Cardioviruses and Aphthoviruses; Bunyavirus including those derived from an Orthohunyavirus, such as California encephalitis virus, a Phlebovirus, such as Rift Valley Fever virus, or a Nairovirus, such as Crimean-Congo hemorrhagic fever virus; Heparnavirus such as hepatitis A virus (HAV); Filovirus such as an Ebola virus (including a Zaire, Ivory Coast, Reston or Sudan ebolavirus) or a Marburg virus; Togavirus including a Rubivirus, an Alphavirus, or an Arterivirus including Rubella virus; Flavivirus such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus; Pestivirus such as Bovine viral diarrhea virus (BVDV), Classical swine fever (CSFV) or Border disease (BDV); Hepadnavirus such as Hepatitis B virus (e.g. hepatitis B virus surface antigen (HBsAg)); other hepatitis viruses such as hepatitis C virus, delta hepatitis virus, hepatitis E virus, or hepatitis G virus; Rhabdovirus including a Lyssavirus (e.g. a Rabies virus) and Vesiculovirus (VSV); Caliciviridae including Norwalk virus (Norovirus), and Norwalk-like Viruses, such as Hawaii Virus and Snow Mountain Virus; Coronavirus including immunogens derived from a SARS coronavirus, avian infectious bronchitis (IBV), Mouse hepatitis virus (MHV), and Porcine transmissible gastroenteritis virus (TGEV). In some embodiments, the coronavirus immunogen is a spike polypeptide; Retrovirus such as an Oncovirus, a Lentivirus (e.g. HIV-1 or HIV-2) or a Spumavirus; Reovirus including an Orthoreovirus, a Rotavirus, an Orbivirus, or a Coltivirus; Parvovirus including Parvovirus B19; Herpesvirus including a human herpesvirus, such as, by way of example only, Herpes Simplex Viruses (HSV) (e.g. HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8); Papovaviruses including those derived from Papillomaviruses and Polyomaviruses. In some embodiments, the (human) papillomavirus is of serotype 1, 2, 4, 5, 6, 8, 11, 13, 16, 18, 31, 33, 35, 39, 41, 42, 47, 51, 57, 58, 63 or 65, e.g., from one or more of serotypes 6, 11, 16 and/or 18; Adenovirus including adenovirus serotype 36 (Ad-36). Examples of enterovirus include poliovirus, e.g., a type 1, type 2 and/or type 3 poliovirus; an EV71 enterovirus; a coxsackie A or B virus In some embodiments, the polypeptide encoded by the recombinant alphavirus replicon is an antigen derived from a virus which infects fish or other animals, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), land-locked salmon virus (LSV), atlantic salmon rotavirus (ASR), trout strawberry disease virus (TSD), coho salmon tumor virus (CSTV), or viral hemorrhagic septicemia virus (VHSV).

In some embodiments, the polypeptide encoded by the recombinant alphavirus replicon is an antigen derived from a fungus. Exemplary fungal antigens include, but are not limited to, antigens from any of *Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon*, and *Xylohypha*. In some embodiments, fungal antigens are be derived from any of *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*; or from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp., *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp., *Mucor* spp., *Absidia* spp., *Mortierella* spp., *Cunninghamella* spp., *Saksenaea* spp., *Alternaria* spp., *Curvularia* spp., *Helminthosporium* spp., *Fusarium* spp., *Aspergillus* spp., *Penicillium* spp., *Monolinia* spp., *Rhizoctonia* spp., *Paecilomyces* spp., *Pithomyces* spp., and *Cladosporium* spp.

In some embodiments, the polypeptide encoded by the recombinant alphavirus replicon is an antigen derived from a parasite. Exemplary parasites include, but are not limited to, those from the *Plasmodium* genus, such as *P. falciparum, P. vivax, P. malariae* or *P. ovale*. In some embodiments, the antigen elicits an immune response against a parasite from the Caligidae family, particularly those from the *Lepeophtheirus* and *Caligus* genera e.g., sea lice such as *Lepeophtheirus salmonis* or *Caligus rogercresseyi*.

In some embodiments, the polypeptide encoded by the recombinant alphavirus replicon is an antigen derived from an allergen. Exemplary allergens include, but are not limited to: pollen allergens (tree, herb, weed, and grass pollen allergens); insect or arachnid allergens (inhalant, saliva, and venom allergens, mite allergens, cockroach and midges allergens, hymenopthera venom allergens); animal hair and dandruff allergens (from e.g., dog, cat, horse, rat, mouse, etc.); and food allergens (e.g., a gliadin). Exemplary pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and *Sorghum*, the orders of Asterales and Urticales including herbs of the genera *Ambrosia, Artemisia*, and *Parietaria*. Other exemplary inhalation allergens are those from house dust mites of the genus *Dermatophagoides* and *Euroglyphus*, storage mite e.g., *Lepidoglyphys, Glycyphagus* and *Tyrophagus*, those from cockroaches, midges and fleas e.g., *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (Apidae), wasps (Vespidea), and ants (Formicoidae).

In some embodiments, the polypeptide encoded by the RNA or recombinant alphavirus replicon is an antigen derived from a tumor antigen. In some embodiments, the tumor antigen is selected from any one or more of the following, or portions thereof: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12; (b) mutated antigens, for example, p53, p21/Ras, CDK4, MUMI, caspase-8, CIA 0205, HLA-A2-R1701, beta catenin, TCR, BCR-abl, triosephosphate isomerase, KIA 0205, CDC-27, and LDLR-FUT; (c) over-expressed antigens, for example, mesothelin, livin, survivin, ICAM-1, galectin 4, galectin 9, proteinase 3, WT 1, carbonic anhydrase, aldolase A, PRAME, HER-2/neu, mammaglobin, alpha-fetoprotein, KSA, gastrin, telomerase catalytic protein, MUC-1, G-250, p53, granulocyte-macrophage colony-stimulating factor (GM-CSF), and carcinoembryonic antigen; (d) shared antigens, for example, melanoma-melanocyte differentiation antigens such as MART-1/Melan A, Gp100, MC1R, melanocyte-stimulating hormone receptor, tyrosinase, tyrosinase related protein-1/TRPI and tyrosinase related protein-2/TRP2; (e) prostate associated antigens such as PAP, PSA, PSMA, PSH-P1, PSM-P1, PSM-P2; (f) immunoglobulin idiotypes; (g) or any combinations thereof. In certain embodiments, tumor immunogens include, but are not limited to, pi 5, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29YBCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein cyclophilin C-associated protein), TAAL6, TAG72, TLP, TPS, or any combinations thereof.

In some embodiments, replicons are used to deliver an exogenous polypeptide to a subject. In some embodiments, the replicons encode, for example, and without limitation, a functional, therapeutic polypeptide to replace a mutated or missing polypeptide in the subject. In some embodiments, the replicons encode a polypeptide that inhibits or interferes with the function of an endogenous polypeptide in the subject. In some embodiments, the polypeptide encoded by the replicon is an exogenous polypeptide that provides therapeutic benefit to the subject. In some embodiments, the therapeutic benefit means the treatment of, reduced incidence of, alleviation of the symptoms of, or cure of a disease, condition, or disorder. In some embodiments, the polypeptide is an antigen. In some embodiments, replicons encode a polypeptide delivered for cosmetic purposes. In some embodiments, the polypeptide is delivered according to the compositions and methods of the disclosure (e.g., by a microneedle device). In some embodiments, the polypeptide includes any polypeptide found in nature, engineered polypeptides, chimeric polypeptides (e.g., containing fragments or portions from more than one source of polypeptide), and the like. The polypeptides and polypeptide encoded replicons disclosed herein can be of any suitable length. In some embodiments, the polypeptide contains less than about twenty amino acids (e.g., less than 20, 19, 18, 17, 16, 15, 14, 13, 12, 11, 10, or fewer amino acids); more than about 20 amino acids but less than about 50 amino acids; or a protein, containing more than about 50 amino acids. In some embodiments, the polypeptide contains about or more than about 100, 1000, 2000, 3000, 4000, 5000, 7500, 10000, 20000, or more amino acids.

In some embodiments, replicons encode a polypeptide for use in providing a therapeutic and/or cosmetic benefit to a subject. In some embodiments, the polypeptide for use in providing a therapeutic and/or cosmetic benefit includes enzymes, enzyme inhibitors, hormones, immunoglobulins such as natural, modified, or chimeric immunoglobulins or fragments thereof, lymphokines, cytokines, and chemokines. In some embodiments, polypeptides are derived from mammals (e.g., without limitation, human, dog, cat, monkey, sheep, goat, horse, cow, and the like), bacteria, viruses, fungi, or parasites. In some embodiments, the encoded polypeptide is derived from a human. In some embodiments, polypeptides are naturally occurring, modified from the natural state, chimeric proteins containing fragments of proteins from at least two different proteins, engineered proteins with enhanced function or activity, engineered proteins with decreased function or activity, or targeted to a specific compartment of a cell, e.g., cytoplasmic, membrane, or nucleus, or any combinations thereof. In some embodiments, the encoded polypeptide is human insulin useful for the treatment of diabetes, e.g., type I or type II diabetes.

Examples of polypeptides that are delivered, either directly as polypeptides or indirectly by delivering a recombinant alphavirus replicon or other polynucleotide encoding the polypeptide, include, but are not limited to: VEGF, VEGF-R1, VEGF-R2, VEGF-R3, Her-1, Her-2, Her-3, EGF-1, EGF-2, EGF-3, EGF-R, c-Met, ICOS, CD40L, LFA-1, OX40, TAC1-5, IgE, BAFF/BLys, TPO-R, CD2F-

10/SLAMF9, CD2, CD3, CD4, CD5, CD5L, CD6, CD8, CD9, CD14, CD19, CD20, CD22, CD23/Fc epsilon R2, DPPIV/CD26, CD27/TNFRSF7, CD28, CD30/TNFRSF8, CD31/PECAM-1, CD33, CD34, CD36/SR-B3, CD38, CD40, CD43, CD44, CD45, CD46, CD47, CD48/SLAMF2, CD52, CD55/DAF, CD58/LFA-3, CD59, CEACAM-1/CD66a, CD68, CD69, CD72, CD74, CD83, CD84, CD90/Thy1, C1q R1/CD93, CD94, CD95, CD97, EMMPRIN/CD147, DEP-1/CD148, CD151, CD155/PVR, CD160, CD163, CD164, CD200, CD200-R1, CD229/SLAMF3, TNFα, TRAIL, TRAIL-R1, TRAIL-R2, TRAIL-R3, TRAIL-R4, Complement Receptor 1, FGFa, Osteopontin, Vitronectin, alpha-2-macroglobulin, CCL1, CCL2, CCL3, CCL4, CCL5, CCL6/C10, CCL7, CXCL8, CXCL9, CXCL10, CCL11, CXCL11/Eotaxin, CXCL12, CCL13, CXCL13, CXCL14, CCL14, CCL15, CXCL16, CCL16, CCL17, CCL18, CCL19, CCL20, CCL21, CCL22, CCL24/Eotaxin-2, CCL26/Eotaxin-3, CCL27, CCL28, PDGF, TGFb, GM-CSF, SCF, p40, IL1a, IL1-R1, IL-1b, IL2, IL2-R, IL3, IL4, IL5, IL6, IL6-R, IL8, IL10, IL12, IL15, IL23, Fas, FasL, F10, 41BB, ACE, ACE-2, KGF, FGF-7, SCF, Netrin1, Netrin2, IFNa, IFNb, IFNg, ADAMS1, ADAMS5, ADAM8, ADAM9, ADAM10, ADAM12, ADAM15, TACE/ADAM17, ADAM19, ADAM33, ADAMTS1, ADAMTS4, ADAMTS5, ADAMTSL-1/Punctin, ALCAM, ALK-1, APRIL, Angiogenin, Amphiregulin, Angiopoietin 1, Angiopoietin 2, Angiopoietin 3, Angiopoietin 4, B7-1/CD80, B7-2/CD86, B7-H1, B7-H2, B7-H3, B7-H4, BACE-1, BACE-2, BAK, BCAM, BDNF, bNGF, bECGF, BMP1, BMP 2, BMP 3, BMP-3b/GDF-10, BMP 4, BMP 5, BMP 6, BMP 7, BMP8, BMP9, BMP10, BMP-15/GDF-9B, BMPR-1A/ALK-3, BMPR-1B/ALK-6, BMPR-2, CRP, E-Cadherin/Cadherin 1, N-Cadherin/Cadherin 2, P-Cadherin/Cadherin 3, Cadherin-4/R-Cadherin, VE-Cadherin/Cadherin 5, Cadherin 6, Cadherin 8, Cadherin 11, Cadherin 12, Cadherin 13, Cadherin 17, Cathepsin 1, Cathepsin 3, Cathepsin 6, Cathepsin A, Cathepsin B, Cathepsin C/DPPI, Cathepsin D, Cathepsin E, Cathepsin F, Cathepsin H, Cathepsin L, Cathepsin O, Cathepsin S, Cathepsin V, Cathepsin X/Z/P, LFA-3, GP2b3a, GH receptor, RSV F protein, CTLA-4, Integrin α4β1, Integrin α4β7, Lymphotoxin, Digoxin, RhoD, TNF-R family, Lymphotoxin a/b receptor, TL1A/TNFSF15, BAFF-R/TNFRSF13C, Fas/TNFRSF6, DR3/TNFRSF25, HVEM/TNFRSF14, TROY/TNFRSF19, CD40 Ligand/TNFSF5, BCMA/TNFRSF17, LIGHT/TNFSF14, 4-1BB/TNFRSF9, GITR/TNFRSF18, Osteoprotegerin/TNFRSF11B, RANK/TNFRSF11 A, TRANCE/RANKL/TNFSF11, 4-1BB Ligand/TNFSF9, TWEAK/TNFSF12, CD40 Ligand/TNFSF5, Fas Ligand/TNFSF6, RELT/TNFRSF19L, APRIL/TNFSF13, DcR3/TNFRSF6B, TNFR-1/TNFRSF1A, CD30 Ligand/TNFSF8, GITR Ligand/TNFSF18, TNFSF18, TAC1/TNFRSF13B, NGFR/TNFRSF16, OX40 Ligand/TNFSF4, TWEAK-R/TNFRSF12, DR6/TNFRSF21, Pro-TNF-alpha/TNFSF1-A, TNF-beta/TNFSF1B, PGRP-S, TNFR-2/TNFRSF1B, EDA-A2, EDAR, XEDAR, 4EBP1, 14-3-3 zeta, 53BP1, 2B4/SLAMF4, 8D6A, A2B5, Aminopeptidase LRAPIERAP2, A33, Aminopeptidase N/ANPEP, Aag, Aminopeptidase P2/XPNPEP2, ABCG2, Aminopeptidase P1/XPNPEP1, ACE-1, Aminopeptidase PILS/ARTS1, ACE-2, Amnionless, Actin, Amphiregulin, beta-Actin, Activin A, AMPK alpha 1, Activin AB, AMPK alpha 2, Activin B, AMPK beta 1, Activin C, AMPK beta 2, Activin R12A/ALK-2, Androgen R/NR3C4, Activin R1B/ALK-4, Angiogenic Activin R2A, Activin R2B, ADAM 10, Angiopoietin-like 1, Angiopoietin-like 2, Angiopoietin-like 3, Angiopoietin-like 4, Angiopoietin-like 7/CDT6, Angiostatin, Annexin A1/Annexin 1, Annexin A7, Annexin A10, Annexin V, Adiponectin/Acrp30, ANP, AEBSF, Aggrecan, APAF-1, Agrin, APC, AgRP, APE, AGTR-2, APJ, AIF, APLP-1, APLP-2, Akt1, Apolipoprotein A1, Akt2, Apolipoprotein B, Akt3, APP, Serum Albumin, ALCAM, ARC, ALK-1, Artemin, ALK-7, Arylsulfatase A/ARSA, Alkaline Phosphatase, ASAH2/N-acylsphingosine Amidohydrolase-2, alpha-2u Globulin, ASC, alpha-1-Acid Glycoprotein, ASGR1, alpha-Fetoprotein, ASK1, ALS, ATM, Ameloblastic ATRIP, AMICA/JAML, Aurora A, AMIGO, Aurora B, AMIGO2, Axin-1, AMIGO3, Axl, Aminoacylase/ACY1, Azurocidin/CAP37/HBP, Aminopeptidase A/ENPEP, B4GALT1, BIM, 6-Biotin-17-NAD, BLAME/SLAMF8, BLIMP1, Bik, BMI-1, Bad, Bag-1, BAK, BAMBI/NMA, BARD1, Bax, Bcl-10, Bcl-2, Bcl-2 related protein A1, Bcl-w, Bcl-x, BNIP3L, Bcl-xL, BOC, BOK, BPDE, Brachyury, B-Raf, beta IG-H3, Betacellulin, BRCA1, beta-Defensin 2, BRCA2, BID, BTLA, Biglycan, Bub-1, Bik-like Killer Protein, c-jun, c-Rel, C1qTNF1, C1qTNF4, C1qTNF5, Complement Component C1r, Complement Component C1s, Complement Component C2, Complement Component C3a, Complement Component C3d, Complement Component C5a, CDC2, CDC25A, CDC25B, CDCP1, CDO, CDX4, CEACAM-6, Cerberus 1, CFTR, Calbindin D, Calcineurin A, Chem R23, Calcineurin B, Chemerin, CaM Kinase 2, Chitinase 3-like 1, Chitotriosidase/CHIT1, Cannabinoid R1, Chk1, Cannabinoid R2/CB2/CNR2, Chk2, CARJNR1I3, CHL-1/L1CAM-2, Carbonic Anhydrase I, Choline Acetyltransferase/ChAT, Carbonic Anhydrase II, Chondrolectin, Carbonic Anhydrase III, Chordin, Carbonic Anhydrase IV, Chordin-Like 1, Carbonic Anhydrase VA, Chordin-Like 2, Carbonic Anhydrase VB, Carbonic Anhydrase VI, CINC-1, Carbonic Anhydrase VII, CINC-2, Carbonic Anhydrase VIII, CINC-3, Claspin, Carbonic Anhydrase IX, Claudin-6, Carbonic Anhydrase X, CLCN5, Carbonic Anhydrase XII, CLEC-1, Carbonic Anhydrase XIII, CLEC-2, Carbonic Anhydrase XIV, CLECSF-13/CLEC-4F, CLECSF8, Carboxypeptidase A1/CPA1, CLF-1, Carboxypeptidase A2, CL-Pl/COLEC12, Carboxypeptidase A4, Clusterin, Carboxypeptidase B1, Clusterin-like 1, Carboxypeptidase E/CPE, CMG-2, Carboxypeptidase X1, CMV UL146, Cardiotrophin-1, CMV UL147, Camosine Dipeptidase 1, CNP, Caronte, CNTF, CART, CNTF R alpha, Coagulation Factor II/Thrombin, Caspase-1, Coagulation Factor III/Tissue Factor, Caspase-2, Coagulation Factor VII, Caspase-3, Coagulation Factor X, Caspase-4, Coagulation Factor XI, Caspase-6, Coagulation Factor XIV/Protein C, Caspase-7, COCO, Caspase-8, Cohesin, Caspase-9, Collagen I, Caspase-10, Collagen II, Caspase-12, Collagen IV, Caspase-13, Common gamma Chain/IL-2 R gamma, Caspase Peptide Inhibitors, COMP/Thrombospondin-5, Catalase, Complement Component C1rLP, beta-Catenin, Complement Component C1qA, Complement Component C1qC, Complement Factor D, Complement Factor I, Complement MASP3, Connexin 43, Contactin-1, Contactin-2/TAG1, Contactin-4, Contactin-5, Corin, Cornulin, CORS26/C1qTNF3, COUP-TF I/NR2F1, CBP, COUP-TF II/NR2F2, CCI, COX-1, CCKAR, COX-2, CRACC/SLAMF7, CCR1, C-Reactive Protein, CCR2, Creatine Kinase, Muscle/CKMM, CCR3, CCR4, CREB, CCR5, CREG, CCR6, CRELD1, CCR7, CRELD2, CCR8, CRHBP, CCR9, CRHR-1, CCR10, CRIM1, Cripto, CRISP-2, CRISP-3, Crossveinless-2, CRTAM, CRTH-2, CRY1, Cryptic, CSB/ERCC6, CTGF/CCN2, CTLA-4, Cubilin, CX3CR1, CXADR, CD27 LigandVTNFSF7, CXCR3, CXCR4, CXCR5, CD30 Ligand/TNFSFδ, CXCR6, Cyclophilin A, Cyr61/CCN1, Cystatin A, Cystatin B, Cystatin C, Cystatin D, Cystatin E/M, Cystatin F, Cystatin H, Cystatin H2, Cystatin S, Cystatin SA, Cystatin SN, Cytochrome c, Apocytochrome c, Holocytochrome c, Cytokeratin 8, Cytokeratin 14, Cytokeratin 19, Cytonin, D6, DISP1, DAN, Dkk-1, DANCE, Dkk-2, DARPP-32, Dkk-3, DAX1/NROB1, Dkk-4, DCC, DLEC, CLEC4A, DLL1, DCAR, DLJL4, DcR3/TNFRSF6B, DC-SIGN, DNA Ligase IV, DC-SIGNR/CD299, DNA Polymerase beta, DcTRAIL-R1/TNFRSF23, DNAM-1, DcTRAIL-R2/TNFRSF22, DNA-PKcs, DDR1, DNER, DDR2, Dopa Decarboxylase/DDC, DEC-205, DPCR-1, Decapentaplegic, DPP6, Decorin, DPPA4, Dectin-1/CLECyA, DPPA5lESG1, Dectin-2/CLEC6A, DPPI-UQPP/DPP7, Desert Hedgehog, Desmin, Desmoglein-1, DSCAM, Desmoglein-2, DSCAM-L1, Desmoglein-3, DSPG3, Dishevelled-1, Dtk, Dishevelled-3, Dynamin, EAR2/NR2F6, EphA5, ECE-1, EphA6, ECE-2, EphA7, ECF-L/CHI3L3, EphA8, ECM-I, EphB1, Ecotin, EphB2, EDA, EphB3, EDA-A2, EphB4, EDAR, EphB6, EDG-1, EDG-5, Ephrin-A1, EDG-8, Ephrin-A2, eEF-2, Ephrin-A3, Ephrin-A4, Ephrin-A5, EGR1, Ephrin-B, EG-VEGF/PK1, Ephrin-B1, eIF2 alpha, Ephrin-B2, eIF4E, Ephrin-B3, EIk-1, Epigen, EMAP-II, Epimorphin/Syntaxin 2Epiregulin, CXCL5/ENA, EPR-1/Xa Receptor, Endocan, ErbB2, Endoglin/CD105, ErbB3, Endoglycan, ErbB4, Endonuclease III, ERCCl, Endonuclease IV, ERCC3, Endonuclease V, Endonuclease VIII, ERK1, Endorepellin/Perlecan, ERK2, Endostatin, ERK3, Endothelin-1, ERK5/BMK1, Engrailed-2, ERR alpha/NR3B1, EN-RAGE, ERR beta/NR3B2, Enteropeptidase/Enterokinase, ERR gamma/NR3B3, Erythropoietin, Erythropoietin R, CCL26/Eotaxin-3, ESAM, EpCAM/TROP-1, ER alpha/NR3A1, EPCR, ER beta/NR3A2, Eph, Exonuclease III, EphA1, Exostosin-like 2/EXTL2, EphA2, Exostosin-like 3/EXTL3, EphA3, FABP1, FGF-BP, FABP2, FGF R1, FGF R2, FGF R3, FGF R4, FABP3, FABP4, FABP5, FABP7, FABP9, FGF R5, Complement Factor B, FHR5, FAM3A, Fibronectin, FAM3B, Ficolin-2, FAM3C, Ficolin-3, FAM3D, FITC, Fibroblast Activation Protein alpha/FAP, FKBP38, Fas/TNFRSF6, Flap, Fas Ligand/TNFSF6, FLIP, FATP4, FLRG, FATP4, FLRT1, FATP5, FLRT2, Fc gamma RUCD64, FLRT3, Fc gamma RIIB/CD32b, Flt-3, Fc gamma RIIC/CD32c, Flt-3 Ligand, Fc gamma RIIA/CD32a, Follistatin, Fc gamma RIII/CD16, Follistatin-like 1, FcRH1/IRTA5, FosB/GOS3, FcRH2/IRTA4, FoxD3, FcRH4/IRTA1, FoxJ1, FcRH5/IRTA2, FoxP3, Fc Receptor-like 3/CD16-2, Fpg, FEN-1, FPR1, Fetuin A, FPRL1, Fetuin B, FPRL2, FGF acidic, CX3CL1/Fractalkine, FGF basic, Frizzled-1, FGF-3, Frizzled-2, FGF-4, Frizzled-3, FGF-5, Frizzled-4, FGF-6, Frizzled-5, FGF-8, Frizzled-6, FGF-9, Frizzled-7, FGF-10, Frizzled-8, FGF-11, Frizzled-9, FGF-12, Frk, FGF-13, sFRP-1, FGF-16, sFRP-2, FGF-17, sFRP-3, FGF-19, sFRP-4, FGF-20, Furin, FGF-21, FXR/NR1H4, FGF-22, Fyπ, FGF-23, G9a/EHMT2, GFR alpha-3/GDNF R alpha-3, GABA-A-R alpha 1, GFR alpha-4/GDNF R alpha-4, GABA-A-R alpha 2, GITR/TNFRSF18, GABA-A-R alpha 4, GITR Ligand/TNFSF 18, GABA-A-R alpha 5, GLI-1, GABA-A-R alpha 6, GLI-2, GABA-A-R beta 1, GLP/EHMT1, GABA-A-R beta 2, GLP-I R, GABA-A-R beta 3, Glucagon, GABA-A-R gamma 2, Glucosamine (N-acetyl)-6-SulfataselGNS, GABA-B-R2, GluR1, GAD1/GAD67, GluR2/3, GAD2/GAD65, GluR2, GADD45 alpha, GluR3, GADD45 beta, Glut1, GADD45 gamma, Glut2, Galectin-1, Glut3, Galectin-2, Glut4, Galecrin-3, Glut5, Galectin-3 BP, Glutaredoxin 1, Galectin-4, Glycine R, Galectin-7, Glycophorin A, Galectin-8, Glypican 5, Galectin-9, Glypican 3, GalNAc4S-6ST, Glypican 5, GAP-43, Glypican 6, GAPDH, GM-CSF, Gasl, GM-CSF R alpha, Gas6, GMF-beta, GASP-1/WFIKKNRP, gp130, GASP-2/WFIKKN, Glycogen Phosphorylase BB/GPBB, GATA-1, GPR15, GATA-2, GPR39, GATA-3, GPVI, GATA-4, GR/NR3C1, GATA-5, Gr-1/Ly-6G, GATA-6, Granulysin, GBL, Granzyme A, GCNF/NR6A1, Granzyme B, CXCL6/GCP-2, Granzyme D, G-CSF, Granzyme G, G-CSF R, Granzyme H, GDF-1, GRASP, GDF-3, GRB2, GDF-5, Gremlin, GDF-6, GRO, GDF-7, CXCL1/GRO alpha, GDF-8, CXCL2/GRO beta, GDF-9, CXCL3/GRO gamma, GDF-11, Growth Hormone, GDF-15, Growth Hormone R, GDNF, GRP75/HSPA9B, GFAP, GSK-3 alpha/beta, GFI-1, GSK-3 alpha, GFR alpha-1/GDNF R alpha-1, GSK-3 beta, GFR alpha-2/GDNF R alpha-2, EZFIT, H2AX, H60, HM74A, HAI-1, HMGA2, HAI-2, HMGB1, HAI-2A, TCF-2/HNF-1 beta, HAI-2B, HNF-3 beta/FoxA2, HAND1, HNF-4 alpha/NR2A 1, HAPLN1, HNF-4 gamma/NR2A2, Airway Trypsin-like Protease/HAT, HO-1/HMOX1/HSP32, HB-EGF, HO-2/HMOX2, CCL14a/HCC-1, HPRG, CCL14b/HCC-3, Hrk, CCL16/HCC-4, HRP-1, alpha HCG, HS6ST2, Hck, HSD-1, HCR/CRAM-A/B, HSD-2, HDGF, HSP10/EPF, Hemoglobin, HSP27, Hepassocin, HSP60, HES-1, HSP70, HES-4, HSP90, HGF, HTRA, HGF Activator, HTRA 1/PRSS11, HGF R, HTRA2/Omi, HIF-1 alpha, HVEM/TNFRSF14, HIF-2 alpha, Hyaluronan, HIN-1/Secretoglobulin 3A1, Hip, CCL1/1-309/TCA-3, IL-10, cIAP, IL-10 R alpha, cIAP-2, HIAP-2, IL-10 R beta, cIAP-2/HIAP-1, IL-11, IBSP/Sialoprotein II, IL-11 R alpha, ICAM-1/CD54, IL-12, ICAM-2/CD102, IL-12/IL-23, ICAM-3/CD50, IL-12 R beta 1, ICAM-5, IL-12 R beta 2, ICAT, IL-13, ICOS, IL-13 R alpha 1, Iduronate 2-Sulfatase/IDS, IL-13 R alpha 2, IFN5, IL-15, EFN-alpha, IL-15 R alpha, DFN-alpha 1, IL-16, IFN-alpha 2, IL-17, IFN-alpha 4b, IL-17 R, IFN-alpha A1, IL-17 RC, IFN-alpha B2, IL-17 RD, IFN-alpha C, IL-17B, EFN-alpha D, IL-17B R, IFN-alpha F, IL-17C, IFN-alpha G, IL-17D, IFN-alpha H2, IL-17E, IFN-alpha 1, IL-17F, IFN-alpha J1, IL-18/IL-1F4, IFN-alpha K, IFN-alpha WA, IL-18 BPc, IFN-alpha/beta R1, IL-18 BPd, IFN-alpha/beta R2, IFN-beta, EFN-gamma, IL-19, IFN-gamma R1, EL-20, IFN-gamma R2, IL-20 R alpha, IFN-omega, IL-20 R beta, IgE, IL-21, IGFBP-I, IL-21 R5, IGFBP-2, IL-22, IGFBP-3, IL-22 R, IGFBP-4, IL-22BP, IGFBP-5, IL-23, IGFBP-6, IL-23 R5, IGFBP-L1, IL-24, IL-26/AK155, IGFBP-rP10, IL-27, IGF-1, IL-28A, IGF-1 R, IL-28B, IGF-II, IL-29/IFN-lambda 1, IGF-II R, IL-31, IgG5, IL-31 RA5, IgM5, IL-32 alpha, IGSF2, IL-33, IGSF4A/SynCAM, ILT2/CD85J, IGSF4B, JLT3/CD8Sk, IGSF8, ILT4/CD85d, IgY5, ILT5/CD85a, BcB-beta, ILT6/CD85e, IKK alpha, Indian Hedgehog, IKK epsilon, INSRR, DCK gamma, Insulin, IL-I alpha/IL-1F1, Insulin R/CD220, Proinsulin, IL-lra/IL-1F3, Insulysin/IDE, IL-1F5/FIL1 delta, Integrin alpha 2/CD49b, IL-1F6/FIL1 epsilon, Integrin alpha 3/CD49c, IL-1F7/FIL1 zeta, Integrin alpha 3 beta DVLA-3, IL-1F8/FIL1 eta, Integrin alpha 4/CD49d, IL-1F9, Integrin alpha 5/CD49e, IL-1F10/IL-1HY2, Integrin alpha 5 beta 1, IL-1 RI5, Integrin alpha 6/CD49f, IL-1 RII, Integrin alpha 7, IL-1 R3/IL-1 R AcP, Integrin alpha 9, IL-1 R4/ST2, Integrin alpha E/CD103, IL-1 R6/IL-1 R rp2, Integrin alpha L/CD1 Ia, IL-I R8, Integrin alpha L beta 2, IL-I R9, Integrin alpha M, Integrin alpha M beta 2, IL-2 R alpha, Integrin alpha V/CD51, IL-2 R beta, Integrin alpha V beta 5, IL-3, Integrin alpha V beta 3, IL-3 R alpha, Integrin alpha V beta 6, IL-3 R beta, Integrin alpha X/CD1 Ic, IL-4, Integrin beta 1/CD29, IL-4 R, Integrin beta 2/CD18, IL-5, Integrin beta 3/CD61, IL-5 R alpha, Integrin beta 5, IL-6, Integrin beta 6, IL-6 R, Integrin beta 7, IL-7, CXCL110/IP-10/CRG-2, IL-7 R alpha/CD127, IRAK1, CXCR1/IL-8 RA, IRAK4, CXCR2/IL-8 RB, IRS-1, CXCL8/IL-8, Islet-1, IL-9, CXCL11/I-TAC, IL-9 R, Jagged 1, JAM-4/IGSF5, Jagged 2, JNK, JAM-A, JNK1/JNK2, JAM-B/VE-JAM, JNK1, JAM-C, JNK2, Kininogen, Kallikrein 3/PSA, Kininostatin, Kallikrein 4, KIR/CD158, Kallikrein 5, KIR2DL1, Kallikrein 6/Neurosin, KIR2DL3, Kallikrein 7, KIR2DL4/CD158d, Kallikrein 8/Neuropsin, KIR2DS4, Kallikrein 9, KIR3DL1, Plasma Kallikrein/KLKB1, KIR3DL2, Kallikrein 10, Kirrel2, Kallikrein 11, KLF4, Kallikrein 12, KLF5, Kallikrein 13, KLF6, Kallikrein 14, Klotho, Kallikrein 15, Klotho beta, Keap1, Kremen-1, Kel1, Kremen-2, KGF/FGF-7, LAG-3, LINGO-2, LAIR1, Lipin 2, LAIR2, Lipocalin-1, Laminin alpha 4, Lipocalin-2/NGAL, Laminin gamma 1, 5-Lipoxygenase, Laminin 1, LXR alpha/NR1H3, Laminin S, LXRbeta/NR1H2, Laminin-1, Livin, Laminin-5, LLX5, LAMPS, CD300A, Langerin, LMIR2/CD300c, LAR, LMIR3/CD300LF, Latexin, LMIRS/CD300LB, Layilin, LMIR6/CD300LE, LBP5, LMO2, LDL R5, LOX-1/SR-E1, LECT2, LRH-1/NR5A2, LEDGF5, LRIG1, Lefty, LRIG3, Lefty-1, LRP-1, Lefty-A, LRP-6, Legumain, LSECtrn/CLEC4G, Leptin, Lumican, Leptin R, CXCL15/Lungkine, Leukotriene B4, Leukotriene B4 R1, Lymphotoxin, LIF, Lymphotoxin beta/TNFSF3, LIF R alpha, Lymphotoxin beta R/TNFRSF3, LIGHT/TNFSF14, Lyn, Limitin, Lyp, LIMPII/SR-B2, Lysyl Oxidase Homolog 2, LIN-28, LYVE-1, LINGO-1, alpha 2-Macroglobulin, CXCL9/MIG, MAD2L1, Mimecan, MAdCAM-1, Mindin, R/NR3C2, MafF, MafB, CCL3L1/MIP-1 alpha Isoform LD78 beta, MafG, CCL3/MIP-1 alpha, MafK, CCL4L1/LAG-1, MAG/Siglec-4a, CCIA/MIP-1 beta, MANF, CCL15/MIP-1 delta, MAP2, CCL9/10/MIP-1 gamma, MAPK, MIP-2, Marapsin/Pancreasin, CCL19/MIP-3 beta, MARCKS, CCL20/MIP-3 alpha, MARCO, MIP-1, Mashl, MIP-II, MIP-UI, Matrilin-3, MIS/AMH, Matrilin-4, MIS RII, Matriptase/ST14, MIXL1, MBL, MKK3/MKK6, MBL-2, MKK3, Melanocortin 3R/MC3R, MKK4, MCAM/CD146, MKK6, MCK-2, MKK7, Mcl-1, MKP-3, MCP-6, MLH-1, CCL2/MCP-1, MLK4 alpha, MCP-11, MMP, CCL8/MCP-2, MMP-1, CCL7/MCP-3/MARC, MMP-2, CCL13/MCP-4, MMP-3, CCL12/MCP-5, MMP-7, M-CSF, MMP-8, M-CSF R, MMP-9, MCV-type π, MMP-10, MD-1, MMP-11, MD-2, MMP-12, CCL22/MDC, MMP-13, MDL-1/CLEC5A, MMP-14, MDM2, MMP-15, MEA-1, MMP-16/MT3-MMP, MEK1/MEK2, MMP-24/MT5-MMP, MEK1, MMP-25/MT6-MMP, MEK2, MMP-26, Melusin, MMR, MEPE, MOG, Meprin alpha, CCL23/MPIF-1, Meprin beta, M-Ras/R-Ras3, Mer, Mrel 1, Mesothelin, MRP1, Meteorin, MSK1/MSK2, Methionine Aminopeptidase 1, MSK1, Methionine Aminopeptidase, MSK2, Methionine Aminopeptidase 2, MSP, MFG-E8, MSP R/Ron, MFRP, Mug, MgcRacGAP, MULT-1, MGL2, Musashi-1, MGMT, Musashi-2, MIA, MuSK, MICA, MutY DNA Glycosylase, MtCB, MyD88, MICL/CLEC12A, Myeloperoxidase, beta 2 Microglobulin, Myocardin, Midkine, Myocilin, MIF, Myoglobin, NAIP, NGFI-B gamma/NR4A3, Nanog, NgR2/NgRH1, CXCL7/NAP-2, NgR3/NgRH2, Nbsl, Nidogen-1/Entactin, NCAM-1/CD56, Nidogen-2, NCAM-L1, Nitric Oxide, Nectin-1, Nitrotyrosine, Nectin-2/CD112, NKG2A, Nectin-3, NKG2C, Nectin-4, NKG2D, Neogenin, NKp30, Neprily sin/CD 10, NKp44, Neprilysin-2/MMEL1/MMEL2, NKp46/NCR1 Nestin, NKp80/KLRF1, NETO2, NKX2.5, Netrin-1, NMDA R, NR1 Subunit, Netrin-2, NMDA R, NR2A Subunit, Netrin-4, NMDA R, NR2B Subunit, Netrin-G1a, NMDA R, NR2C Subunit, Netrin-G2a, Neuregulin-1/NRG1, Nodal, Neuregulin-3/NRG3, Noggin, Neuritin, Nogo Receptor, NeuroD1, Nogo-A, Neurofascin, NOMO, Neurogenin-1, Nope, Neurogenin-2, Norrin, Neurogenin-3, eNOS, Neurolysin, iNOS, Neurophysin II, nNOS, Neuropilin-1, Notch-1, Neuropilin-2, Notch-2, Neuropoietin, Notch-3, Neurotrimin, Notch-4, Neurturin, NOV/CCN3, NFAM1, NRAGE, NF-H, NrCAM, NFkB1, NRL, NFkB2, NT-3, NF-L, NT-4, NF-M, NTB-A/SLAMF6, NG2/MCSP, NTH1, NGF R/TNFRSF16, Nucleostemin, beta-NGF, Nurr-1/NR4A2, NGFI-B alpha/NR4A1, OAS2, Orexin B, OBCAM, OSCAR, OCAM, OSF-2/Periostin, OCIL/CLEC2d, Oncostatin M/OSM, OCILRP2/CLEC2i, OSM R beta, Oct-3/4, Osteoactivin/GPNMB, OGG1, Osteoadherin, Osteocalcin, Olig1, Osteocrin, Olig2, Osteopontin, Olig3, Osteoprotegerin/TNFRSF11B, Otx2, OV-6, OMgp, OX40/TNFRSF4, Opticin, OX40 Ligand/TNFSF4, Orexin A, RACK1, Ret, Rad1, REV-ERB alpha/NR1D1, Rad17, REV-ERB beta/NR1D2, Rad51, Rex-1, Rae-1, RGM-A, Rae-1 alpha, RGM-B, Rae-1 beta, RGM-C, Rae-1 delta, Rheb, Rae-1 epsilon, Ribosomal Protein S6, Rae-1 gamma, RIP1, Raf-1, ROBO1, RAGE, ROBO2, RalA/RalB, ROBO3, RaIA, ROBO4, RaIB, ROR/NR1F1-3, RANK/TNFRSF11A, ROR alpha/NRIF1, CCL5/RANTES, ROR gamma/NR1F3, Rapl A/B, RTK-like Orphan Receptor 1/ROR1, RAR alpha/NR1B1, RTK-like Orphan Receptor 2/ROR2, RAR beta/NR1B2, RP105, RAR gamma/N1IB3, RPA2, Ras, RSK, RBP4, RSK1/RSK2, RECK, RSK1, Reg 2/PAP, RSK2, Reg I, RSK3, Reg IL RSK4, Reg III, R-Spondin 1, Reg HIa, R-Spondin 2, Reg IV, R-Spondin 3, Relaxin-1, RUNX1/CBFA2, Relaxin-2, RUNX2/CBFA1, Relaxin-3, RUNX3/CBFA3, RELM alpha, RXR alpha/NR2B1, RELM beta, RXR beta/NR2B2, RELT/TNFRSF19L, RXR gamma/NR2B3, Resistin, SLITRK5, S100A8, SLPI, S100A9, SMAC/Diablo, S100B, Smad1, S100P, Smad2, SALL1, Smad3, delta-Sarcoglycan, Smad4, Sca-1/Ly6, Smad5, SCD-1, Smad7, SCF, Smad6, SCF R/c-kit, SMC1, SCGF, alpha-Smooth Muscle Actin, SCL, SMUG1, SCP3/SYCP3, Snail, CXCL12/SDF-1, Sodium Calcium Exchanger 1, SDNSF/MCFD2, Soggy-1, alpha-Secretase, Sonic Hedgehog, gamma-Secretase, SorCS1, beta-Secretase, SorCS3, E-Selectin, Sortilin, L-Selectin, SOST, P-Selectin, SOX1, Semaphorin 3A, SOX2, Semaphorin 3C, SOX3, Semaphorin 3E, SOX7, Semaphorin 3F, SOX9, Semaphorin 6A, SOX10, Semaphorin 6B, SOX17, Semaphorin 6C, SOX21 Semaphorin 6D, SPARC, Semaphorin 7A, SPARC-like 1, Separase, SP-D, Spinesin, Serpin A1, F-Spondin, Serpin A3, SR-AUMSR, Serpin A4/Kallistatin, Src, Serpin A5/Protein C Inhibitor, SREC-I/SR-F1, Serpin A8/Angiotensinogen, SREC-II, Serpin B5, SSEA-1, Serpin C1/Antithrombin-III, SSEA-3, Serpin D1/Heparin Cofactor II, SSEA-4, Serpin E1/PAI-1, ST7/LRP12, Serpin E2, Stabilin-1, Serpin F1, Stabilin-2, Serpin F2, Stanniocalcin 1, Serpin G1/C1 Inhibitor, Stanniocalcin 2, Serpin 12, STAT1, Serum Amyloid A1, STAT2, SF-1/NR5A1, STAT3, SGK, STAT4, SHBG, STAT5a/b, SHIP, STAT5a, SHP/NROB2, STAT5b, SHP-1, STAT6, SHP-2, VE-Statin, SIGIRR, Stella/Dppa3, Siglec-2/CD22, STRO-1, Siglec-3/CD33, Substance P, Siglec-5, Sulfamidase/SGSH, Siglec-6, Sulfatase Modifying Factor 1/SUMF1, Siglec-7, Sulfatase Modifying Factor 2/SUMF2, Siglec-9, SUMO1, Siglec-10, SUMO2/3/4, Siglec-11, SUMO3, Siglec-F, Superoxide Dismutase, SIGNR1/CD209, Superoxide Dismutase-1/Cu-Zn SOD, SIGNR4, Superoxide Dismutase-2/Mn-SOD, SIRP beta 1, Superoxide Dismutase-3/EC-SOD, SKI, Survivin, SLAM/CD150, Synapsin 1, Sleeping Beauty Transposase, Syndecan-1/CD138, Slit3, Syndecan-2, SLITRK1, Syndecan-3, SLITRK2, Syndecan-4, SLITRK4, TACI/TNFRSF13B, TMEFF 1/Tomoregulin-1, TAO2, TMEFF2, TAPP1, TNF-alphaA/TNFSF1A, CCL17/TARC, TNF-beta/TNFSF1B, Tau, TNFRI/TNFRSF1A, TC21/R-Ras2, TNF RIL/TNFRSF1B, TCAM-1, TOR, TCCR/WSX-1, TP-1, TC-PTP, TP63/TP73L, TDG, TR, CCJL25/TECK, TR alpha/NR1A1, Tenascin C, TR beta 1/NR1A2, Tenascin R, TR2/NR2C1, TER-119, TR4/

NR2C2, TERT, TRA-1-85, Testican 1/SPOCK1, TRADD, Testican 2/SPOCK2, TRAF-1, Testican 3/SPOCK3, TRAF-2, TFPI, TRAF-3, TFPI-2, TRAF-4, TGF-alpha, TRAF-6, TGF-beta, TRAIL/TNFSF10, TGF-beta 1, TRAIL R1/TNFRSF10A, LAP, TRAIL R2/TNFRSF10B, Latent TGF-beta 1, TRAIL R3/TNFRSF10C, TGF-beta 1.2, TRAIL R4/TNFRSFIOD, TGF-beta 2, TRANCE/TNFSF11, TGF-beta 3, Transferrin R, TGF-beta 5, Apo-Transferrin, Latent TGF-beta bpl, Holo-Transferrin, Latent TGF-beta bp2, Trappin-2/Elafin, Latent TGF-beta bp4, TREM-1, TGF-beta RI/ALK-5, TREM-2, TGF-beta RII, TREM-3, TGF-beta RIIb, TREML1/TLT-1, TGF-beta RIII, TRF-1, Thermolysin, TRF-2, Thioredoxin-1, TRH-degrading Ectoenzyrne/TRHDE, Thioredoxin-2, TRIMS, Thioredoxin-80, Tripeptidyl-Peptidase 1, Thioredoxin-like 5/TRP14, TrkA, THOP1, TrkB, Thrombomodulin/CD141, TrkC, Thrombopoietin, TROP-2, Thrombopoietin R, Troponin I Peptide 3, Thrombospondin-1, Troponin T, Thrombospondin-2, TROY/TNFRSF19, Thrombospondin-4, Trypsin 1, Thymopoietin, Trypsin 2/PRSS2, Thymus Chemokine-1, Trypsin 3/PRSS3, Tie-1, Tryptase-5/Prss32, Tie-2, Tryptase alpha/TPS1, TIM-1/KIM-1/HAVCR, Tryptase beta-1/MCPT-7, TIM-2, Tryptase beta-2/TPSB2, TIM-3, Tryptase epsilon/BSSP-4, TIM-4, Tryptase gamma-1/TPSG1, TIM-5, Tryptophan Hydroxylase, TIM-6, TSC22, TIMP-1, TSG, TIMP-2, TSG-6, TIMP-3, TSK, TIMP-4, TSLP, TL1A/TNFSF15, TSLP R, TLR1, TSP50, TLR2, beta-III Tubulin, TLR3, TWEAK/TNFSF12, TLR4, TWEAK R/TNFRSF 12, TLR5, Tyk2, TLR6, TLR9, Tyrosine Hydroxylase, TLX/NR2E1, Ubiquitin, UNC5H3, Ugi, UNC5H4, UGRP1, UNG, ULBP-1, uPA, ULBP-2, uPAR, ULBP-3, URB, UNC5H1, UVDE, UNC5H2, Vanilloid R1, VEGF R, VASA, VEGF R1/Flt-1, Vasohibin, VEGF R2/KDR/Flk-1, Vasorin, VEGF R3/Flt-4, Vasostatin, Versican, Vav-1, VG5Q, VCAM-1, VHR, VDR/NR1I1, Vimentin, VEGF, Vitronectin, VEGF-B, VLDLR, VEGF-C, vWF-A2, VEGF-D, Synuclein-alpha, Ku70, WASP, Wnt-7b, WIF-1, Wnt-8a WISP-1/CCN4, Wnt-8b, WNK1, Wnt-9a, Wnt-1, Wnt-9b, Wnt-3a, Wnt-10a, Wnt-4, Wnt-5a, Wnt-11, Wnt-5b, wnvNS3, Wnt7a, XCR1, XPE/DDB1, XEDAR, XPE/DDB2, Xg, XPF, XIAP, XPG, XPA, XPV, XPD, XRCC1, Yes, YY1, EphA4.

In some embodiments, selected polypeptides include any number of ion-channels, including: 5-hydroxytryptamine 3 receptor B subunit; 5-hydroxytryptamine 3 receptor precursor; 5-hydroxytryptamine receptor 3 subunit C; AAD 14 protein; Acetylcholine receptor protein, alpha subunit precursor; Acetylcholine receptor protein, beta subunit precursor; Acetylcholine receptor protein, delta subunit precursor; Acetylcholine receptor protein, epsilon subunit precursor; Acetylcholine receptor protein, gamma subunit precursor; Acid sensing ion channel 3 splice variant b; Acid sensing ion channel 3 splice variant c; Acid sensing ion channel 4; ADP-ribose pyrophosphatase, mitochondrial precursor; AlphalA-voltage-dependent calcium channel; Amiloride-sensitive cation channel 1, neuronal; Amiloride-sensitive cation channel 2, neuronal; Amiloride-sensitive cation channel 4, isoform 2; Amiloride-sensitive sodium channel; Amiloride-sensitive sodium channel alpha-subunit; Amiloride-sensitive sodium channel beta-subunit; Amiloride-sensitive sodium channel delta-subunit; Amiloride-sensitive sodium channel gamma-subunit; Annexin A7; Apical-like protein; ATP-sensitive inward rectifier potassium channel 1; ATP-sensitive inward rectifier potassium channel 10; ATP-sensitive inward rectifier potassium channel 11; ATP-sensitive inward rectifier potassium channel 14; ATP-sensitive inward rectifier potassium channel 15; ATP-sensitive inward rectifier potassium channel 8; Calcium channel alpha12.2 subunit; Calcium channel alpha IE subunit, delta19 delta40 delta46 splice variant; Calcium-activated potassium channel alpha subunit 1; Calcium-activated potassium channel beta subunit 1; Calcium-activated potassium channel beta subunit 2; Calcium-activated potassium channel beta subunit 3; Calcium-dependent chloride channel-1; Cation channel TRPM4B; CDNA FLJ90453 fis, clone NT2RP3001542, highly similar to Potassium channel tetramerisation domain containing 6; CDNA FLJ90663 fis, clone PLACE1 005031, highly similar to Chloride intracellular channel protein 5; CGMP-gated cation channel beta subunit; Chloride channel protein; Chloride channel protein 2; Chloride channel protein 3; Chloride channel protein 4; Chloride channel protein 5; Chloride channel protein 6; Chloride channel protein CIC-Ka; Chloride channel protein CIC-Kb; Chloride channel protein, skeletal muscle; Chloride intracellular channel 6; Chloride intracellular channel protein 3; Chloride intracellular channel protein 4; Chloride intracellular channel protein 5; CHRNA3 protein; Clcn3e protein; CLCNKB protein; CNGA4 protein; Cullin-5; Cyclic-GMP gated potassium channel; Cyclic-nucleotide-gated cation channel 4; Cyclic-nucleotide-gated cation channel alpha 3; Cyclic-nucleotide-gated cation channel beta 3; Cyclic-nucleotide-gated olfactory channel; Cystic fibrosis transmembrane conductance regulator; Cytochrome B-245 heavy chain; Dihydropyridine-sensitive L-type, calcium channel alpha-2/delta subunits precursor; FXYD domain-containing ion transport regulator 3 precursor; FXYD domain-containing ion transport regulator 5 precursor; FXYD domain-containing ion transport regulator 6 precursor; FXYD domain-containing ion transport regulator 7; FXYD domain-containing ion transport regulator 8 precursor; G protein-activated inward rectifier potassium channel 1; G protein-activated inward rectifier potassium channel 2; G protein-activated inward rectifier potassium channel 3; G protein-activated inward rectifier potassium channel 4; Gamma-aminobutyric-acid receptor alpha-1 subunit precursor; Gamma-aminobutyric-acid receptor alpha-2 subunit precursor; Gamma-aminobutyric-acid receptor alpha-3 subunit precursor; Gamma-aminobutyric-acid receptor alpha-4 subunit precursor; Gamma-aminobutyric-acid receptor alpha-5 subunit precursor; Gamma-aminobutyric-acid receptor alpha-6 subunit precursor; Gamma-aminobutyric-acid receptor beta-1 subunit precursor; Gamma-aminobutyric-acid receptor beta-2 subunit precursor; Gamma-aminobutyric-acid receptor beta-3 subunit precursor; Gamma-aminobutyric-acid receptor delta subunit precursor; Gamma-aminobutyric-acid receptor epsilon subunit precursor; Gamma-aminobutyric-acid receptor gamma-1 subunit precursor; Gamma-aminobutyric-acid receptor gamma-3 subunit precursor; Gamma-aminobutyric-acid receptor pi subunit precursor; Gamma-aminobutyric-acid receptor rho-1 subunit precursor; Gamma-aminobutyric-acid receptor rho-2 subunit precursor; Gamma-aminobutyric-acid receptor theta subunit precursor; GluR6 kainate receptor; Glutamate receptor 1 precursor; Glutamate receptor 2 precursor; Glutamate receptor 3 precursor; Glutamate receptor 4 precursor; Glutamate receptor 7; Glutamate receptor B; Glutamate receptor delta-1 subunit precursor; Glutamate receptor, ionotropic kainate 1 precursor; Glutamate receptor, ionotropic kainate 2 precursor; Glutamate receptor, ionotropic kainate 3 precursor; Glutamate receptor, ionotropic kainate 4 precursor; Glutamate receptor, ionotropic kainate 5 precursor; Glutamate [NMDA] receptor subunit 3A precursor; Glutamate [NMDA] receptor subunit 3B precursor; Glutamate [NMDA] receptor subunit epsilon 1 precursor;

Glutamate [NMDA] receptor subunit epsilon 2 precursor; Glutamate [NMDA] receptor subunit epsilon 4 precursor; Glutamate [NMDA] receptor subunit zeta 1 precursor; Glycine receptor alpha-1 chain precursor; Glycine receptor alpha-2 chain precursor; Glycine receptor alpha-3 chain precursor; Glycine receptor beta chain precursor; H/ACA ribonucleoprotein complex subunit 1; High affinity immunoglobulin epsilon receptor beta-subunit; Hypothetical protein DKFZp31310334; Hypothetical protein DKFZp761M1724; Hypothetical protein FLJ12242; Hypothetical protein FLJ14389; Hypothetical protein FLJ14798; Hypothetical protein FLJ14995; Hypothetical protein FLJ16180; Hypothetical protein FLJ16802; Hypothetical protein FLJ32069; Hypothetical protein FLJ37401; Hypothetical protein FLJ38750; Hypothetical protein FLJ40162; Hypothetical protein FLJ41415; Hypothetical protein FLJ90576; Hypothetical protein FLJ90590; Hypothetical protein FLJ90622; Hypothetical protein KCTD15; Hypothetical protein MGC15619; Inositol 1,4,5-trisphosphate receptor type 1; Inositol 1,4,5-trisphosphate receptor type 2; Inositol 1,4,5-trisphosphate receptor type 3; Intermediate conductance calcium-activated potassium channel protein 4; Inward rectifier potassium channel 13; Inward rectifier potassium channel 16; Inward rectifier potassium channel 4; Inward rectifying K(+) channel negative regulator Kir2.2v; Kainate receptor subunit KA2a; KCNH5 protein; KCTD 17 protein; KCTD2 protein; Keratinocyte-associated transmembrane protein 1; Kv channel-interacting protein 4; Melastatin 1; Membrane protein MLC1; MGC 15619 protein; Mucolipin-1; Mucolipin-2; Mucolipin-3; Multidrug resistance-associated protein 4; N-methyl-D-aspartate receptor 2C subunit precursor; NADPH oxidase homolog 1; Nav1.5; Neuronal acetylcholine receptor protein, alpha-10 subunit precursor; Neuronal acetylcholine receptor protein, alpha-2 subunit precursor; Neuronal acetylcholine receptor protein, alpha-3 subunit precursor; Neuronal acetylcholine receptor protein, alpha-4 subunit precursor; Neuronal acetylcholine receptor protein, alpha-5 subunit precursor; Neuronal acetylcholine receptor protein, alpha-6 subunit precursor; Neuronal acetylcholine receptor protein, alpha-7 subunit precursor; Neuronal acetylcholine receptor protein, alpha-9 subunit precursor; Neuronal acetylcholine receptor protein, beta-2 subunit precursor; Neuronal acetylcholine receptor protein, beta-3 subunit precursor; Neuronal acetylcholine receptor protein, beta-4 subunit precursor; Neuronal voltage-dependent calcium channel alpha 2D subunit; P2X purinoceptor 1; P2X purinoceptor 2; P2X purinoceptor 3; P2X purinoceptor 4; P2X purinoceptor 5; P2X purinoceptor 6; P2X purinoceptor 7; Pancreatic potassium channel TALK-Ib; Pancreatic potassium channel TALK-Ic; Pancreatic potassium channel TALK-Id; Phospholemman precursor; Plasmolipin; Polycystic kidney disease 2-related protein; Polycystic kidney disease 2-like 1 protein; Polycystic kidney disease 2-like 2 protein; Polycystic kidney disease and receptor for egg jelly-related protein precursor; Polycystin-2; Potassium channel regulator; Potassium channel subfamily K member 1; Potassium channel subfamily K member 10; Potassium channel subfamily K member 12; Potassium channel subfamily K member 13; Potassium channel subfamily K member 15; Potassium channel subfamily K member 16; Potassium channel subfamily K member 17; Potassium channel subfamily K member 2; Potassium channel subfamily K member 3; Potassium channel subfamily K member 4; Potassium channel subfamily K member 5; Potassium channel subfamily K member 6; Potassium channel subfamily K member 7; Potassium channel subfamily K member 9; Potassium channel tetramerisation domain containing 3; Potassium channel tetramerisation domain containing protein 12; Potassium channel tetramerisation domain containing protein 14; Potassium channel tetramerisation domain containing protein 2; Potassium channel tetramerisation domain containing protein 4; Potassium channel tetramerisation domain containing protein 5; Potassium channel tetramerization domain containing 10; Potassium channel tetramerization domain containing protein 13; Potassium channel tetramerization domain-containing 1; Potassium voltage-gated channel subfamily A member 1; Potassium voltage-gated channel subfamily A member 2; Potassium voltage-gated channel subfamily A member 4; Potassium voltage-gated channel subfamily A member 5; Potassium voltage-gated channel subfamily A member 6; Potassium voltage-gated channel subfamily B member 1; Potassium voltage-gated channel subfamily B member 2; Potassium voltage-gated channel subfamily C member 1; Potassium voltage-gated channel subfamily C member 3; Potassium voltage-gated channel subfamily C member 4; Potassium voltage-gated channel subfamily D member 1; Potassium voltage-gated channel subfamily D member 2; Potassium voltage-gated channel subfamily D member 3; Potassium voltage-gated channel subfamily E member 1; Potassium voltage-gated channel subfamily E member 2; Potassium voltage-gated channel subfamily E member 3; Potassium voltage-gated channel subfamily E member 4; Potassium voltage-gated channel subfamily F member 1; Potassium voltage-gated channel subfamily G member 1; Potassium voltage-gated channel subfamily G member 2; Potassium voltage-gated channel subfamily G member 3; Potassium voltage-gated channel subfamily G member 4; Potassium voltage-gated channel subfamily H member 1; Potassium voltage-gated channel subfamily H member 2; Potassium voltage-gated channel subfamily H member 3; Potassium voltage-gated channel subfamily H member 4; Potassium voltage-gated channel subfamily H member 5; Potassium voltage-gated channel subfamily H member 6; Potassium voltage-gated channel subfamily H member 7; Potassium voltage-gated channel subfamily H member 8; Potassium voltage-gated channel subfamily KQT member 1; Potassium voltage-gated channel subfamily KQT member 2; Potassium voltage-gated channel subfamily KQT member 3; Potassium voltage-gated channel subfamily KQT member 4; Potassium voltage-gated channel subfamily KQT member 5; Potassium voltage-gated channel subfamily S member 1; Potassium voltage-gated channel subfamily S member 2; Potassium voltage-gated channel subfamily S member 3; Potassium voltage-gated channel subfamily V member 2; Potassium voltage-gated channel, subfamily H, member 7, isoform 2; Potassium/sodium hyperpolarization-activated cyclic nucleotide-gated channel 1; Potassium/sodium hyperpolarization-activated cyclic nucleotide-gated channel 2; Potassium/sodium hyperpolarization-activated cyclic nucleotide-gated channel 3; Potassium/sodium hyperpolarization-activated cyclic nucleotide-gated channel 4; Probable mitochondrial import receptor subunit TOM40 homolog; Purinergic receptor P2X5, isoform A; Putative 4 repeat voltage-gated ion channel; Putative chloride channel protein 7; Putative GluR6 kainate receptor; Putative ion channel protein CATSPER2 variant i; Putative ion channel protein CATSPER2 variant 2; Putative ion channel protein CATSPER2 variant 3; Putative regulator of potassium channels protein variant 1; Putative tyrosine-protein phosphatase TPTE; Ryanodine receptor 1; Ryanodine receptor 2; Ryanodine receptor 3; SH3KBP1 binding protein 1; Short transient receptor potential channel 1; Short transient receptor potential channel 4; Short transient receptor potential channel 5;

Short transient receptor potential channel 6; Short transient receptor potential channel 7; Small conductance calcium-activated potassium channel protein 1; Small conductance calcium-activated potassium channel protein 2, isoform b; Small conductance calcium-activated potassium channel protein 3, isoform b; Small-conductance calcium-activated potassium channel SK2; Small-conductance calcium-activated potassium channel SK3; Sodium channel; Sodium channel beta-1 subunit precursor; Sodium channel protein type II alpha subunit; Sodium channel protein type III alpha subunit; Sodium channel protein type IV alpha subunit; Sodium channel protein type IX alpha subunit; Sodium channel protein type V alpha subunit; Sodium channel protein type VII alpha subunit; Sodium channel protein type VIII alpha subunit; Sodium channel protein type X alpha subunit; Sodium channel protein type XI alpha subunit; Sodium-and chloride-activated ATP-sensitive potassium channel; Sodium/potassium-transporting ATPase gamma chain; Sperm-associated cation channel 1; Sperm-associated cation channel 2, isoform 4; Syntaxin-1B1; Transient receptor potential cation channel subfamily A member 1; Transient receptor potential cation channel subfamily M member 2; Transient receptor potential cation channel subfamily M member 3; Transient receptor potential cation channel subfamily M member 6; Transient receptor potential cation channel subfamily M member 7; Transient receptor potential cation channel subfamily V member 1; Transient receptor potential cation channel subfamily V member 2; Transient receptor potential cation channel subfamily V member 3; Transient receptor potential cation channel subfamily V member 4; Transient receptor potential cation channel subfamily V member 5; Transient receptor potential cation channel subfamily V member 6; Transient receptor potential channel 4 epsilon splice variant; Transient receptor potential channel 4 zeta splice variant; Transient receptor potential channel 7 gamma splice variant; Tumor necrosis factor, alpha-induced protein 1, endothelial; Two-pore calcium channel protein 2; VDAC4 protein; Voltage gated potassium channel Kv3.2b; Voltage gated sodium channel beta1B subunit; Voltage-dependent anion channel; Voltage-dependent anion channel 2; Voltage-dependent anion-selective channel protein 1; Voltage-dependent anion-selective channel protein 2, Voltage-dependent anion-selective channel protein 3, Voltage-dependent calcium channel gamma-1 subunit; Voltage-dependent calcium channel gamma-2 subunit; Voltage-dependent calcium channel gamma-3 subunit; Voltage-dependent calcium channel gamma-4 subunit; Voltage-dependent calcium channel gamma-5 subunit; Voltage-dependent calcium channel gamma-6 subunit; Voltage-dependent calcium channel gamma-7 subunit; Voltage-dependent calcium channel gamma-8 subunit; Voltage-dependent L-type calcium channel alpha-1C subunit; Voltage-dependent L-type calcium channel alpha-ID subunit; Voltage-dependent L-type calcium channel alpha-1S subunit; Voltage-dependent L-type calcium channel beta-1 subunit; Voltage-dependent L-type calcium channel beta-2 subunit; Voltage-dependent L-type calcium channel beta-3 subunit; Voltage-dependent L-type calcium channel beta-4 subunit; Voltage-dependent N-type calcium channel alpha-1B subunit; Voltage-dependent P/Q-type calcium channel alpha-1 A subunit; Voltage-dependent R-type calcium channel alpha-1 E subunit; Voltage-dependent T-type calcium channel alpha-1 G subunit; Voltage-dependent T-type calcium channel alpha-1H subunit; Voltage-dependent T-type calcium channel alpha-11 subunit; Voltage-gated L-type calcium channel alpha-1 subunit; Voltage-gated potassium channel beta-1 subunit; Voltage-gated potassium channel beta-2 subunit; Voltage-gated potassium channel beta-3 subunit; Voltage-gated potassium channel KCNA7.

In some embodiments, exemplary G-protein coupled receptors (GPCRs) include, but are not limited to: Class A Rhodopsin like receptors such as Muse, acetylcholine Vertebrate type 1; Muse, acetylcholine Vertebrate type 2; Muse, acetylcholine Vertebrate type 3; Muse, acetylcholine Vertebrate type 4; Adrenoceptors such as Alpha Adrenoceptors type 1; Alpha Adrenoceptors type 2; Beta Adrenoceptors type 1; Beta Adrenoceptors type 2; Beta Adrenoceptors type 3; Dopamine Vertebrate type 1; Dopamine Vertebrate type 2; Dopamine Vertebrate type 3; Dopamine Vertebrate type 4; Histamine type 1; Histamine type 2; Histamine type 3; Histamine type 4; Serotonin type 1; Serotonin type 2; Serotonin type 3; Serotonin type 4; Serotonin type 5; Serotonin type 6; Serotonin type 7; Serotonin type 8; other Serotonin types; Trace amine, Angiotensin type 1; Angiotensin type 2; Bombesin; Bradykinin; C5a anaphylatoxin; Fmet-leu-phe, APJ like, Interleukin-8 type A; Interleukin-8 type B; Interleukin-8 type others, C—C Chemokine type 1 through type 11 and other types; C—X—C Chemokine (types 2 through 6 and others); C-X3-C Chemokine; Cholecystokinin CCK; CCK type A; CCK type B; and others; Endothelin; Melanocortin (Melanocyte stimulating hormone, Adrenocorticotropic hormone, Melanocortin hormone); Duffy antigen; Prolactin-releasing peptide (GPR10); Neuropeptide Y (type 1 through 7); Neuropeptide Y, Neuropeptide Y other, Neurotensin; Opioid (type D, K, M, X); Somatostatin (type 1 through 5); Tachykinin (Substance P (NK1), Substance K (NK2); Neuromedin K (NK3); Tachykinin-like 1; Tachykinin-like 2; Vasopressin/vasotocin (type 1 through 2); Vasotocin, Oxytocin/mesotocin; Conopressin; Galanin like; Proteinase-activated like (PAR1, PAR2, PAR3, PAR4); Orexin & neuropeptides; FFJQRFP; Chemokine receptor-like; Neuromedin U-like (Neuromedin U, PRXamide); hormone protein (Follicle stimulating hormone, Lutropin-choriogonadotropic hormone, Thyrotropin, Gonadotropin type I, Gonadotropin type II); (Rhod)opsin; Rhodopsin Vertebrate (types 1-5); Rhodopsin Vertebrate type 5; Rhodopsin Arthropod; Rhodopsin Arthropod type 1; Rhodopsin Arthropod type 2; Rhodopsin Arthropod type 3; Rhodopsin Mollusc; Rhodopsin; Olfactory (Olfactory II family 1 through 13); Prostaglandin (Prostaglandin E2 subtype EP1, Prostaglandin E2/D2 subtype EP2, Prostaglandin E2 subtype EP3, Prostaglandin E2 subtype EP4, Prostaglandin F2-alpha); Prostacyclin; Thromboxane; Adenosine type 1 through 3; Purinoceptors; Purinoceptor P2RY 1-4, 6,11; GPR 91; Purinoceptor P2RY5, 8, 9, 10; GPR 35; GPR 92; GPR 174; Purinoceptor P2RY 12-14; GPR87 (UDP-Glucose); Cannabinoid; Platelet activating factor; Gonadotropin-releasing hormone; Gonadotropin-releasing hormone type I; Gonadotropin-releasing hormone type II; Adipokinetic hormone like; Corazonin; Thyrotropin-releasing hormone & Secretogogue; Thyrotropin-releasing hormone; Growth hormone secretagogue; Growth hormone secretagogue-like; Ecdysis-triggering hormone (ETHR); Melatonin; Lysosphingolipid & LPA (EDG); Sphingosine 1-phosphat; Edg-1; Edg-2; Edg-3; Edg-4; Edg-5; Edg-6; Edg-7; Edg-8; Leukotriene B4 receptor BLT1; Leukotriene B4 receptor BLT2; Class A Orphan/other; Putative neurotransmitters; SREB; Mas proto-oncogene & Mas-related (MRGs); GPR45-like; Cysteinyl leukotriene; G-protein coupled bile acid receptor; Free fatty acid receptor (GP40, GP41, GP43); Class B Secretin-like; Calcitonin; Corticotropin-releasing factor; Gastric inhibitory peptide; Glucagon; Growth hormone-releasing hormone; Parathyroid hormone; PACAP; Secretin; Vasoactive intestinal polypeptide; Latrophilin; Larrophilin type 1; Latrophilin type 2; Latrophilin type 3; ETL receptors; Brain-specific angiogenesis inhibitor (BAI); Methuselah-like proteins (MTH); Cadherin EGF LAG (CELSR); Very large G-protein coupled receptor; Class C Metabotropic glutamate/pheroraone; Metabotropic glutamate group I through III; Calcium-sensing like; Extracellular calcium-sensing; Pheromone, calcium-sensing like other; Putative pheromone receptors; GABA-B; GABA-B subtype 1; GABA-B subtype 2; GABA-B like; Orphan GPRCS; Orphan GPCR6; Bride of sevenless proteins (BOSS); Taste receptors (T1R), Class D Fungal pheromone; Fungal pheromone A-Factor like (STE2, STE3); Fungal pheromone B like (BAR, BBR, RCB, PRA); Class E cAMP receptors; Ocular albinism proteins; Frizzled/Smoothened family; frizzled Group A (Fz 1, 2, 4, 5, 7-9); frizzled Group B (Fz 3 & 6); frizzled Group C; Vomeronasal receptors; Nematode chemoreceptors; Insect odorant receptors; and Class Z Archaeal/bacterial/fungal opsins.

In some embodiments, the replicon encodes a polypeptide that provides a cosmetic benefit to the subject. In some embodiments, the replicon encodes the polypeptide Botulinum toxin derived from the bacterium *Clostridium botulinum*, or a homolog or ortholog thereof. Botulinum toxin at high doses can cause botulism, often a fatal condition, but localized delivery of a small concentration of botulinum toxin delivered into the skin can provide a cosmetic benefit. Currently, two types of Botulinum toxin (BTX) are used therapeutically; type A (BTX-A) (Trade names: Botox®, Dysport®, and Xeomin®) and type B (BTX-B) (Trade name: MyoBloc). BTX is used therapeutically to treat strabismus (crossed eyes), blepharospasm (uncontrolled twitching or blinking of the eye), upper motor neuron syndrome, severe primary axillary hyperhidrosis (excessive sweating), cervical dystonia, chronic migraine, achalasia, chronic focal neuropathies, bruxism, idiopathic and neurogenic detrusor overactivity, incontinence, anal fissure, vaginismus, movement disorders associated with injury or disease of the central nervous system, focal dystonias, gastric cancer, temporomandibular joint pain disorders, diabetic neuropathy, wound healing, excessive salivation, vocal cord dysfunction, allergic rhinitis, and is used for cosmetic purposes (e.g. to treat wrinkles). In some embodiments, compositions described herein are used for localized delivery of BTX directly, e.g., to the skin.

In some embodiments, the replicon encodes one or more BTX, and is used cosmetically (e.g., to reduce the appearance of wrinkles). In other embodiments, the BTX in the composition is in the form of a BTX polypeptide, instead of being encoded in a recombinant alphavirus replicon, such that a defined dose of protein is provided (e.g., in a unit dose).

Other polypeptides that can be used for cosmetic purposes include, but are not limited to, calcitonin, adrenocorticotropic hormone, parathyroid hormone (PTH), hPTH (1→34), EGF, insulin, secretin, oxytocin, angiotensin, β-endorphin, glucagon, vasopressin, somatostatin, gastrin, luteinizing hormone-releasing hormone, enkephalin, neurotensin, atrial natriuretic peptide, somatotropin, somatotropin-releasing hormone, bradykinin, substance P, dynorphin, thyroid stimulating hormone, mammotrophic hormone, interferon, interleukin, G-C SF, glutathione peroxidase, superoxide dismutase, desmopressin, somatomedin, and endothelin.

Dendrimers and Dendrimer Nanoparticles

The term "dendrimer" is derived from its tree-like branching structure and are defined as synthetic macromolecules characterized by a large number of branching points, a three-dimensional globular shape, monodispersity, and nanometric size range. The globular shape of a dendrimer allows for a large number of terminal functional groups ("surface groups" or "surface reactive groups") whose chemical composition can be can be tailored to the desired application (e.g., drug immobilization). Because dendrimers are synthesized by the attachment of monomeric units that branch out in a stepwise manner, precise control of the molecular size, shape, density, polarity, flexibility, and solubility is feasible. The choice of different branching units and functional surface groups determine the final physical and chemical characteristics of the dendrimer-based nanostructure. Various types of dendrimers are available and any suitable dendrimer is contemplated for use in the compositions and methods disclosed herein. Exemplary dendrimers include, but are not limited to: polyamidoamine (PAMAM) dendrimers, polyglutamic acid dendrimers, poly-L-lysine dendrimers, polypropyleneimine (PPI) dendrimers, polymelamine dendrimers, triazine dendrimers, carbosilane dendrimers, DETM dendrimers, phosphorus dendrimers, polyester dendrimers, polyether dendrimers, PAMAMOS dendrimers, poly(N,N-dimethylaminoethyl methacrylate) (PDMAEMA) dendrimers, diethylaminoethyldextran (DEAE-dextran) dendrimers, tecto dendrimers, multilingial dendrimers, amphiphilic dendrimers, chiral dendrimers, and micellar dendrimers.

In some embodiments, the dendrimer or surface reactive groups of the dendrimer are modified. Any suitable dendrimer modification is contemplated by the disclosure herein. Exemplary dendrimer modifications include, but are not limited to: lipid-modified dendrimers (e.g., lipid-modified PAMAM or PPI dendrimers), fluorinated dendrimers (e.g., fluorinated PAMAM dendrimers), N-hydroxysuccinimide ester modified dendrimers (e.g., N-hydroxysuccinimide esters of PEG or an hydroxysuccinimide ester of a cell penetrating peptide), amino acid modified dendrimers (e.g., arginine and lysine modified PAMAM dendrimers), protein and peptide modified dendrimers, saccharide modified dendrimers (e.g., cyclodextrin modified PAMAM dendrimers), polymer modified dendrimers (e.g., PEGylation, hyaluronic acid modified dendrimers, or chitosan modified dendrimers), nanoparticle modified dendrimers (e.g., carbon nanotubes, graphene, quantum dots, gold nanoparticles, magnetic nanoparticles, upconversion nanoparticles, or silicon nanomaterials), and cationic moiety modified dendrimers (e.g., oligoarnine, tertiary amine, quaternary ammonium, imidazolium, guanidium, or phosphonium modified dendrimers). In a preferred embodiment, the recombinant alphavirus replicon is formulated in a PAMAM dendrimer nanoparticle. In some embodiments, the PAMAM dendrimer is a modified PAMAM dendrimer. In some embodiments, the amino surface reactive groups of a PAMAM dendrimer is modified by fluorination (e.g., by heptafluoro butyric acid anhydride). When the surface reactive groups of a dendrimer are modified, in some embodiments, only a portion of the surface reactive groups are modified. For instance, in some embodiments, a fluorinated PAMAM dendrimer comprises both unmodified amino surface reactive groups and fluorinated amino surface reactive groups.

Polyamidoamine (PAMAM) dendrimers are hyperbranched polymers that exhibit molecular uniformity, narrow molecular weight distribution, defined size and shape characteristics, and a multifunctional terminal surface. These nanoscale polymers are comprised of an ethylenediamine core, a repetitive branching amidoamine internal structure, and a primary amine surface reactive group. Dendrimers are "grown" off a central core in an iterative manufacturing process, with each subsequent step representing a new "generation" of dendrimer. Increasing generations produce macromolecules with larger molecular diameters, twice the number of reactive surface sites, and approximately double the molecular weight of the preceding generation.

PAMAM dendrimers are highly effective agents for the delivery of a wide variety of genetic materials into many cells. As synthetic non-viral vectors, PAMAM dendrimers can be specifically designed to minimize immune responses, cytotoxicity, and effectively stabilize polynucleic acids against nucleases for efficient delivery. PAMAM dendrimers contain a diverse range of available surface modifications, including, but not limited to: primary amino, carboxylate, hydroxy, mixed amine/hydroxyl, C12 hydrophobe, and succinamic acid surface reactive groups.

In some embodiments, the recombinant alphavirus replicon is formulated in a PAMAM dendrimer nanoparticle, wherein the PAMAM dendrimer comprises a primary amine surface reactive group. In some embodiments, the dendrimer is a generation 0 (G0), generation 1 (G1), generation 2 (G2), generation 3 (G3), generation 4 (G4), generation 5 (G5), generation 6 (G6), generation 7 (G7), generation 8 (G8), generation 9 (G9), or generation 10 (G10) PAMAM dendrimer that comprises amino surface reactive groups. In a preferred embodiment, the alphavirus replicon is formulated in a PAMAM dendrimer nanoparticle, wherein the PAMAM dendrimer is a G5 or G9 PAMAM dendrimer comprising amino surface reactive groups.

In some embodiments, the recombinant alphavirus replicon is formulated using a microfluidic mixing device. Microfluidic mixing devices facilitate controlled, bottom-up, molecular self-assembly of nanoparticles via custom-engineered microfluidic mixing cartridges that allow millisecond mixing of nanoparticle components at the nanoliter scale. Rapid mixing on a small scale allows reproducible control over particle formation compared to traditional methods of nanoparticle formation (such as hand mixing). In some embodiments, the recombinant alphavirus replicon is formulated as a PAMAM dendrimer nanoparticle using a microfluidic device. In some embodiments, the microfluidic device is a NanoAssemblr™ (Precision NanoSystems).

Encapsulation in Liposomes

In some embodiments, the one or more bioactive agents (e.g., polypeptides or recombinant alphavirus replicons) are encapsulated in a liposome. In some embodiments, various amphiphilic lipids form bilayers in an aqueous environment to encapsulate a bioactive agent-containing aqueous core as a liposome. In some embodiments, these lipids have an anionic, cationic or zwitterionic hydrophilic head group. In some embodiments, some phospholipids are anionic whereas others are zwitterionic. Suitable classes of phospholipid include, but are not limited to, phosphatidylethanolamines, phosphatidylcholines, phosphatidylserines, and phosphatidylglycerols. Exemplary cationic lipids include, but are not limited to, dioleoyl trimethylammonium propane (DOTAP), 1,2-distearyloxy-N,N-dimethyl-3-aminopropane (DSDMA), 1,2-dioleyloxy-N,Ndimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC and dodecylphosphocholine. In some embodiments, the lipids are saturated. In some embodiments, the lipids are unsaturated.

In some embodiments, liposomes are formed from a single lipid or from a mixture of lipids. In some embodiments, a mixture comprises: (i) a mixture of anionic lipids; (ii) a mixture of cationic lipids; (iii) a mixture of zwitterionic lipids; (iv) a mixture of anionic lipids and cationic lipids; (v) a mixture of anionic lipids and zwitterionic lipids; (vi) a mixture of zwitterionic lipids and cationic lipids; or (vii) a mixture of anionic lipids, cationic lipids and zwitterionic lipids. In some embodiments, a mixture comprises both saturated and unsaturated lipids. In some embodiments, a mixture comprises DSPC (zwitterionic, saturated), DlinDMA (cationic, unsaturated), and/or DMPG (anionic, saturated). In some embodiments, where a mixture of lipids is used, not all of the component lipids in the mixture need to be amphiphilic, e.g., one or more amphiphilic lipids are mixed with cholesterol.

In some embodiments, the hydrophilic portion of a lipid is modified by attachment (e.g., covalent attachment) of a polyethylene glycol (also referred to as PEGylation). In some embodiments, PEGylation increases stability and prevent non-specific adsorption of the liposomes. In some embodiments, lipids are conjugated to PEG using any suitable technique.

Liposomes are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter <50 nm, and LUVs have a diameter >50 nm. In some embodiments, liposomes are LUVs with a diameter in the range of 50-220 nm. In some embodiments, for a composition comprising a population of LUVs with different diameters: (i) at least 80% by number have diameters in the range of 20-220 nm; (ii) the average diameter (Zav, by intensity) of the population are in the range of 40-200 nm; and/or (iii) the diameters have a polydispersity index <0.2. A variety of techniques for preparing suitable liposomes are available and any suitable liposomal preparation technique is contemplated.

In some embodiments, encapsulating a bioactive agent increases the stability of the bioactive agent. In some embodiments, the time that a unit dose of a microneedle composition comprising a recombinant alphavirus particle encoding an antigen remains effective in inducing a detectable immune response to the antigen is increased by encapsulating the replicon in liposomes, relative to the replicon without encapsulation. In some embodiments, the increase is about or more than about 10%, 25%, 50%, 75%, 100%, 200%, 500%, or more. In some embodiments, the stability of the bioactive agent is more than doubled by encapsulating in liposomes. In some embodiments, encapsulating a bioactive agent in a liposome is effective in increasing efficiency of delivering the bioactive agent to a cell. In some embodiments, encapsulating in liposomes decrease the amount of bioactive agent necessary to achieve a desired result (e.g., a protective immune response) by 10%, 20%, 30%, 40%, 50%, 60%, 70%, 80%, 90%, 95%, or more, as compared to the amount required if the bioactive agent were delivered without encapsulation.

Dehydrated Compositions

Disclosed herein, in some embodiments, are microneedle devices for administering a recombinant alphavirus replicon or RNA molecule encoding an exogenous polypeptide comprising: a substrate comprising a plurality of microneedles; and a composition comprising a recombinant alphavirus replicon or RNA molecule encoding an exogenous polypeptide coated onto or embedded into the plurality of microneedles. Also disclosed herein, in some embodiments, are methods of preparing a microneedle device, comprising: obtaining a substrate comprising a plurality of microneedles; and coating or embedding a recombinant alphavirus replicon encoding an exogenous polypeptide onto or into the plurality of microneedles. Also disclosed herein, in some embodiments, are methods of inducing an immune response in an individual in need thereof, comprising: (a) contacting the dermal surface of an individual with a microneedle device comprising (i) a plurality of microneedles comprising a recombinant alphavirus replicon encoding an exogenous polypeptide coated onto or embedded into the plurality of microneedles, and (b) delivering the recombinant alphavirus replicon to the individual, thereby inducing an immune response in the individual.

In some embodiments, the RNA compositions described herein are provided in a dehydrated form. In some embodiments, a recombinant alphavirus replicon is in a dehydrated form, such as before or after applying to or embedding within microneedles. In some embodiments, the replicon encapsulated in a liposome is in a dehydrated form. In some embodiments, dehydration offers several advantages including increased stability of the composition, increased shelf-life of the composition, and reduced weight of the composition.

In general, the term "dehydration" refers to the removal of an amount of water from a composition. In some embodiments, a composition is dehydrated so as to remove about or at least about 10%, 20%, 30%, 40%, 50%, 60%, 70%, 80%, 90%, 95% or more of a starting amount of water. In some embodiments, at least 50% of a starting amount of water is removed. In some embodiments, the amount of water desired to be removed depends on the starting amount of water, so as to arrive at an amount of water at or below a target amount. In some embodiments, a composition is dehydrated so as to contain about or less than about 10%, 9%, 8%, 7%, 6%, 5%, 4%, 3%, 2%, 1%, 0.1%, 0.01%, or less water. In some embodiments, the dehydrated form contains less than 1% water. In some embodiments, a composition, or component thereof, is dehydrated to remove substantially all, e.g., 90%, 91%, 92%, 93%, 94%, 95%, 96%, 97%, 98%, 98.5%, 99%, or more water content. In some embodiments, a dehydrated replicon composition is substantially free of water content. In some embodiments, 98% of the water content of a composition is removed. In some embodiments, the starting form of a composition to be dehydrated is liquid, semi-liquid, semi-solid, solid, or a gel. In general, a composition that has been dehydrated is referred to as a "dried" composition. In some embodiments, a dried composition is in a powdered form. In some embodiments, a dried composition is gel-like. In some embodiments, a dehydrated composition includes a liquid replicon composition that has been reduced to a dried composition. In some embodiments, a dehydrated replicon composition has increased stability at room temperatures (e.g., temperatures between 21° C. to 28° C.). In some embodiments, a dehydrated replicon composition has increased shelf-life at room temperatures. In some embodiments, the increase in stability at room temperature is about or more than about 10%, 25%, 50%, 75%, 100%, 200%, 500%, or more, relative to the composition before dehydration, or an equivalent composition provided in liquid form.

In some embodiments, dehydration is accomplished by any number of methods. In one embodiments, dehydration of the replicon composition is accomplished by freeze-drying, also referred to as "lyophilization." In some embodiments, lyophilization involves the steps of freezing the water in a composition to the solid state, followed by sublimation. In some embodiments, sublimation is performed in a vacuum. In some embodiments, heat is applied to the composition to accelerate the sublimation process. In some embodiments, lyophilization removes substantially all of the water content of the composition. In some embodiments, lyophilization is used when low-temperature drying methods are desired. In some embodiments, freeze-drying machines are readily available from a number of different manufacturers.

In some embodiments, dehydration methods are not limited to lyophilization, and other methods of dehydration are contemplated. In some embodiments, a replicon composition is air-dried. In some embodiments, the replicons are washed with a volatile alcohol (e.g., isopropanol or ethanol). In some embodiments, this step replaces the water content in the composition with the volatile alcohol and precipitates the nucleic acid molecule. In some embodiments, after a step of centrifugation to pellet the precipitated nucleic acid molecule, the volatile alcohol is removed, such as by pipetting or pouring off the volatile alcohol, and the pelleted nucleic acid molecule is allowed to air-dry. In some embodiments, dehydration comprises the use of a desiccant. Examples of desiccants include alumina, aluminum amalgam, barium oxide, barium perchlorate, boric anhydride, calcium chloride (anhydrous), calcium oxide, calcium sulphate (anhydrous), copper (II) sulfate (anhydrous), magnesium amalgam, magnesium perchlorate (anhydrous), magnesium sulphate (anhydrous), phosphorus pentoxide, potassium, potassium carbonate (anhydrous), potassium hydroxide, silica gel, sodium, sodium hydroxide, sodium-potassium alloy, sodium sulphate (anhydrous), sulfuric acid, and the like. Other available methods of dehydration include heat drying, freeze-drying with liquid nitrogen, and spray drying.

In some embodiments, dehydrated bioactive agents are coated directly onto microneedle structures for administration to a subject. In some embodiments, a liquid replicon composition is spray-dried directly onto the microneedle to coat the structure. In another example, the microneedle is dipped into the liquid replicon composition and then the composition is air-dried onto the structure. In some embodiments, the liquid replicon or polypeptide composition is coated onto the microneedle using a microfluidic device (e.g., the BioDot printer described herein). In some embodiments, a dehydrated replicon composition is coated directly onto a metal microneedle structure. In other embodiments, the dehydrated replicon composition is coated directly onto a polymer microneedle structure. In yet other embodiments, the dehydrated replicon composition is coated directly onto a polymer-coated microneedle structure. In some embodiments, the composition including the microneedles themselves is dehydrated.

In some embodiments, the recombinant alphavirus replicon is packaged onto a microneedle using a microfluidic dispensing device. Microfluidic dispensing devices are non-contact liquid handling systems with high speed aspirating and dispensing capabilities that reproducibly dispense an accurate printing volume onto a microneedle, plurality of microneedles, or microneedle array. A microfluidic dispensing device typically utilizes a moveable stage holding a ceramic needle which accurately picks up a pre-determined volume of reagent (e.g., replicon RNA) and then ejects (prints) nanoliter volumes onto a substrate (e.g., a microneedle array) positioned on a printing table. In some embodiments, the microfluidic dispensing device is a BioDot AD1520 tabletop workstation.

In some embodiments, a dehydrated bioactive agent (e.g., a polypeptide or replicon) is incorporated into the microneedle itself (e.g., embedded into the microneedle). In some embodiments, a dehydrated replicon is mixed with a polymer before molding and polymerization. In some embodiments, the replicon-polymer composition is then molded and polymerized to form a solid microneedle structure wherein the replicon is contained within the microneedle structure. In some embodiments, the polymer substance is dissolvable, biodegradable, biosoluble, or a combination thereof such that upon application of the microneedle to the skin of a subject, the polymer is dissolved, biodegraded, and/or solubilized and the replicon is released.

Pharmaceutical Compositions

In some embodiments, the microneedle devices of the disclosure include the active components (e.g., a recombinant alphavirus replicon and/or a polypeptide) formulated as a pharmaceutical composition. In some embodiments, the pharmaceutical composition comprises a recombinant alphavirus replicon and a pharmaceutically acceptable carrier or excipient. In some embodiments, the microneedle devices of the present disclosure include a recombinant alphavirus replicon in water or in a buffer (e.g., a phosphate buffer, a Tris buffer, a borate buffer, a succinate buffer, a histidine buffer, or a citrate buffer), or any other pharmaceutically acceptable carrier or excipient. Any suitable pharmaceutically acceptable carriers or excipients are contemplated by the disclosure herein. In some embodiments, buffer salts, when present, are included in the 5-20 mM range. In some embodiments, pharmaceutical compositions have a pH between 5.0 and 9.5, e.g., between 6.0 and 8.0. In some embodiments, compositions include sodium salts (e.g., sodium chloride) to give tonicity. In some embodiments, a concentration of 10±2 mg/ml NaCl is typical, e.g., about 9 mg/ml. In some embodiments, pharmaceutical compositions include metal ion chelators. In some embodiments, chelators prolong RNA stability by removing ions which accelerate phosphodiester hydrolysis. Examples of chelators include, but are not limited to, EDTA, EGTA, BAPTA, pentetic acid, etc., which, in some embodiments, are present at between 10-500 µM e.g., 0.1 mM. In some embodiments, a citrate salt, such as sodium citrate, act as a chelator, while advantageously also providing buffering activity. In some embodiments, pharmaceutical compositions have an osmolality of between 200 mOsm/kg and 400 mOsm/kg, e.g., between 240-360 mOsm/kg, or between 290-310 mOsm/kg. In some embodiments, pharmaceutical compositions include one or more preservatives, such as thiomersal or 2-phenoxyethanol. In some embodiments, pharmaceutical compositions are mercury-free. In some embodiments, the pharmaceutical composition is preservative-free. In some embodiments, pharmaceutical compositions are sterile or sterilized. In some embodiments, pharmaceutical compositions are non-pyrogenic, e.g., containing <1 EU (endotoxin unit, a standard measure) per dose, and in some cases <0.1 EU per dose. In some embodiments, pharmaceutical compositions contain an RNAse inhibitor. Any suitable RNAse inhibitor is contemplated for use herein, such as those sold commercially by, e.g., Life Technologies, Sigma-Aldrich, & Roche. In some embodiments, pharmaceutical compositions are prepared in unit dose form.

In some embodiments, the pharmaceutical compositions disclosed herein further comprise a small molecule immunopotentiators. In some embodiments, the pharmaceutical composition includes a TLR2 agonist (e.g., Pam3CSK4), a TLR4 agonist (e.g., an aminoalkyl glucosaminide phosphate, such as E6020), a TLR7 agonist (e.g., imiquimod), a TLR8 agonist (e.g., resiquimod) and/or a TLR9 agonist (e.g., IC31). In some embodiments, any such agonist is selected to have a molecular weight of <2000 Da.

In some embodiments, replicon compositions are stored at low temperatures to maintain integrity of the replicon molecule. In some embodiments, suitable storage temperatures are −80° C. to +4° C. In some embodiments, the replicon composition is in a liquid form and is stored at −80° C. to +4° C. In other examples, the replicon composition is in a dehydrated form and is stored at room temperature.

Methods of Use

Disclosed herein, in some embodiments, are microneedle devices for administering a recombinant alphavirus replicon or RNA molecule encoding an exogenous polypeptide comprising: a substrate comprising a plurality of microneedles; and a composition comprising a recombinant alphavirus replicon or RNA molecule encoding an exogenous polypeptide coated onto or embedded into the plurality of microneedles. Also disclosed herein, in some embodiments, are methods of preparing a microneedle device, comprising: obtaining a substrate comprising a plurality of microneedles; and coating or embedding a recombinant alphavirus replicon encoding an exogenous polypeptide onto or into the plurality of microneedles. Also disclosed herein, in some embodiments, are methods of inducing an immune response in an individual in need thereof, comprising: (a) contacting the dermal surface of an individual with a microneedle device comprising (i) a plurality of microneedles comprising a recombinant alphavirus replicon encoding an exogenous polypeptide coated onto or embedded into the plurality of microneedles, and (b) delivering the recombinant alphavirus replicon to the individual, thereby inducing an immune response in the individual.

Conventional injection methods for delivering compounds (such as in vaccination with an antigen) bypass the skin's immune system and the compound is injected directly into sub-cutaneous tissue or muscle. The skin contains a large number of immune cells, including epidermal Langerhans cells and dermal dendritic cells. Without wishing to be bound by theory, these cells are thought to induce cell-mediated immune responses as well as enhance the production of antibodies by the antibody-releasing lymphocytes, B cells. In some embodiments, intradermal administration of vaccine is employed to trigger an immunogenic effect.

Disclosed herein, in some embodiments, are methods of preparing a microneedle device, comprising: obtaining a substrate comprising a plurality of microneedles; and coating or embedding a recombinant alphavirus replicon encoding an exogenous polypeptide onto or into the plurality of microneedles. In some embodiments, the method comprises packaging the recombinant alphavirus in or on (e.g., by coating onto or embedding into) microneedles and dehydrating the recombinant alphavirus before packaging. In some embodiments, the method comprises packaging the recombinant alphavirus in or on (e.g., by coating onto or embedding into) microneedles and dehydrating the recombinant alphavirus after packaging. Materials and methods for preparing recombinant alphavirus replicons and further packaging, dehydrating, and/or encapsulating can include any such materials and methods described herein, including with regard to any other aspect of the disclosure.

Disclosed herein, in some embodiments, are methods of inducing an immune response in an individual in need thereof, comprising: (a) contacting the dermal surface of an individual with a microneedle device comprising (i) a plurality of microneedles comprising a recombinant alphavirus replicon encoding an exogenous polypeptide coated onto or embedded into the plurality of microneedles, and (b) delivering the recombinant alphavirus replicon to the individual, thereby inducing an immune response in the individual. The "dermal surface" generally refers to the outer layer or substantially the outer layer of the epidermis (the layer of epidermal cells exposed to the outside environment). In some embodiments, replicons are packaged into or on microneedles for intradermal administration to a subject. In some embodiments, other routes of administration are possible depending on the target tissue to which a microneedle composition is to be applied. In some embodiments, other routes of administration include, but are not limited to, application to muscular tissue, intraperitoneal tissue, intradermal tissue, subcutaneous tissue, and buccal tissue (e.g., cheek or tongue). In some embodiments, administration of a dehydrated replicon occurs in a number of different ways. In one example, the dehydrated replicon is coated onto the surface of the microneedle and is dissolved upon direct application of the microneedle to the skin of a subject, or upon penetration of a dermal surface. In some embodiments, a dehydrated replicon dissolves in seconds or minutes. In some embodiments, the dehydrated replicon dissolves within about 5, 10, 15, 20, 25, 30, 45, 50, 60, 120, 180, or more seconds; or within minutes, such as within about 1, 2, 3, 4, 5, 6, 7, 8, 9, 10, 15, 20, 30, 60, 120 or more minutes.

In some embodiments, replicon compositions are used to deliver a polypeptide to a subject in need thereof. In some embodiments, the replicon encoding a tumor antigen is used to treat a cancer. Examples of cancer antigens for use in accordance with these methods have been described. Examples of cancers that are treated using microneedle compositions of the disclosure include, but are not limited to: Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor.

In some embodiments, therapeutic efficacy of the methods and compositions disclosed herein, with regard to the treatment of a cancer, whether benign or malignant, is measured by the degree to which the methods and compositions promote inhibition of tumor cell proliferation, the inhibition of tumor vascularization, the eradication of tumor cells, and/or a reduction in the size of at least one tumor such that a subject is treated for the proliferative disorder. In some embodiments, several parameters are considered in the determination of therapeutic efficacy are discussed herein. In some embodiments, the proper combination of parameters for a particular situation are established by the clinician. Progress in treating cancer (e.g., reducing tumor size or eradicating cancerous cells) are ascertained using any suitable method, such as those methods currently used in the clinic to track tumor size and cancer progress. In some embodiments, one efficacy parameter used to evaluate the treatment of cancer is a reduction in the size of a tumor. Tumor size can be figured using any suitable technique, such as measurement of dimensions, or estimation of tumor volume using available computer software, such as FreeFlight software developed at Wake Forest University that enables accurate estimation of tumor volume. In some embodiments, tumor size is determined by tumor visualization using, for example, CT, ultrasound, SPECT, spiral CT, MRI, photographs, and the like. In some embodiments, where a tumor is surgically resected after completion of the therapeutic period, the presence of tumor tissue and tumor size is determined by gross analysis of the tissue to be resected, and/or by pathological analysis of the resected tissue. In some embodiments, the growth of a tumor is stabilized (e.g., one or more tumors do not increase more than 1%, 5%, 10%, 15%, or 20% in size, and/or do not metastasize) as a result of treatment. In some embodiments, a tumor is stabilized for at least about 1, 2, 3, 4, 5, 6, 7, 8, 9, 10, 11, 12, or more weeks; or 1, 2, 3, 4, 5, 6, 7, 8, 9, 10, 11, 12, or more months. In some embodiments, the size of a tumor is reduced by at least about 5% (e.g., at least about 10%, 15%, 20%, or 25%). In some embodiments, tumor size is reduced at least about 30% (e.g., at least about 35%, 40%, 45%, 50%, 55%, 60%, or 65%). In some embodiments, tumor size is reduced at least about 70% (e.g., at least about 75%, 80%, 85%, 90%, or 95%). Most preferably, the tumor is completely eliminated, or reduced below a level of detection. In some embodiments, a subject remains tumor free (e.g., in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

In some embodiments, the present disclosure further provides for a method of monitoring an immune response in an individual. In some embodiments, the method comprises administering to the subject an alphavirus replicon composition; and assaying a sample from the subject to determine a level of an immune response in the individual against the exogenous polypeptide.

In some embodiments, the replicons are screened or analyzed to confirm their therapeutic properties using any suitable in vitro or in vivo testing methods available. In some embodiments, vaccines composed of replicons are tested for their effect on induction of proliferation or effector function of the particular lymphocyte type of interest, e.g., B cells, T cells, T cell lines, and T cell clones. In some embodiments, spleen cells from immunized mice are isolated and the capacity of cytotoxic T lymphocytes to lyse autologous target cells that contain a replicon that encodes the immunogen. In some embodiments, T helper cell differentiation is analyzed by measuring proliferation or production of TH1 (IL-2 and IFN-gamma) and/or TH2 (IL-4 and IL-5) cytokines by ELISA or directly in CD4+ T cells by cytoplasmic cytokine staining and flow cytometry.

In some embodiments, replicons that encode an antigen are tested for their ability to induce humoral immune responses, as evidenced, for example, by induction of B cell production of antibodies specific for an antigen of interest. In some embodiments, these assays are conducted using peripheral B lymphocytes from immunized individuals, but any suitable assay method is contemplated. In some embodiments, assays used to characterize replicons involve detecting expression of the encoded antigen by the target cells. In some embodiments, FACS is used to detect antigen expression on the cell surface or intracellularly. In some embodiments, FACS selection sorts for different levels of expression. In some embodiments, lower expression is desired. In some embodiments, other suitable method for identifying cells which express a particular antigen involve panning using monoclonal antibodies on a plate or capture using magnetic beads coated with monoclonal antibodies.

In some embodiments, a subject is pre-treated with an agent that facilitates delivery of the microneedle composition through the skin. In some embodiments, the pre-treatment is a physical disruption of the skin barrier. In some embodiments, the pre-treatment includes microdermabrasion, exfoliation, thermal ablation, chemical ablation, laser treatment, electric currents, electroporation, sonophoresis, and the like. In some embodiments, the pre-treatment is an application of a chemical agent. In some embodiments, the pre-treatment is a combination of physical disruption and a chemical agent. In some embodiments, the pre-treatment is a common cosmetic procedure performed before delivery of the bioactive agent. In some embodiments, the pre-treatment is a facial. In some embodiments, the pre-treatment is cleaning and/or disinfecting the surface to be treated. In some embodiments, a subject undergoing cosmetic treatment with a bioactive agent receives treatment at a dermatologist's office. In some embodiments, treatment comprises administering a microneedle composition comprising a bioactive agent (e.g., a recombinant alphavirus replicon) after pretreatment of the surface to which the microneedle composition is applied. In some embodiments, the pretreatment comprises wiping the surface to be treated with a wipe, swab, or other material. In some embodiments, the wipe, swab, or other material is supplied in a prepackaged form.

In some embodiments, the treatment comprises administering a microneedle composition comprising a BTX polypeptide for the treatment of wrinkles and frown lines. In some embodiments, treatment is coupled with another cosmetic procedure, for example, a facial. In some embodiments, the facial facilitates delivery of the replicon. In some embodiments, the subject receives the facial as a primary treatment. In some embodiments, a microneedle containing the BTX polypeptide is applied to an area of the face that received the facial, and preferably is a site of desired treatment. In some embodiments, BTX is delivered via intradermal administration to the subject.

Oral Compositions

Disclosed herein, in some embodiments, are methods for producing an oral composition and administering the oral composition to a subject. In some embodiments, the oral composition is used to deliver an RNA replicon or polypeptide to a subject. In some embodiments, the oral composition comprises a polynucleotide. In some embodiments, a polynucleotide is any nucleic acid molecule as described herein (i.e., DNA, RNA, or combinations thereof).

In some cases, the polynucleotide is an mRNA. In some embodiments, the mRNA is any RNA molecule comprising a coding sequence. In some embodiments, RNAs are generated by in vitro transcription, the methods of which have been described herein. In some embodiments, RNAs comprise a coding sequence or coding region that encodes a polypeptide. The polypeptide can be any of the polypeptide as disclosed herein. In some embodiments, the polypeptide is an antigen suitable for use as a vaccine. Examples of antigens suitable for use as vaccines are provided herein. In some cases, the antigen is a foreign antigen. In some embodiments, the foreign antigen is any foreign antigen disclosed herein. In some embodiments, the foreign antigen is an antigen associated with influenza virus (e.g., hemagglutinin (HA) or neuraminidase (NA)). In some embodiments, the antigen is a self-antigen (i.e., an antigen associated with cancer). In some embodiments, an antigen that is encoded by a replicon is delivered to a subject. In some embodiments, the antigen elicits an immune response in the subject. In some embodiments, mRNAs comprise a 7-methylguanosine cap (i.e., a 5' cap). In some embodiments, mRNAs comprise a polyadenylation tail. In some embodiments, mRNAs comprise a 5' untranslated region (5' UTR), a 3' untranslated region (3' UTR), or both.

In some embodiments, the oral composition comprises an RNA replicon. In some embodiments, RNA replicons are any RNA replicon as disclosed herein. In some embodiments, RNA replicons are derived from picornavirus, flavivirus, coronavirus, pestivirus, rubivirus, calcivirus, hepacivirus, or alphavirus. In some embodiments, RNA replicons comprise a coding sequence or coding region that encodes a polypeptide. In some embodiments, the polypeptide is any polypeptide as disclosed herein. In some embodiments, the polypeptide is an antigen suitable for use as a vaccine. Examples of antigens suitable for use as vaccines are provided herein. In some cases, the antigen is a foreign antigen. In some embodiments, the foreign antigen is any foreign antigen disclosed herein. In some embodiments, the foreign antigen is an antigen associated with influenza virus (e.g., hemagglutinin (HA) or neuraminidase (NA)). In some embodiments, the antigen is a self-antigen (i.e., an antigen associated with cancer). In some embodiments, any antigen that is encoded by a replicon is delivered to a subject. In some embodiments, the antigen elicits an immune response in the subject.

In some embodiments, the oral composition comprises one or more replicon molecules encoding one or more polypeptides. In some embodiments, the one or more replicon molecules encode one or more, two or more, three or more, four or more, five or more, six or more, seven or more, eight or more, nine or more, ten or more, or even more polypeptides. In some cases, one polypeptide is encoded by one replicon molecule. In other cases, more than one polypeptide is encoded by a single replicon molecule. In some embodiments, the oral composition is a quadrivalent influenza vaccine comprising a plurality of replicon molecules encoding hemagglutinin (HA) derived from four different influenza virus subtypes or strains. However, this disclosure is not limited to delivering vaccines. In some embodiments, a replicon encoding essentially any polypeptide as described herein is used in oral compositions (e.g., for gene therapy).

In some cases, the oral composition comprises viral vectors. In some embodiments, viral vectors are used to deliver an RNA or DNA sequence that encodes an antigen. In some embodiments, viral vectors are derived from a variety of viruses, of which non-limiting examples include lentiviruses, retroviruses, adenoviruses, adeno-associated viruses (AAV), rhabdoviruses (e.g., vesicular stomatitis virus), poxviruses (e.g., fowlpox virus, avian poxvirus, or vaccinia), alphaviruses (e.g., VEE, sindbis, or SFV), and the like. In some embodiments, the viral vector is derived from vesicular stomatitis virus (VSV). In some embodiments, viral vectors are derived from attenuated viruses such that the viral vector is replication defective. In some embodiments, the viral vector exhibits tropism such that specific tissues or cell types support the growth of the virus and other tissues or cell types do not support the growth of the virus. In some embodiments, the viral vector is modified to expand the tropism of the virus. In some embodiments, the viral vector is modified to limit the tropism of the virus. In some embodiments, the tropism is a particular species (e.g., a virus that can only infect avian cells). In some embodiments, the tropism of the virus is matched to the vaccine and consideration is made as to the species being vaccinated and the desired target tissue or cell type.

Formulations of Oral Compositions

In some embodiments, oral compositions are designed to be compatible with the environment of the gastrointestinal system. In some embodiments, oral compositions are limited by a number of factors that affect oral bioavailability, including poor solubility, low permeability, instability, and rapid metabolism. In some embodiments, these factors, among others, are considered when producing an oral composition of the disclosure.

In some embodiments, oral compositions of the disclosure comprise any polynucleotide as disclosed herein. In some embodiments, polynucleotides are "naked" (i.e., substantially free of other bioactive agents, excipients, and the like). In some embodiments, an oral composition comprises naked RNA replicons. In some embodiments, the naked polynucleotides are in a solid formulation. In some embodiments, the naked polynucleotides are precipitated (e.g., with PEG) and dehydrated to form a dry powder. In some embodiments, the naked polynucleotides are in a liquid formulation. In some embodiments, the polynucleotides are complexed with dendrimers, e.g., G5 and G9 dendrimers (Dendritech). Any suitable dendrimer, such as those described herein, are contemplated.

In some embodiments, the polynucleotides are encapsulated in liposomes. In some embodiments, methods of encapsulating polynucleotides in liposomes are described herein. In some embodiments, the composition comprises RNA replicons encapsulated in liposomes suitable for oral delivery to a subject. Without wishing to be bound by theory, the liposomes of the composition can bind to and penetrate the columnar epithelia of the intestines and release the RNA replicon "payload" into the cytoplasm. In some embodiments, the replicon is then translated into antigen polypeptides to evoke an immune response.

In some cases, the compositions comprise small nucleic acid lipid particles (SNALPs). In some embodiments, SNALPs are microscopic particles (~120 nm in diameter) that are used to deliver nucleic acids therapeutically to subjects. In some embodiments, SNALPs comprise any mix of cationic and fusogenic lipids. In some embodiments, SNALPs are coated with diffusible polyethylene glycol (PEG). In some embodiments, SNALPs are used to encapsulate the polynucleotides of the present disclosure and deliver the polynucleotides to a subject. In some embodiments, a SNALP is a liposome.

In some embodiments, compositions as described herein comprise a solid formulation. In some embodiments, non-limiting examples of solid formulations include a tablet, a capsule, or a pill. In some embodiments, solid formulations are suitable for oral administration of the composition to a subject in need thereof. In some embodiments, slow release formulations for oral administration are prepared in order to achieve a controlled release of the polynucleotides in contact with the body fluids in the gastrointestinal tract, and to provide a substantial constant and effective level of the polynucleotides in the blood plasma. In some embodiments, the polynucleotides are embedded for this purpose in a polymer matrix of a biological degradable polymer, a water-soluble polymer or a mixture of both, and optionally suitable surfactants. In some embodiments, embedding is the incorporation of micro-particles in a matrix of polymers. In some embodiments, controlled release formulations are obtained through encapsulation of dispersed micro-particles or emulsified micro-droplets via known dispersion or emulsion coating technologies. In some embodiments, the polynucleotide of the composition is formulated as a capsule. In some embodiments, the polynucleotide of the composition is a solid or liquid formulation encapsulated by the capsule.

In some embodiments, the formulation of the composition is enteric-coated. In some cases, a dried polynucleotide composition is formulated as an enteric-coated capsule. In some embodiments, a dried polynucleotide composition is formulated as an enteric-coated tablet. Without wishing to be bound by theory, enteric-coating can protect the composition from the acidic gastric juices of the stomach, can prevent irritation of the gastric mucosa, can delay the onset of action of the composition, and can target the release of the composition to the small intestine. In some embodiments, the enteric-coated formulation is a coated tablet, a sugar-coated tablet, a soft gelatin capsule, a hard gelatin capsule, a granulate, or a pellet. Non-limiting examples of enteric coatings suitable for use include: enteric film formers, for example, polymethacrylates (e.g., methacrylic acid ethacrylate poly (MA1-EA 1), methacrylic acid methyl methacrylate poly (MA 1-IMMA 1) and poly (MA 1-MMA2)), cellulose-based polymers (e.g., cellulose acetate phthalate, cellulose acetate trimellitate, cellulose acetate succinate, hydroxypropylmethylcellulose phthalate, hydroxypropylmethylcellulose acetate succinate), polyvinyl derivatives (e.g., polyvinyl acetate phthalate), half esters of the copolymerisate of styrene and maleic acid, half esters of the copolymerisate of vinyl ether and maleic acid, copolymerisate of vinyl acetate and crotonic acid; plasticizers, for example, alkyl esters of citric, tartaric and sebacic acids (e.g., diethyl sebacate, triethyl citrate, tributyl citrate, acetyitriethyl citrate, acetyltributyl citrate, dibutyl tartrate), esters of phthalic acid (e.g., dimethyl phthalate, diethyl phthalate, clibutyl phthalate, dioctyl phthalate, ethylphthaloyl- and butylphthaloyl ethyl glycolate), glycerol esters (e.g., castor oil, sesame oil, acetylated fatty acid glycerides, glycerol diacetate, glycerol triacetate), higher alcohols (e.g., glycerol, 1,2-propylene glycol), polyethers (e.g., polyethylene glycols and polyoxyethyiene polyoxypropylene block copolymers), surfactants (e.g., PEG-400 stearate, PEG sorbitane monooleate, sorbitane monooleate); anti-adhesion agents (e.g., talcum, magnesium stearate, micronized amorphous silicic acid, kaolin); colorants and pigments (e.g., titanium oxide, iron oxide pigments); and other additives.

In some embodiments, the compositions of the present disclosure further comprise any number of excipients. In some embodiments, excipients include any and all solvents, coatings, flavorings, colorings, lubricants, disintegrants, preservatives, sweeteners, binders, diluents, and vehicles. In some embodiments, the excipient is compatible with the therapeutic compositions of the present disclosure. In some embodiments, the excipient comprises vitamin B12, folate, or a combination thereof to facilitate uptake of the composition from the small intestine. In some cases, the excipient comprises polyethylene glycol (PEG). In some cases, the excipient comprises PEG derivatized with vitamin B12 (PEG/B12). In some embodiments, PEG and PEG/B12 is used to precipitate the polynucleotides of the disclosure. In some embodiments, the use of excipients in pharmaceutical compositions is well known in the art.

Dosage and Administration

In some embodiments, suitable doses of formulations of the disclosure are administered orally to a subject in need thereof. In some embodiments, the composition is administered with food. In some cases, a subject is in need or want of the formulation. In some embodiments, a subject in need or want of the formulation is a subject in need or want of a vaccine.

In some embodiments, a therapeutically effective amount of a polynucleotide of the disclosure is expressed as mg of the polynucleotide per kg of subject body mass. In some instances, a therapeutically effective amount is about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 120 mg/kg, about 140 mg/kg, about 160 mg/kg, about 180 mg/kg, about 200 mg/kg, about 220 mg/kg, about 240 mg/kg, about 260 mg/kg, about 280 mg/kg, about 300 mg/kg, about 320 mg/kg, about 340 mg/kg, about 360 mg/kg, about 380 mg/kg, about 400 mg/kg, about 420 mg/kg, about 440 mg/kg, about 460 mg/kg, about 480 mg/kg, about 500 mg/kg, about 520 mg/kg, about 540 mg/kg, about 560 mg/kg, about 580 mg/kg, about 600 mg/kg, about 620 mg/kg, about 640 mg/kg, about 660 mg/kg, about 680 mg/kg, about 700 mg/kg, about 720 mg/kg, about 740 mg/kg, about 760 mg/kg, about 780 mg/kg, about 800 mg/kg, about 820 mg/kg, about 840 mg/kg, about 860 mg/kg, about 880 mg/kg, about 900 mg/kg, about 920 mg/kg, about 940 mg/kg, about 960 mg/kg, about 980 mg/kg, about 1000 mg/kg, or greater than 1000 mg/kg.

In some embodiments, the composition is administered orally once or more than once. In some cases, the composition is administered orally as a single dose. In other cases, the composition is administered orally as two, three, four, five, six, seven, eight, nine, ten, or ten or more doses. In some embodiments, the doses are administered orally once a day, twice a day, three times a day, four times a day, five times a day, six times a day, seven times a day, eight times a day, nine times a day, ten times a day, or more than ten times a day. In some cases, the doses are administered once a day for one day, two days, three days, four days, five days, six days, seven days, eight days, nine days, ten days, or more than ten days. In some embodiments, the doses are administered consecutively (i.e., on consecutive days) or are separated by days in which no dose is administered. In some cases, the doses are administered once a week, once every two weeks, once every three weeks, once every month, once every two months, once every three months, once every four months, once every five months, once every six months, once every seven months, once every eight months, once every nine months, once every ten months, once every eleven months, once every year, or once more than every year.

In some embodiments, the compositions are administered as a "prime-boost" regimen. In some embodiments, a "prime-boost" regimen as defined herein is any vaccination regimen in which the immune system is "primed" to a target antigen and the immunity is selectively boosted by re-administering the target antigen. In some embodiments, the prime-boost is heterologous (i.e., a first vector is used to administer the target antigen ("prime") and a second, distinct vector is used to administer the target antigen ("boost")). In some embodiments, the prime-boost is homologous (i.e., the first and second vector are the same). In some embodiments, the "boost" requires multiple doses of any number of distinct vectors. In some embodiments, the prime-boost regimen comprises a "prime" with a first vector, followed by a "boost" with a second vector, followed by another "boost" with a third vector.

In some embodiments, the heterologous prime-boost comprises two or more distinct vectors. In some embodiments, the prime-boost comprises an alphavirus replicon encoding a target antigen to prime the immune system, followed by a VSV viral vector encoding the same target antigen to boost the immunity. Any combinations of distinct vectors, including any described herein, are contemplated for use in a heterologous prime-boost strategy. In some embodiments, the target antigens are the same. In some cases, the target antigens are different. In some cases, both vectors are administered by the same route of administration. In some embodiments, a first vaccine and a second vaccine are both delivered orally. In some embodiments, the first vaccine and second vaccines are administered by different routes of administration. In some embodiments, the first vaccine is administered orally to prime the immune system, followed by microneedle injection of the second vaccine to selectively boost the immunity. In some embodiments, the first vaccine is administered by microneedle injection followed by oral administration of the second vaccine. Non-limiting examples of administration routes suitable to perform the methods of the disclosure include subcutaneous injection, intravenous injection, intramuscular injection, intradermal injection, intraperitoneal injection, oral administration, intranasal administration, and infusion. In some cases, the first and second vectors are the same but are delivered by different routes of administration. In other cases, the first and second vectors are different but are delivered by the same route of administration. In yet other cases, the first and second vectors are different and are delivered by different routes of administration.

In some embodiments, prime-boost regimens encompass a period of time between delivery of the first vaccine and delivery of the second vaccine. In some embodiments, delivery of the first vaccine and delivery of the second vaccine occur on the same day (e.g., at the same hospital visit). In some embodiments, the second vaccine is delivered on the same day or one day, two days, three days, four days, five days, six days, one week, two weeks, three weeks, one month, two months, three months, four months, five months, six months, seven months, eight months, nine months, ten months, eleven months, one year, two year, three years, four years, five years, ten years, or more than ten years after delivery of the first vaccine.

Methods for Producing Influenza Vaccines

Disclosed herein, in some embodiments, are methods for producing influenza virus vaccines. Current standards in influenza virus vaccine production require months to manufacture an influenza vaccine. In some embodiments, the methods described herein reduce the time required to manufacture an influenza vaccine. In some cases, the improved methods require only two or three weeks to manufacture a new influenza vaccine. In some embodiments, one rate-limiting step in the manufacture of an influenza vaccine is the time required for antibody standards showing strain-specific hemagglutinin (HA) immunoreactivity to be produced.

In some aspects, the disclosure provides an improved method for producing strain-specific HA or neuraminidase (NA) protein standards. In some cases, the HA and/or NA protein standards are produced in an in vitro coupled transcription-translation system. In vitro transcription-translation systems are known in the art and can be purchased as kits commercially (e.g., from Promega). In some embodiments, the strain-specific HA and/or NA protein standards are produced with an affinity tag at the C-terminal end of the protein. In some embodiments, affinity tags are known in the art and include, without limitation, chitin binding protein (CBP), maltose binding protein (MBP), glutathione S-transferase (GST), and poly Histidine tag (HIS). In some embodiments, the affinity tag is used to purify the HA and/or NA protein standards. In some embodiments, the HA and/or NA proteins comprise a HIS tag appended to the C-terminus. In some embodiments, the HIS-tagged HA and/or NA proteins are purified by binding the HIS-tagged proteins to e.g., a nickel-affinity column or nickel magnetic agarose beads. In some embodiments, recombinant affinity-tagged HA and/or NA proteins are produced by any protein engineering methods commonly known in the art. In some cases, the recombinant affinity-tagged HA and/or NA proteins are produced in vitro, e.g., in bacterial cells. In some embodiments, the HA and/or NA protein standards are used to quantitate the amount of HA and/or NA antigen synthesized in cell culture in response to an influenza vaccine of the present disclosure. In some cases, the affinity-tagged HA and/or NA protein standards are used as antigens to rapidly produce HA and/or NA antibody standards. Methods of producing polyclonal antibodies in animals (e.g., rabbits) are well known in the art.

In some embodiments, the protein and antibody standards described herein are further utilized in an enzyme-linked immunosorbent assay (ELISA). Methods of producing and performing ELISA assays are commonly known in the art. In some embodiments, the ELISA assays are used to quantify the amount of HA and/or NA antigen synthesized in cell culture in response to an influenza vaccine of the present disclosure. In some embodiments, other methods of quantifying antigens and/or antibodies are known in the art and include, without limitation, single radial immunodiffusion assay (SRID), surface plasmon resonance detection, and Titer-on-Chip (Flu-ToC).

In some embodiments, the protein and antibody standards described herein, in some cases, are used to develop a hemagglutination inhibition assay. In some embodiments, the ability of a specific strain of influenza virus to agglutinate red blood cells is tested. In some embodiments, the influenza virus is added to a microwell plate comprising a plurality of red blood cells. Without wishing to be bound by theory, hemagglutinin (HA) present on the surface of the influenza virus can bind to N-acetylneuraminic acid on the surface of the red blood cells causing the virus to stick to the cells and form a lattice-like structure. In some cases, an HA antibody generated by any antigen or vaccine disclosed herein is used to prevent binding of the influenza virus to the red blood cells (and prevent agglutination). In some embodiments, the minimum concentration of HA antibody needed to inhibit binding of the virus to the cells determines the titer of the virus. In some embodiments, the HA antibody is any HA antibody produced by the methods of the present disclosure. In some cases, the HA antibody is derived from blood serum from a subject inoculated with a composition of the present disclosure (i.e., an HA antigen).

In some aspects, the disclosure provides for methods of gene profiling. In some embodiments, gene profiling is used to identify biomarkers of an immune response in a subject. In some embodiments, a subject undergoing vaccination with a composition of the present disclosure is screened for biomarkers indicative of an immune response. In some embodiments, gene profiling is performed on peripheral blood cells prior to vaccination as well as post-vaccination. In some embodiments, gene profiling is performed on peripheral blood cells prior to vaccination, 1-day post-vaccination, 3-days post-vaccination, and 7-days post-vaccination. In some cases, gene profiling is performed on a subject inoculated with a composition of the present disclosure. In some embodiments, the subject is a human. In some cases, the gene profiling is performed to assess the efficacy of a new influenza vaccine as part of e.g., a clinical trial.

Kits

Disclosed herein, in some embodiments, are kits for producing and/or administering a bioactive agent, such as a recombinant alphavirus replicon encoding an exogenous polypeptide. In some embodiments, a kit comprises one or more of any of the compositions disclosed herein, in any suitable combination. In some embodiments, the kit comprises materials for packaging the bioactive agent into or on a microneedle, materials for generating RNA nanoparticles (e.g., dendrimers), materials for dehydrating the bioactive agent (before or after application to a microneedle), and/or materials for encapsulating the alphavirus replicon in liposomes. In some embodiments, the kit comprises a composition in accordance with an embodiment of the disclosure in combination with instructions for administering the composition to a subject. In some embodiments, a kit comprises a tool for administering the composition to a subject. In some embodiments, the composition is provided in any suitable form, such as forms ready for immediate use or forms that require reconstitution by mixture with other materials (whether supplied in the kit or by the user).

In some embodiments, materials suitable for producing an alphavirus replicon include, without limitation, any combination of the following: a synthesized template DNA molecule comprising a gene encoding an exogenous polypeptide, an alphavirus replicon derived from any suitable alphavirus strain, an RNA-dependent RNA polymerase (e.g., T7 RNA Polymerase), buffers, primers, NTPs, restriction enzymes, RNA ligases, ribonuclease inhibitors, and the like.

In some embodiments, material suitable for packaging the alphavirus replicon into or on microneedles include, without limitation, any of the following: a microneedle or materials to produce a microneedle (e.g., polymer, molds, and the like), materials to dehydrate a replicon composition, and the like.

In some embodiments, kits contemplated herein include kits which include a composition comprising an alphavirus replicon encoding an exogenous polypeptide to a subject, wherein the composition is administered orally, and instructions for use of the same. In some embodiments, kits include a first composition comprising an alphavirus replicon encoding an exogenous polypeptide by a first route of administration and a second composition comprising an alphavirus replicon encoding an exogenous polypeptide by a second route of administration, as well as instructions for use of the same. In some embodiments, the first and second routes are the same. In some embodiments, the first and second routes are different. In some embodiments, the first route of administration is oral administration and the second route of administration is intradermal administration. In some embodiments, kits include compositions packaged in a microneedle when intradermal administration is contemplated.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1—Recombinant Alphavirus DNA Constructs

Figure 7:
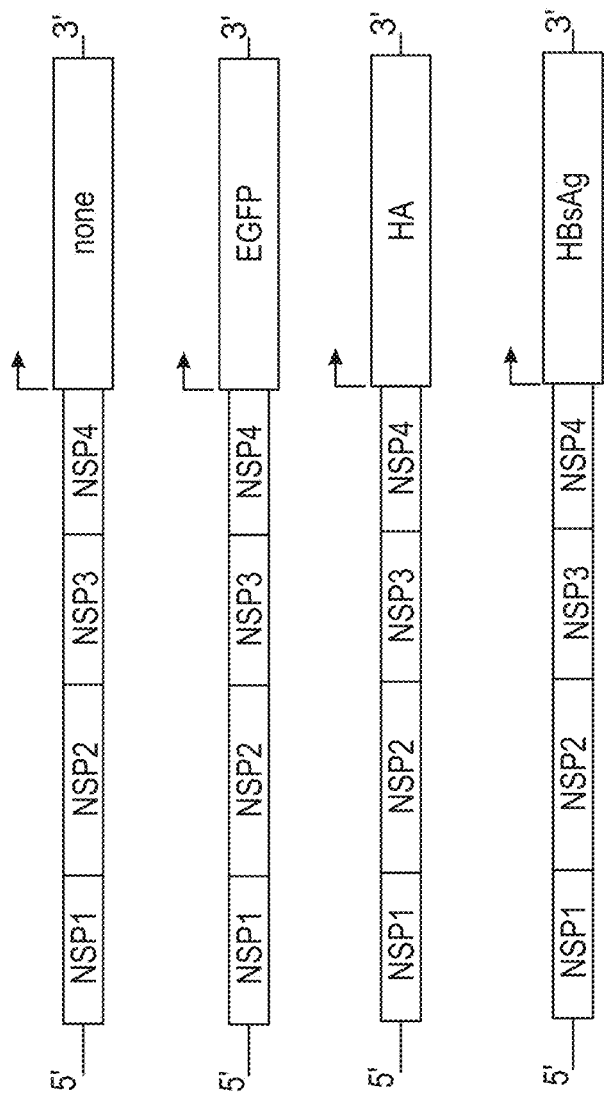
FIG. 7 exemplifies linear, self-replicating RNA replicons.
Figure 8:
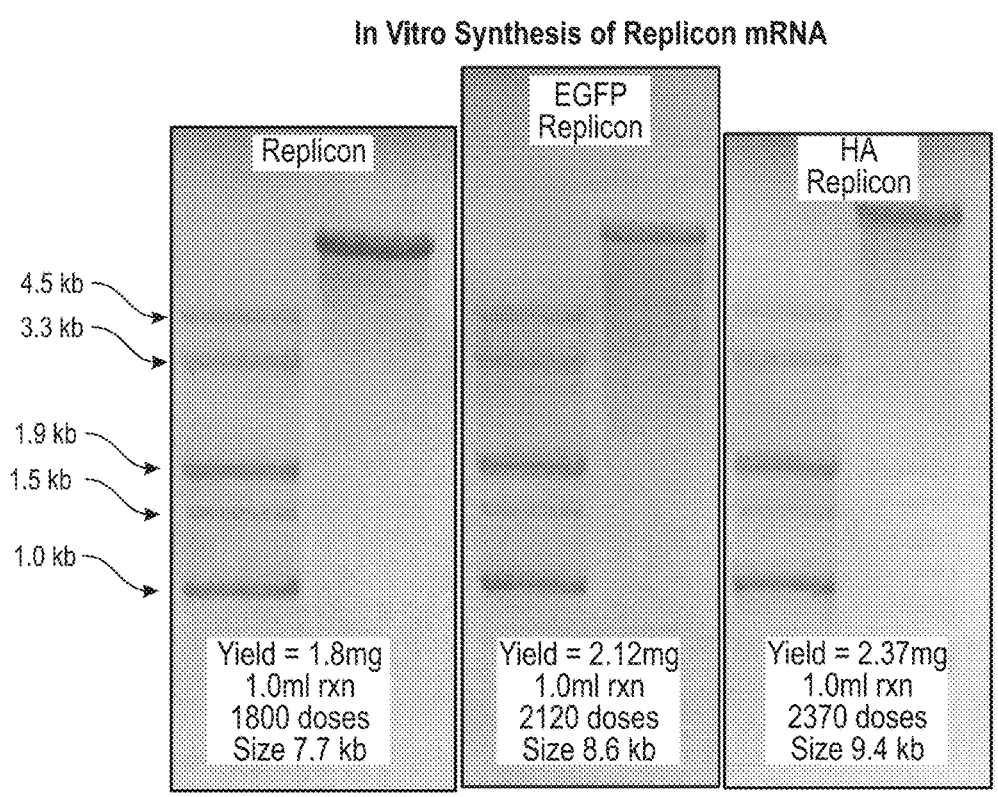
FIG. 8 is an exemplary agarose gel showing successful in vitro transcription of replicon RNA.
Figure 9:
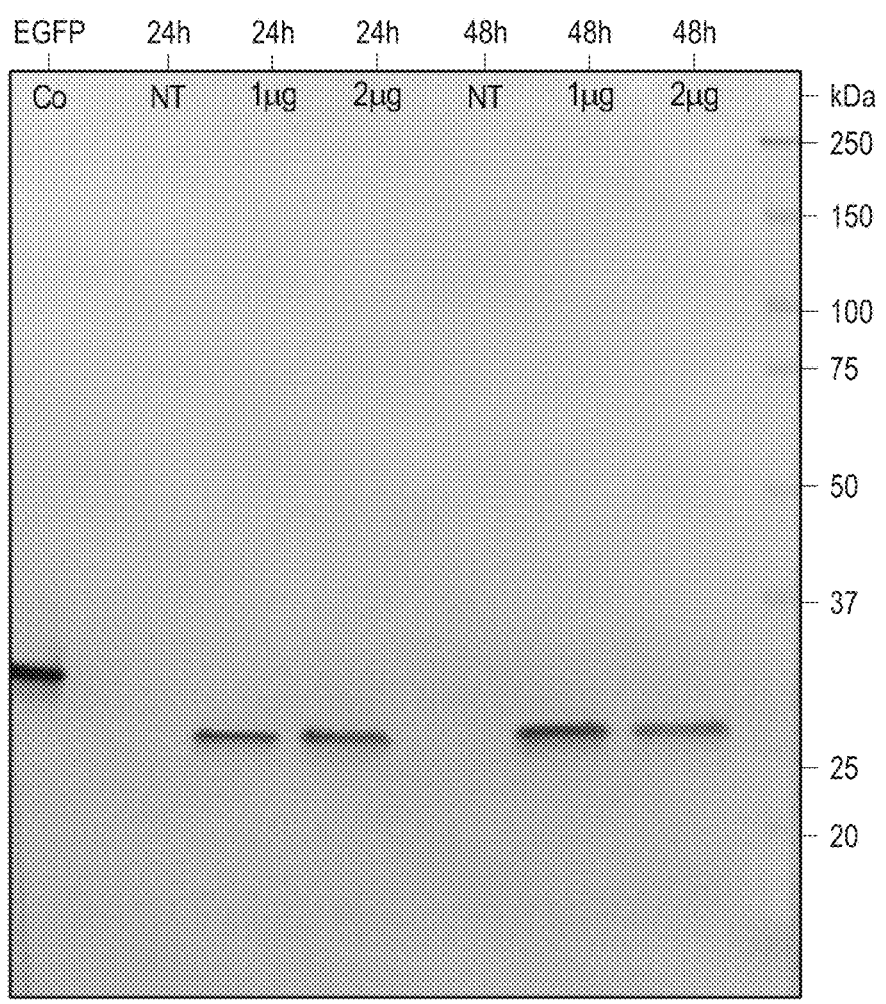
FIG. 9 is an exemplary EGFP western blot of 24 hour and 48 hour cell lysates obtained from EGFP-replicon transfected HEK-293T cells. Native replicon EGFP is a 26.9 kDa protein while the commercially-obtained positive control EGFP protein is a 32.7 kDa protein.
Figure 10:
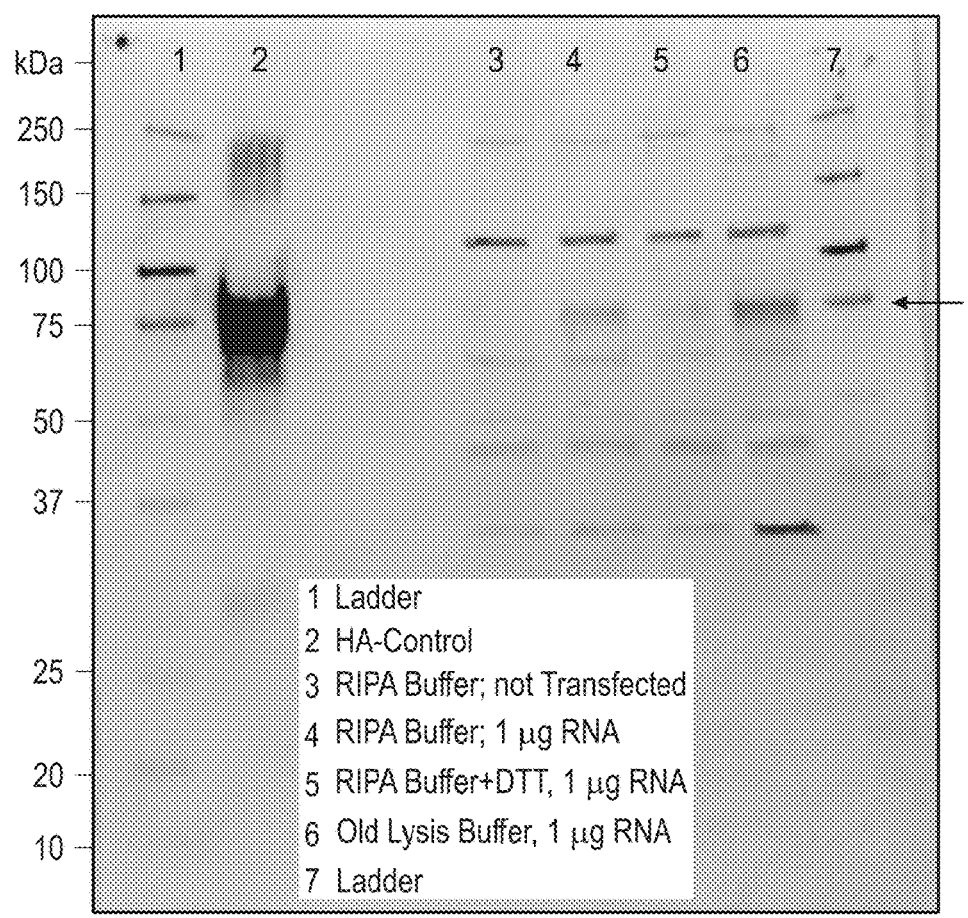
FIG. 10 is an exemplary influenza HA protein western blot of cell lysates obtained from HA-replicon transfected HEK-293T cells. Molecular weight ladders are shown in lanes 1 and 7, while HA protein positive control (72 kDa) is in lane 2. HA-replicon transfected samples are present in lanes 4, 5, and 6. Although the anti-HA antibody demonstrates some cross-reactivity with HEK-293 cell lysates, there is no 72 kDa band present in the lysate buffer-only negative control in lane 3.

DNA constructs were designed using DNASTAR Lasergene software (Madison, Wis.) with sequences from GenBank. Recombinant alphavirus replicons that encode an exogenous polypeptide were designed as illustrated in FIG. 7. Briefly, DNA sequences that encode for either enhanced green fluorescent protein (EGFP), influenza hemagglutinin protein (HA—see, e.g., GenBank Accession No.: KF009554.1), or hepatitis B virus surface antigen (HBsAg—see, e.g., GenBank Accession No.: KP659247.1; 155-

Figure 3:
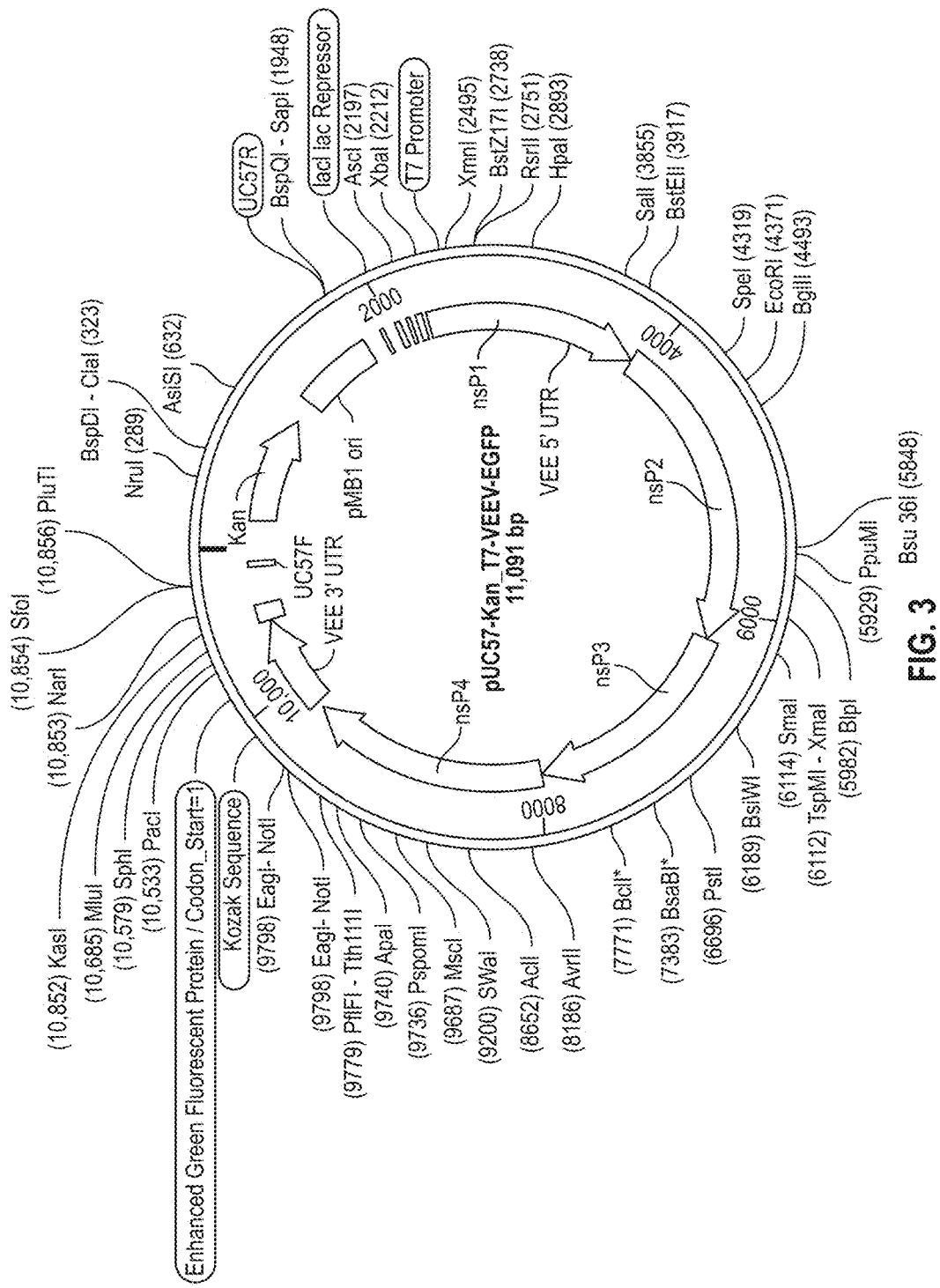
FIG. 3 exemplifies an EGFP-replicon containing DNA plasmid pUC57-Kan-T7-VEEV-EGFP.
Figure 4:
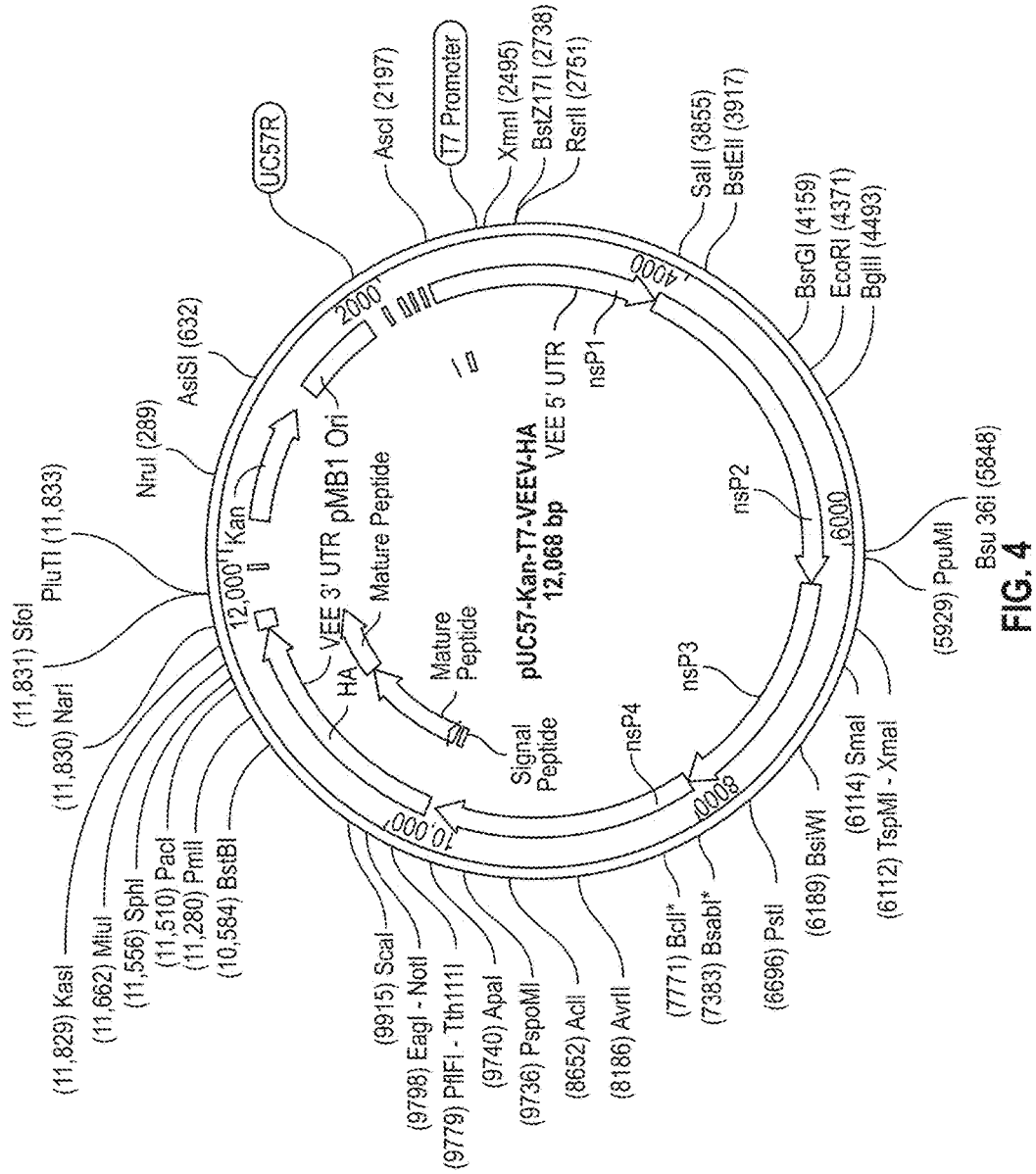
FIG. 4 exemplifies an influenza HA-replicon containing DNA plasmid pUC57-Kan-T7-VEEV-HA.
Figure 5:
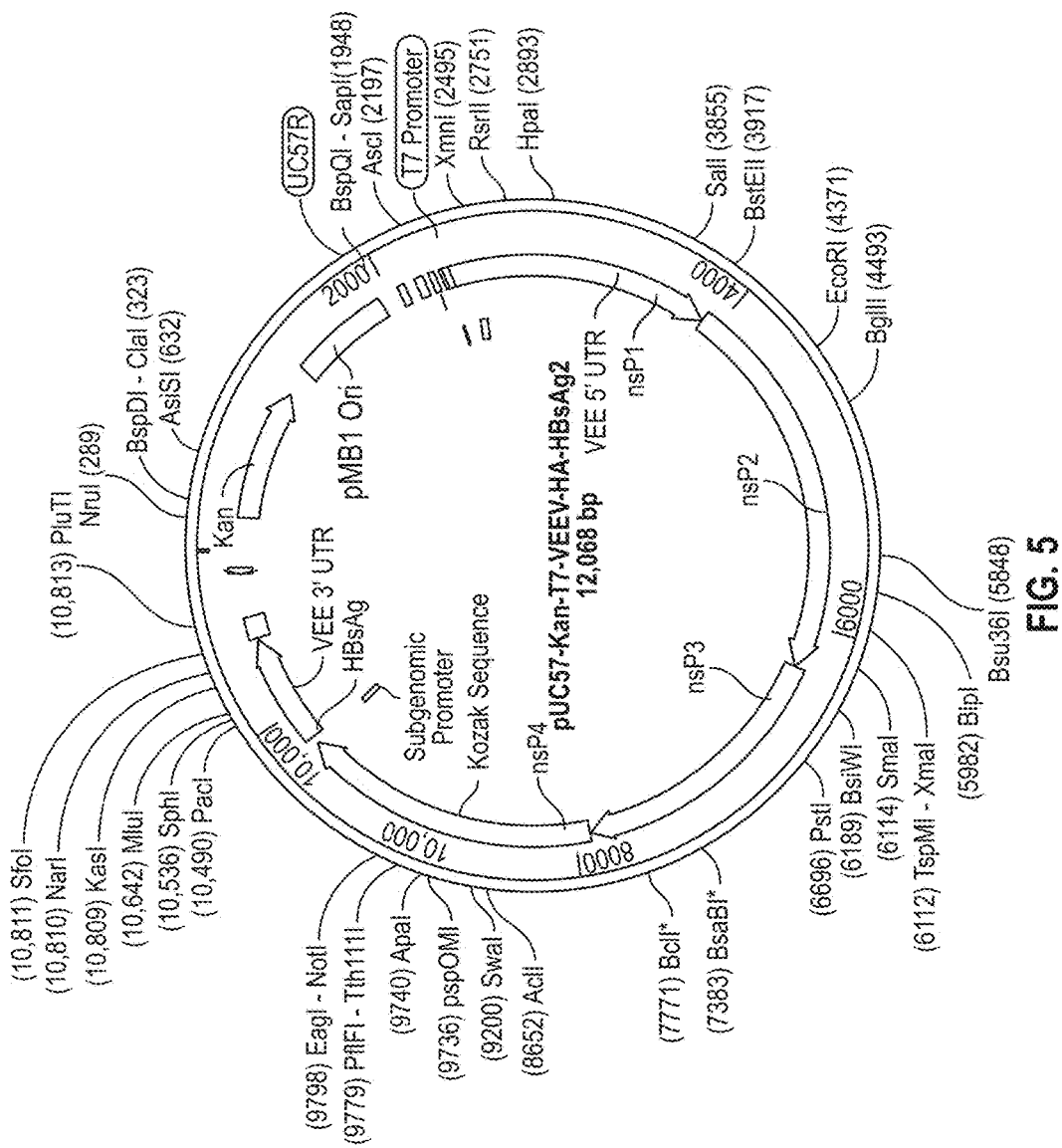
FIG. 5 exemplifies a hepatitis B surface antigen replicon DNA plasmid pUC57-Kan-T7-VEEV-HBsAg2.
Figure 6:
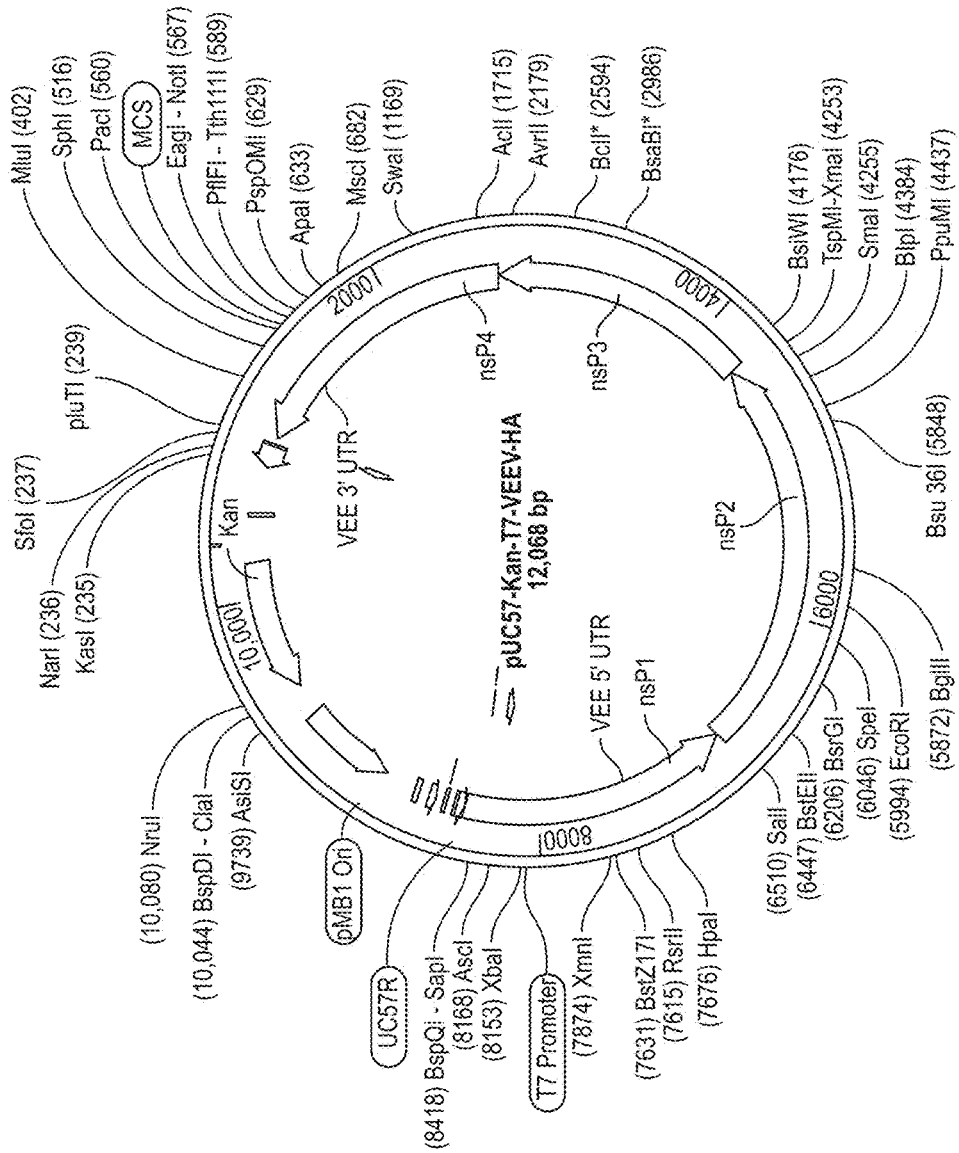
FIG. 6 exemplifies a replicon with no polypeptide ("empty replicon"); DNA plasmid pUC57-Kan-T7-VEEV.

835) were fused downstream (i.e., in the 3' direction) of an alphavirus replicon cassette containing the four alphavirus non-structural proteins (nsP1, nsP2, nsP3, and nsP4). An empty replicon cassette (i.e., containing only the alphavirus non-structural proteins and no gene-of-interest) was also designed. 5' and 3' untranslated regions (5' UTR and 3' UTR respectively) were also included in the replicon constructs to facilitate expression in host cells. The recombinant alphavirus replicons were inserted into the pUC57-Kan-T7 vector, as shown in FIG. 3 (pUC57-Kan-T7-VEEV-EGFP), FIG. 4 (pUC57-Kan-T7-VEEV-HA), FIG. 5 (pUC57-Kan-T7-VEEV-HBsAg), and FIG. 6 (pUC57-Kan-T7-VEEV).

DNA was synthesized and cloned by Genewiz (South Plainfield, N.J.) or DNA 2.0 (Newark, Calif.). DNA MiniPreps were prepared using the Zyppy™ Plasmid MiniPrep Kit Cat# D4036 (Zymo Research, Irvine, Calif.).DNA Maxipreps were performed using the PureLink™ Hi Pure Plasmid Maxiprep Kit (Invitrogen Cat #8002708). DNA sequencing was performed by the UC Davis DNA sequencing facility using the ABI Prism® 3730 Genetic Analyzer and BigDye® Terminator v. 3.1 Cycle Sequencing Kit with Gel Company Better Buffer. Any suitable gene-of-interest can be designed and synthesized as a recombinant alphavirus replicon as described above.

Example 2—In Vitro Synthesis of Recombinant Alphavirus Replicon RNA

Plasmid DNA described in Example 1 was linearized 3' to the insert with NdeI or MluI (New England BioLabs). RNA was synthesized in vitro from the linearized DNA template using the MEGAscript® Kit according to manufacturer's instructions (Ambion Cat# AM1333). RNA was purified according to manufacturer's instructions with the MEGAclear™ Kit for purification of large scale transcription reactions (Ambion Cat#1908). A 5' cap was added to the RNA using the Vaccinia Capping System (New England BioLabs Cat# M2080S). RNA was purified again using the MEGAclear™ Kit according to manufacturer's instructions. In some instances, TriLink (San Diego, Calif.) synthesized replicon RNA constructs from the appropriate DNA template. Various methods for in vitro transcription of RNA from plasmid DNA are available and any suitable methodology can be employed to generate the recombinant alphavirus replicons described herein.

1 μg of replicon RNA was diluted to 0.2 μg/μL and further diluted with an equal volume of sample loading dye, and run on a 1.0% agarose gel until the RNA bands were fully resolved. RNA from the T7-VEEV replicon (nsP1-4 only), T7-VEEV-EGFP replicon, and T7-VEEV-HA replicon (influenza A strain A/California/7/2009 H1N1) are shown in FIG. 8.

Example 3—Transfected Replicon RNA Induces Protein Expression In Vitro

Tissue Culture Methods

HEK-293T cells were provided by Dr. Peter Barry (UC Davis). Cells were grown in 5% $CO_2$ at 37° C. using Dulbecco's High Glucose MEM (Hyclone Cat# SH30022.01) with 10% Fetal Calf Serum (Gibco Cat#2140-087) and 50 U/ml Penicillin and 50 μg/ml Streptomycin. Cells were transfected with the HA or EGFP RNA replicons described in Example 2 using the Stemfect™ RNA Transfection Kit according to manufacturer's instructions (Stemgent, Cambridge, Mass.).

Western Blots

HEK-293T cells were transfected in a 6-well plate with 1 μg or 2 μg of HA-replicon or EGFP replicon and incubated for 24 hours or 48 hours at 37° C. in 5% $CO_2$. After the incubation period, cells were washed carefully with warm HBSS and harvested in 250 μl 1× lysis buffer. Lysates were incubated on ice for 20 min, sonicated for 1 min, and then centrifuged for 10 min at 14,000 rpm. The supernatant was transferred to clean tubes and the protein concentration determined using the Quant-iT™ Protein Assay Kit (Invitrogen) according to manufacturer's instructions.

Samples for gel electrophoresis were prepared in two concentrations, 20 μg/15 μl and 40 μg/15 μl. For sample preparation, supernatant aliquots were diluted with $ddH_2O$ and mixed with 4× Laemmli loading buffer, followed by heating for 20 minutes at 60° C. for denaturation. The samples (15 μl per lane) and a ladder (5 μl) were then loaded onto a 4-20% TGX gradient gel (Bio-Rad) and run for 30 minutes at 200V. After electrophoresis, the separated proteins were blotted onto a nitrocellulose membrane by tank (wet) electrotransfer. The gel, filter paper, and membrane were first equilibrated in transfer buffer and then were placed in the "transfer sandwich" [filter paper-gel-membrane-filter paper], cushioned by pads, and pressed together by a support grid. The supported gel sandwich was placed vertically in a tank between stainless steel/platinum wire electrodes and filled with transfer buffer. The transfer was performed at 100V for 1 hour. After transfer, the nitrocellulose membrane was stained with Ponceau S to confirm transfer.

After destaining in ddH2O, the membrane was blocked for 1 hour in 5% non-fat milk powder in 1× TBS, followed by incubation with mouse-anti-HA antibody (1:1000) or mouse anti-EGFP antibody in 0.5% nonfat milk powder in 1×TBS for 1 hour at room temperature on a rocking shaker. The membrane was then washed three times for 5 minutes each in 1×TBS/0.05% Tween-20 and then incubated with HRP-conjugated anti-mouse antibody (1:5000) in 0.5% non-fat milk powder in 1×TBS for 1 hour at room temperature on a rocking shaker, followed by three washes. Finally, the membrane was incubated with 1-Step TMB-Blotting substrate (Thermo Scientific) for 30 minutes at room temperature.

As shown in FIG. 9, HEK-293T cells transfected with either 1 μg or 2 μg of EGFP-replicon expressed readily detectable amounts of EGFP protein at both the 24 hour (lanes 3 and 4, FIG. 9) and 48 hour (lanes 6 and 7, FIG. 9) timepoints. Native EGFP (produced by the transfected EGFP replicons described above) is a 238 amino acid, 26.9 kDa protein while Biovision commercial EGFP (positive control, lane 1, FIG. 9) is 293 amino acid, 32.7 kDa protein. The 24 and 48 hour lysis buffer only samples (negative control, lanes 2 and 5, FIG. 9) did not contain any detectable EGFP bands.

HEK-293T cells transfected with either 1 μg or 2 μg (data not shown) of influenza A HA-replicon expressed readily detectable amounts of HA protein at both the 24 hour and 48 hour timepoints. As shown in FIG. 10, a full length 72 kDa HA protein band (positive control, lane 2, FIG. 10) is clearly visible. While the anti-HA antibody exhibits some cross-reactivity, there is no corresponding 72 kDa band seen in the buffer only negative control (lane 3, FIG. 10). Two different lysis buffers were tested on HA-replicon transfected samples (lanes 3-6, FIG. 10) and, as indicated by the arrow in FIG. 10, all samples analyzed had the 72 kDa HA band present.

EGFP Fluorescence Assay

HEK-293T cells were seeded in a 6-well plate and allowed to come to ~70% confluency after 24 hours. Media was then replaced and cells were transfected using Stemfect™ with either 0, 0.5, 1, 2, or 4 µg of an EGFP RNA replicon as described in Example 2. The remaining well was transfected with 1 µg EGFP mRNA as a positive control. After a 24 or 48 hour incubation period, media was removed and 0.5 mL of Cell Lysis Buffer was added to lyse cells. Cell lysates were analyzed for fluorescence using the Cubit fluorimeter according to manufacturer's instructions.

Figure 11:
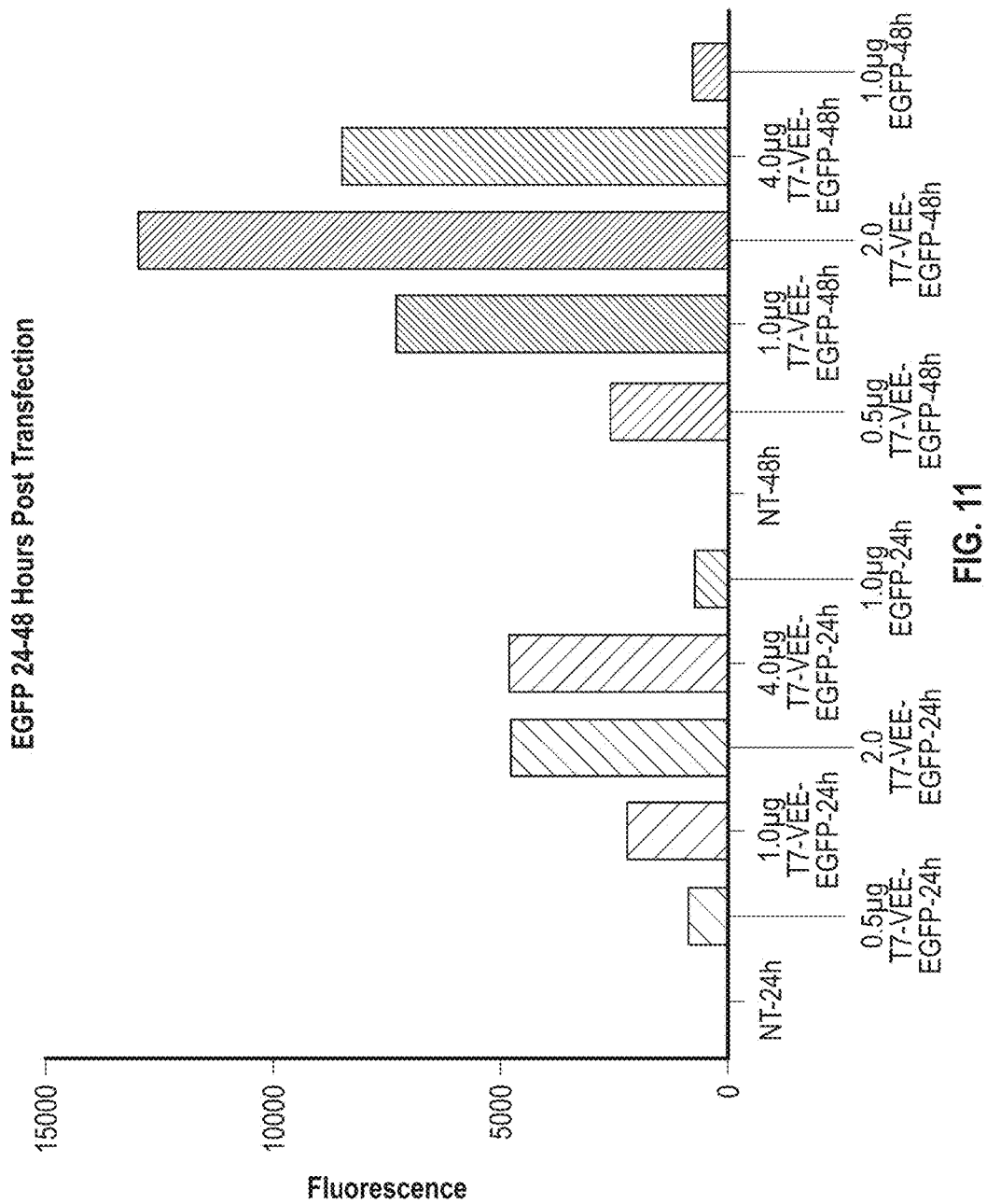
FIG. 11 is an exemplary analysis of EGFP fluorescence from HEK-293T cell lysates obtained 24-48 hours post EGFP-replicon transfection.
Figure 12:
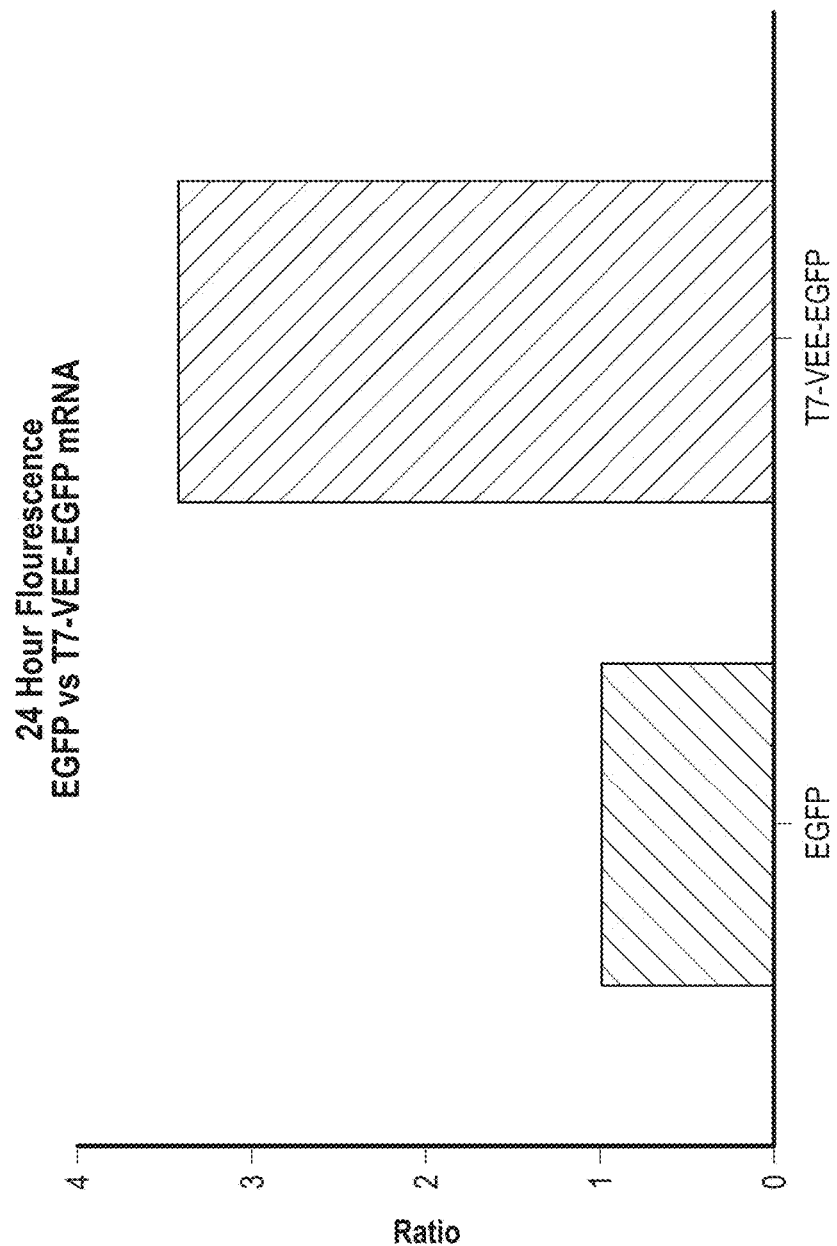
FIG. 12 is an exemplary comparison of the amounts of EGFP fluorescence of an EGFP-replicon RNA versus an EGFP mRNA.

As seen in FIGS. 11 and 12, transfection of the T7-VEEV-EGFP replicon leads to robust expression of EGFP. When the fluorescence of similar amounts of T7-VEEV-EGFP RNA and EGFP mRNA are compared, the T7-VEEV-EGFP replicon produces roughly 3.5 times as much EGFP compared to an EGFP mRNA (FIG. 12). At 48 hours post transfection, cells transfected with the T7-VEEV-EGFP replicon showed increased EGFP production suggesting mRNA was still being synthesized (FIG. 11). Cells transfected with EGFP mRNA show similar levels of EGFP fluorescence at 24 and 48 hours (FIG. 11).

Example 4—Coating and Elution of EGFP mRNA from BioDot Printed Microneedle

EGFP mRNA was transferred onto 5×5 microneedle arrays using two methods: (1) dipping; and (2) using the microfluidic dispensing BioDot printer.

Dipping Method

Arrays were first sonicated for ten minutes followed by baking at 450° C. for one hour. Following sterilization, 3 arrays were floated (dipped) on a 100 µL globule of 0.1 mg/mL EGFP mRNA in DEPC treated ddH$_2$O on parafilm for 30 minutes. Following coating, arrays were allowed to dry at ambient temperature. Three more arrays were coated using the BioDot printer.

BioDot Printing

Microneedle arrays were first cleaned by sonication at room temperature for 11 minutes at power setting 9 in a Steris Reliance Ultrasonic Cleaning System. Following sonication, arrays are either heat sterilized for 1 hour at 171° C. or siliconized. For siliconization, clean microneedle arrays are incubated for 20 seconds in a solution of 0.1% Dow Corning MDX4/2.5% Stoddard solvent/97.5% Isopropyl alcohol, removed from the solution, dried for 1 hour at room temperature, and cured overnight at 60° C. Following siliconization, arrays are heat sterilized as described previously and are now ready for printing.

The BioDot (AD1520) system allows for the fabrication of mRNA microneedles with high levels of reproducibility due to the accurate printing volumes. The instrument utilizes a moveable stage holding a ceramic needle (orifice 75-190 µm) which accurately picks up pre-determined volumes of reagent (mRNA) and then ejects (prints) nanoliter volumes on microneedle arrays positioned on a printing table.

The BioDot undergoes a wash step prior to mRNA printing including a number of aspiration and elution steps with 0.01% PBS to ensure removal of any air bubbles in the needle. Then, 5 µl of mRNA is aspirated into the ceramic needle and printed on microneedle arrays by repeatedly ejecting 5 nL drops on each microneedle, with a drying time of 60-120 seconds between prints. Following printing and drying, the microneedles are bent upwards in a 90° angle and are ready for use. A total of 40 nL of 1.0 mg/mL EGFP mRNA in Tris Buffer was coated onto each needle of the 5×5 array 5 nL at a time (1 µg total mRNA for the entire array). Arrays were allowed to dry at ambient temperature.

RNA Elution from Coated Microneedles

Figure 16:
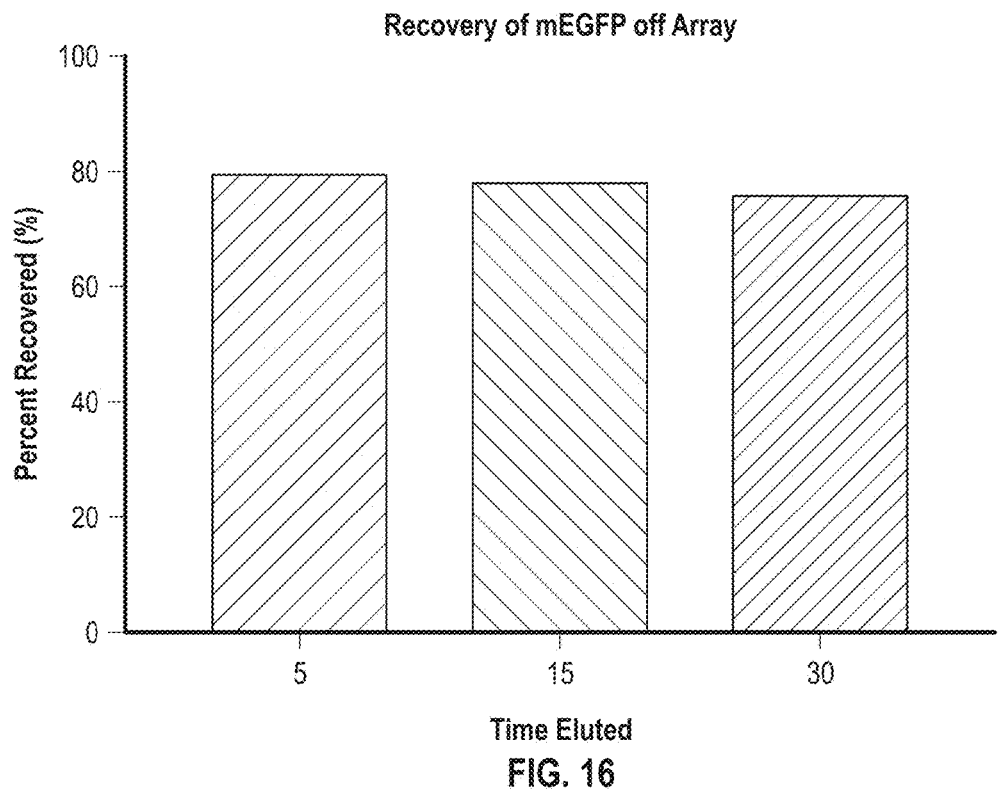
FIG. 16 exemplifies the recovery of EGFP mRNA from a BioDot printed microneedle array as measured by a cubit fluorimeter.

After coating and drying, arrays were floated on a globule of 100 µL DEPC treated ddH$_2$O on parafilm for 5, 15, and 30 minutes with mild shaking. Samples were collected from the arrays at each interval and kept on ice for further processing. After all samples were collected, an aliquot of each sample was tested for the presence of RNA using the cubit fluorimeter. The remaining samples were utilized for quantitative RT-PCR analysis. As seen in Table 1 and FIG. 16, recovery of EGFP mRNA from BioDot printed samples, was consistent and robust throughout the three elution times measured.

TABLE 1

EGFP mRNA Recovery from Dipped vs. BioDot Printed Microneedles

| Sample | Coating Method | Time (min) | Cubit (ng/µL) | RT-PCR (ng/µL) |
|---|---|---|---|---|
| 1 | BioDot | 5 | 2.52 | 7.9 |
| 2 | BioDot | 15 | 2.04 | 7.75 |
| 3 | BioDot | 30 | 2.04 | 7.54 |
| 4 | Dip | 5 | 6.12 | 24.75 |
| 5 | Dip | 15 | 4.46 | 17.18 |
| 6 | Dip | 30 | 1.6 | 7.95 |

Example 5—Microfluidic Formulation of RNA Nanoparticles

Nanoparticles were also formulated using the NanoAssemblr™ microfluidic mixing device (Precision Nanosystems) using a staggered herringbone micromixer chip. Briefly, polyamidoamine (PAMAM) C12 dendrimers (Dendritech cat#53,685-7 or 53,687-3) and 1,2-dimyristoyl-sn-glycero-3-phosphoethanolamine-N-[methoxy(polyethylene glycol)-2000] (Avanti Polar Lipids) were combined in ethanol. RNA was diluted with DNase/RNase-free, endotoxin-free water (Invitrogen) and sterile 100 mM (pH 3.0) QB Citrate Buffer (Teknova) or 100 mM Na Acetate (pH4.0) to a final citrate or acetate concentration of 10 mM. The ethanol and aqueous streams were loaded into a NanoAssemblr™ Microfluidic Cartridge and mixed in a 1:3 volumetric ratio with a combined flow rate of 5.0 ml/minute to produce nanoparticles. Nanoparticles were also prepared with polyethyleneimine (PEI, Sigma Aldrich) in the ethanol phase. Nanoparticles were dialyzed against PBS using 20,000 molecular weight cut-off Slide-A-Lyzer G2 dialysis cassettes. Dialyzed nanoparticles were concentrated with Amicon spin filters and sterile-filtered using 0.2 µm poly(ether sulfone) filters (Genesee Scientific). Nanoparticles were characterized with a Zetasizer NanoZS (Malvern); see Lipid Nano Particle and Lipid Nano Particle #2 in FIGS. 14 and 15.

Example 6—Formulation of RNA Replicon Dendrimer Nanoparticles

Figure 13:
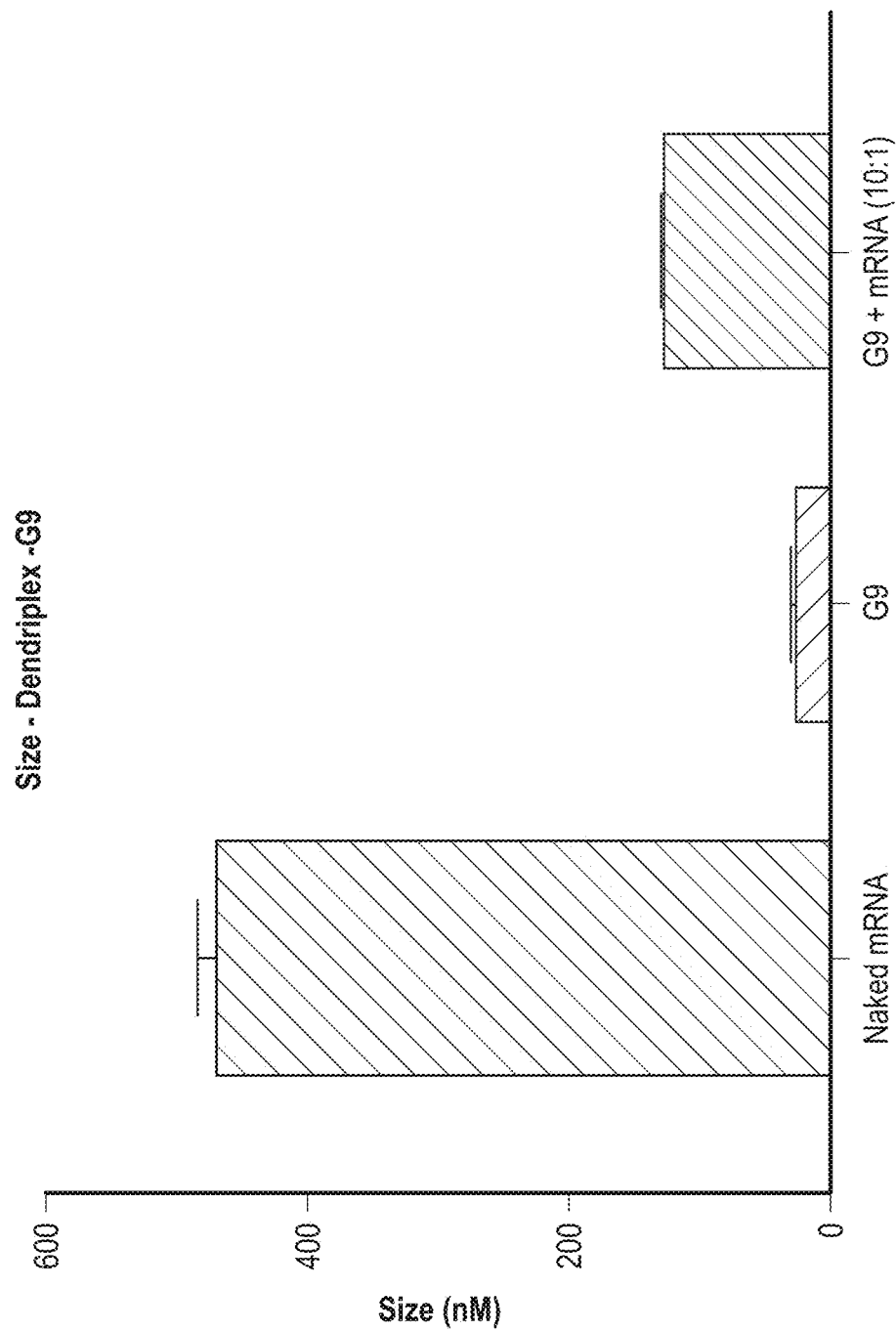
FIG. 13 is an exemplary Malvern Zetasizer characterization of the size of replicon RNA, G9 dendrimer, and the dendrimer-replicon complex.
Figure 14:
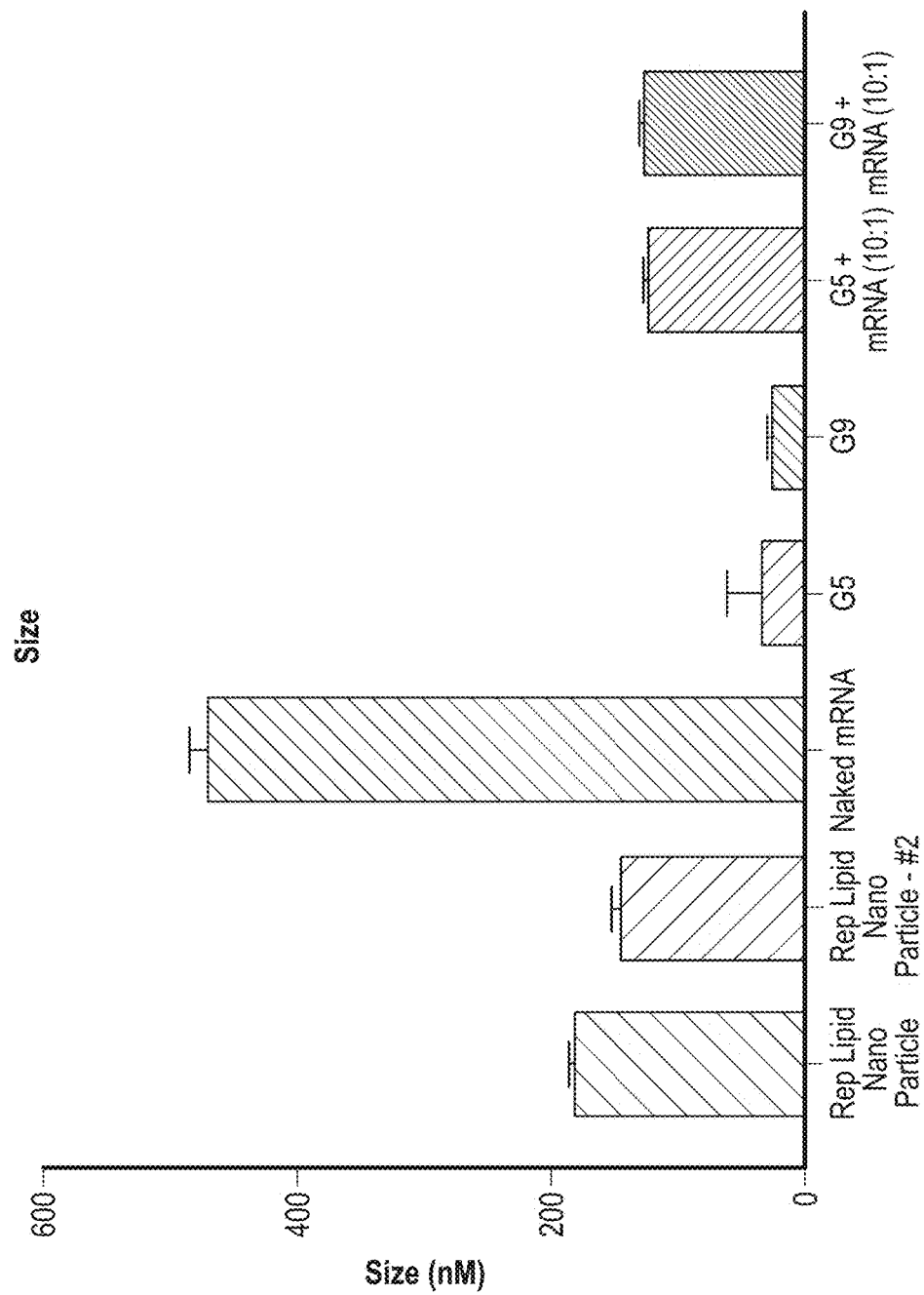
FIG. 14 is an exemplary Malvern Zetasizer characterization of the size of replicon particles made with lipids or dendrimers following nanoparticle assembly in either the Precision NanoSystems microfluidic mixing NanoAssemblr (Rep Lipid Nano particle, Rep Lipid Nano particle #2) or mixed by hand (remaining samples).
Figure 15:
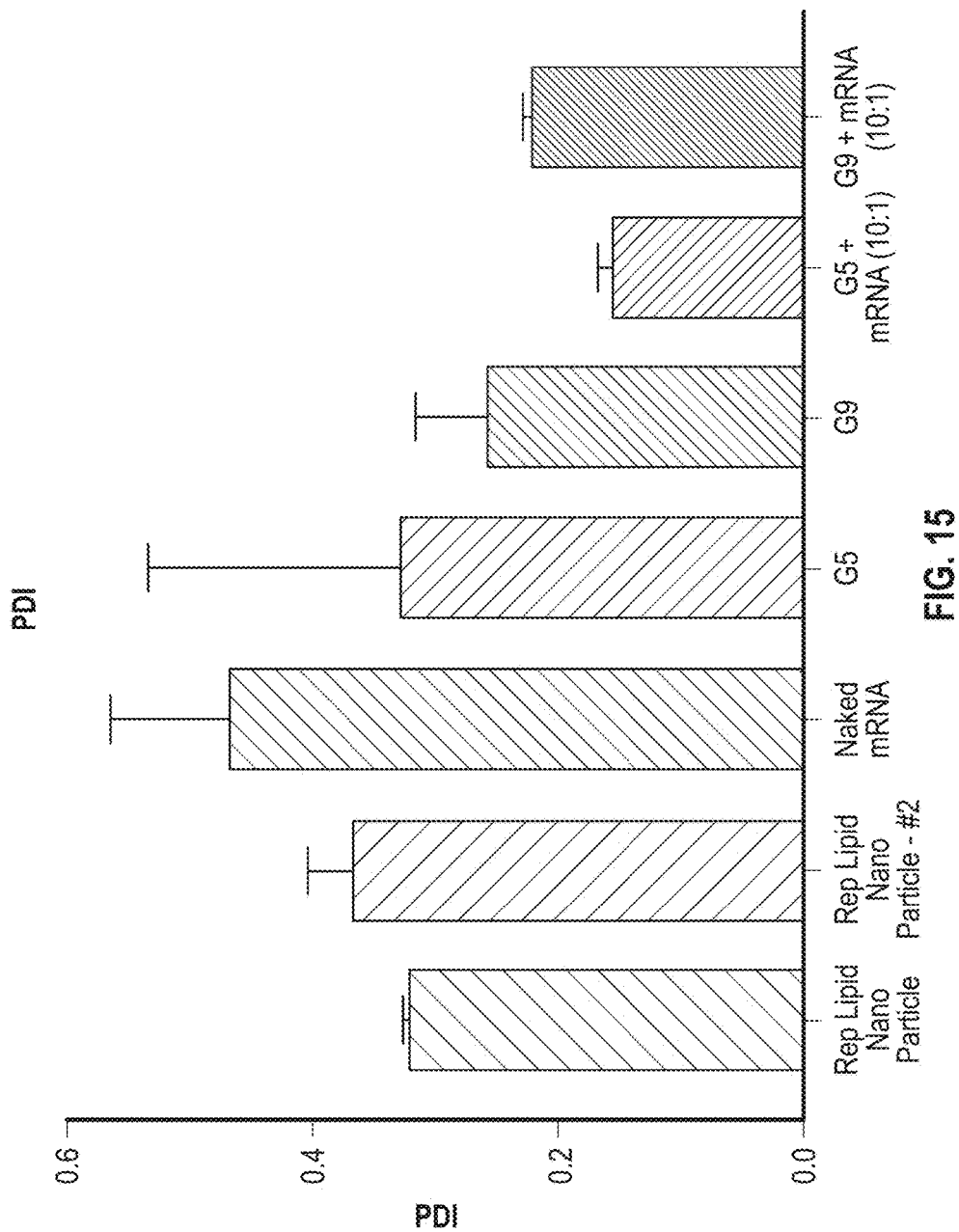
FIG. 15 is an exemplary Malvern Zetasizer characterization of the polydispersity index (PDI) of replicon particles made with lipids or dendrimers following nanoparticle assembly with either the Precision NanoSystems microfluidic mixing NanoAssemblr (Rep Lipid Nano particle, Rep Lipid Nano particle #2) or mixed by hand (remaining samples).

G5 and G9 NH$_2$ PAMAM dendrimers were from Dendritech. EGFP-replicon dendriplexes were formed at an N/P ratio of 20 (N from the dendrimer, P from the replicon RNA). Size (FIGS. 13 and 14) and polydispersity index (PDI) (FIG. 15) was determined for naked RNA, the dendrimer (G5 and G9 respectively), and the corresponding dendrimer nanoparticle (G5+replicon RNA and G9+replicon RNA). As shown in FIGS. 13 and 14, both G5 and G9 dendrimers dramatically reduced the size of RNA molecule.

Figure 21:
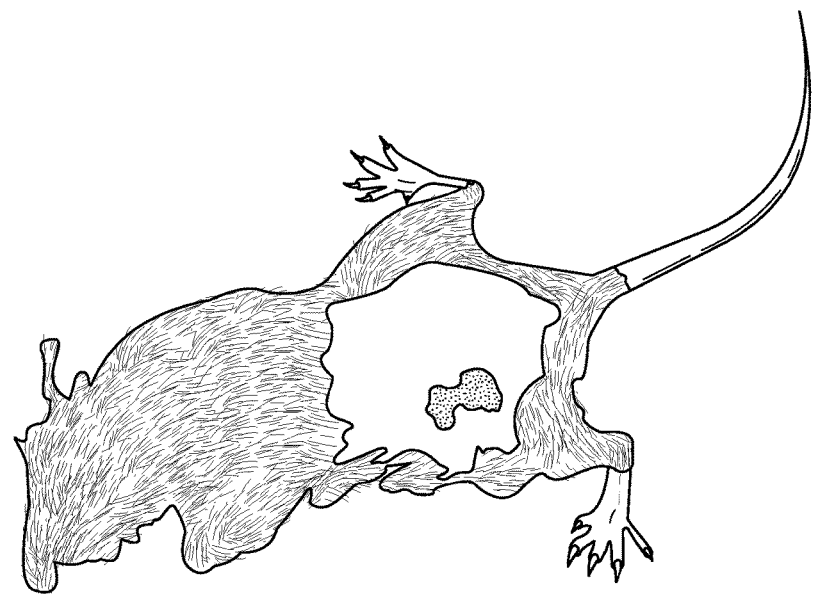
FIG. 21 is an illustration of EGFP fluorescence in the dorsal skin of a mouse treated with a microneedle array patch containing EGFP protein.

Example 7—In Vivo Detection of EGFP Fluorescence in Mice Treated with an EGFP Protein Coated Microneedle Device Microneedle arrays were prepared as described in Example 8. EGFP protein was coated onto microneedle array using the BioDot microfluidic dispensing device as descried in Example 4. The dorsal skin hair of Balb/c mice was removed as described in Example 8, and the EGFP-protein coated microneedle patch was applied to the exposed skin. After a 20 minute incubation period, the presence of EGFP protein was visualized by fluorescence. Localization of EGFP from an array patch applied to a mouse is exemplified in FIG. 21.

Figure 17:
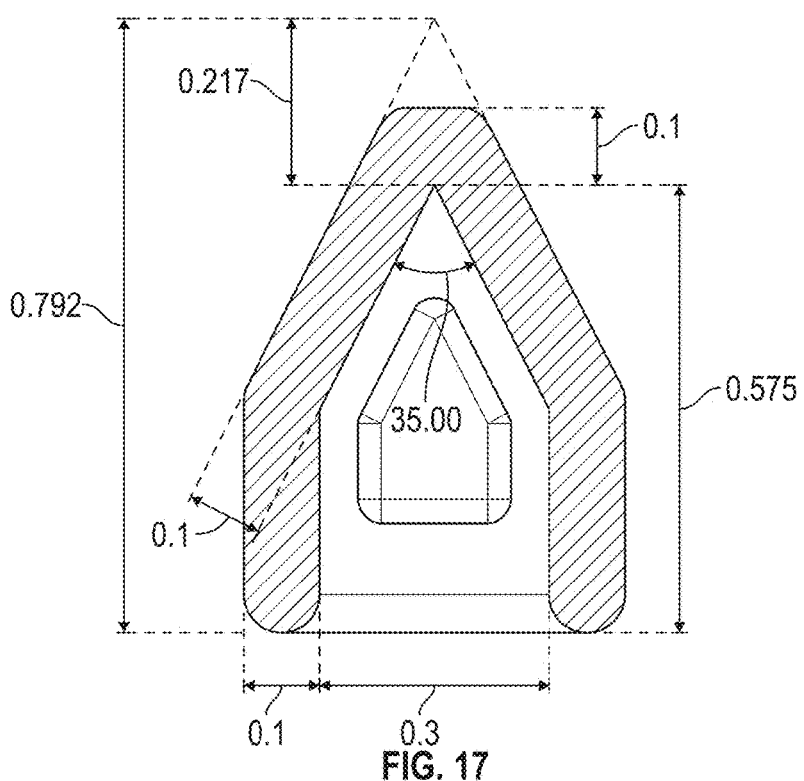
FIG. 17 is a CAD drawing of an exemplary individual microneedle.
Figure 18:
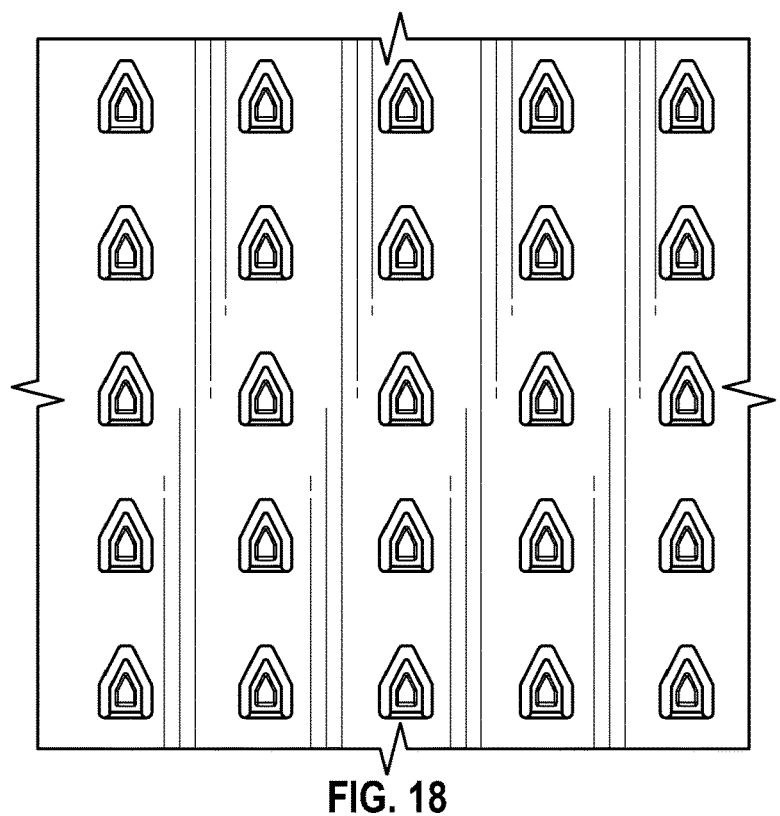
FIG. 18 is an illustration of an exemplary 1 cm² microneedle array loaded with 5 nL 1% Congo Red/well.

Example 8—In Vivo Production of Anti-EGFP Antibodies in Mice Treated with a Replicon-RNA Coated Microneedle Device Microneedle arrays were made from stainless steel foil (SS304, 75 um thick). The microneedle arrays contained 25 microneedles in a 5×5 grid pattern in a 1 cm². Needles and the array are illustrated in FIGS. 17 and 18 respectively. Microneedles were manufactured by photolithography by Kemac, Azusa, Calif. Wells and hinge were half-etch 37 μm deep.

G5 and G9 NH$_2$ PAMAM dendrimers were from Dendritech (Midland, Mich.). EGFP-replicon dendriplexes as described in Examples 1 and 2 were formed at an N/P ratio of 20 (N from the dendrimer, P from the mRNA). Reactions were carried out at 100 μL as per table below at room temperature (RT) for 30 minutes. In brief, dendrimers were diluted in nuclease-free water and Hepes buffer (final concentration 10 mM; pH 7.4) and replicon RNA was added. After 30 minutes, samples were placed in the BioDot AD 1520 printer loading tray and 5×5 welled microneedle arrays were printed 8 times with 5 nL/well (0.6 μg of mRNA/array). The printing solution was mixed by gentle pipetting between arrays.

TABLE 2

Replicon Dendrimer Reaction

| Treatment | Den | N/P Ratio | μg mRNA | Final Vol (μL) | Replicon RNA μL | Den | 100 mM HEPES | ddH$_2$O |
|---|---|---|---|---|---|---|---|---|
| G5 | G5 | 20.00 | 60.00 | 100 | 60.0 | 10.1 | 10.0 | 19.9 |
| G9 | G9 | 20.00 | 60.00 | 100 | 60.0 | 8.3 | 10.0 | 21.7 |

Figure 19:
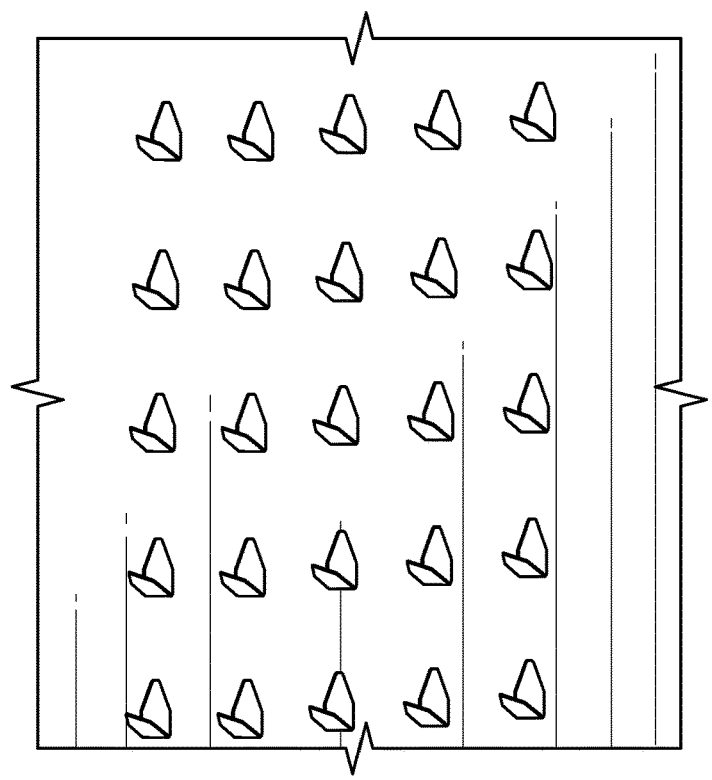
FIG. 19 is an illustration of loaded microneedles in the Z plane.

Immediately after each array was printed, needles were bent to a 90° angle by hand using a probe and jig. Thus, the needles are now in the Z plane at right angles to the SS foil sheet (FIG. 19). The completed microneedle arrays containing replicon RNA with needles in the Z plane were placed on 2.5 cm diameter adhesive bandage (Curad) without pads, sealed in foil bags, and stored on dry ice until applied to mice at the UC Davis Mouse Biology Program (MBP).

Figure 20:
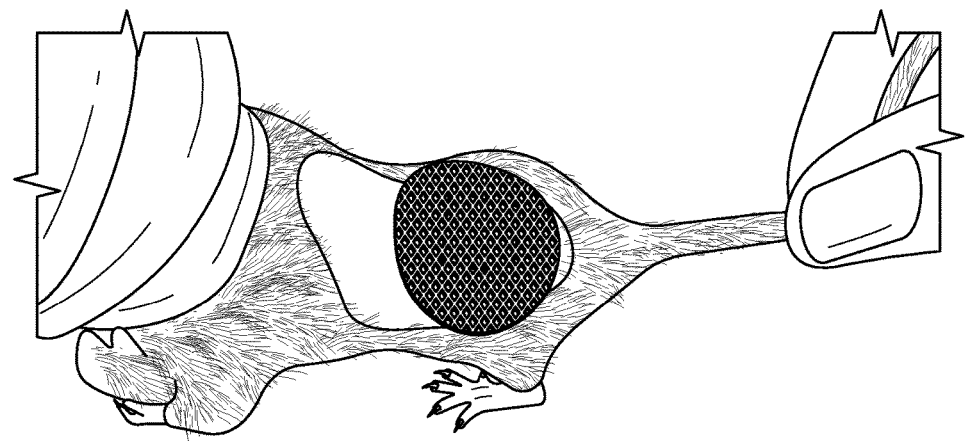
FIG. 20 is an illustration of a microneedle array patch applied to the dorsal skin of a mouse.

6-8 week old female Balb/c mice were acquired from The Jackson Laboratory. After one week of habituation to the vivarium, mice were lightly anesthetized with isoflurane and hair removed over an area of the dorsal skin for patch application (lumbosacral and upper hind limb region) a minimum of 24 hours prior to the study. Hair removal consisted of removing thicker hair with electronic clippers followed by application of a depilatory cream (Nair Sensitive Hair Remover Cream). The depilatory cream was applied to the skin using a cotton swab and left to set for 10-15 seconds before being wiped away with gauze. Nair was not left on for longer than 15 seconds as it may cause serious chemical burns. If additional applications were necessary, Nair was applied only to the haired area and removed after 5-10 seconds. After application of Nair, the entire skin area was washed with saline to ensure that no residue remained on the skin to prevent irritation. Following hair removal and recovery, array patches were applied and gently pressed on to the hairless area for 20 minutes (FIG. 20). The animals were then single housed in duplex cages during the time of patch exposure and watched carefully to prevent the animal from removing the patch. All animals were then returned to group housing once the patch was removed.

Blood was collected from the lateral saphenous vein and sera were isolated and stored at −80° C. at 7, 14, and 21 days after application of the patch. Blood was collected from alternate hind limbs each week to allow sufficient healing and to maintain vessel integrity. At 28 days after patch application, mice were euthanized, blood was collected transcardially, and sera was isolated and stored at −80° C.

Screen for EGFP-Antibodies

Mouse sera from the day 28 blood draw were tested for EGFP-antibodies. An ELISA plate was coated with EGFP protein (2 μg/ml) in carbonate buffer overnight at 4° C. The plate was washed 3× with TBST (20 mM Tris-HCl pH 7.5, 500 mM NaCl, 0.05% Tween 20) and blocked with 5% BSA (bovine serum albumin) in TBS for 1 hour at room temperature. After washing, mouse sera (1:100-1:12500) and positive control (1:500-1:12,500; anti-GFP-antibody, Cell Signaling) in 1% BSA/TBST were added and incubated for 2 hours at room temperature, followed by washing. Next, anti-rabbit secondary antibody (for control) or anti-mouse secondary antibody (for sera) at 1:5000 in 1% BSA/TBST was added for 1 hour at room temperature. The plate was washed again and then incubated with anti-SA (1:200) in 1% BSAJTBST for 20 minutes at room temperature. After washing, substrate was added and incubated for 30 minutes at room temperature. The reaction was stopped by addition of 50 ul 2N sulfuric acid.

Figure 22:
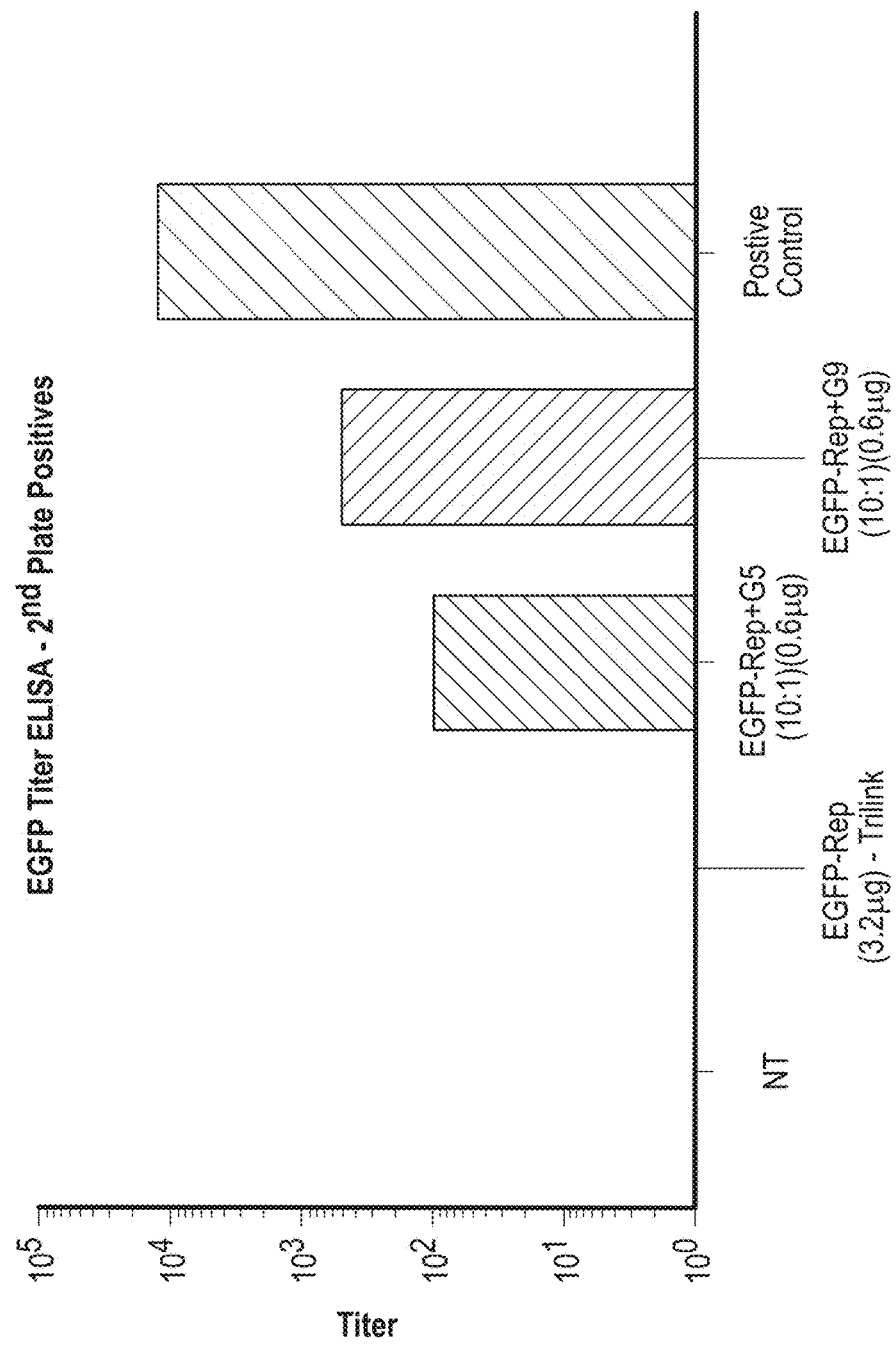
FIG. 22 exemplifies the production and titer of EGFP antibodies obtained from the 28-day sera of mice treated with an EGFP-replicon RNA coated microneedle array patch.

A minor color reaction was visible at the 1:100 dilution of mouse antisera in most samples (including sera from untreated animals) and can be considered background binding from serum contents. Mouse #36 (EGFP-Rep/G5 dendrimer; N:P 20:1) showed a color reaction more than double the background and mouse #39 (EGFP-Rep/G9 dendrimer; N:P 20:1) showed a color reaction four-fold over background. Thus the titer of EGFP antibodies by ELISA of mouse 36 was 1:200 and that of mouse 39 was 1:400 as shown in FIG. 22. EGFP-replicon RNA without dendrimers ("EGFP-Rep (3.2 ug)—Trilink") resulted in no titer as shown in FIG. 22. The positive control was a commercial anti-EGFP antibody (FIG. 22).

Example 9—In Vivo Production of Anti-Influenza HA Antibodies in Mice Treated with a Replicon-RNA Coated Microneedle Device Microneedle arrays are manufactured as described in Example 8. Influenza HA-replicon RNA is prepared as described in Examples 1 and 2. G5 and G9 $NH_2$ PAMAM dendrimers are from Dendritech (Midland, Mich.). HA-replicon dendriplexes are formed at a N/P ratio of 20 (N from the dendrimer, P from the RNA), as described in Example 8. HA-replicon RNA is then printed onto 5×5 welled microneedle arrays using a BioDot AD 1520 printer as described in Example 8. The completed microneedle arrays containing replicon RNA is placed on 2.5 cm diameter adhesive bandage without pads, sealed in foil bags, and stored on dry ice until applied to mice.

The dorsal skin hair is removed from 6-8 week old female Balb/c mice as described in Example 8, and microneedle patches are applied to the hairless area for 20 minutes. As a positive control, mice will be vaccinated using a commercially available influenza vaccine (Flulaval® QIV 1λ 5 ML MDV 2016-2017 Season—GlaxoSmithKline). Blood is collected from the lateral saphenous vein and sera were isolated and stored at −80° C. at 7, 14, and 21 days after patch application of the patch. At 28 days after patch application, mice are euthanized, blood is collected transcardially, and sera is isolated and stored at −80° C. The presence of anti-HA antibodies in the sera of microneedle and control HA mice is measured by ELISA as described in Example 8.

Example 10—Generating and Administering a Quadrivalent Alphavirus Replicon Vaccine for Influenza Virus A vaccine designed to immunize a human subject against influenza virus is described. Briefly, a plurality of alphavirus replicons are produced, each expressing a different hemagglutinin (HA); HAs derived from: an influenza A virus H1N1 strain, an influenza A virus H3N2 strain, and two separate influenza B virus lineages. The strains used will depend upon the predicted dominant influenza virus strains for that given season. HA replicon RNA sequences are generated as described in Examples 1 and 2. Optionally, replicons are formulated with G5 or G9 NH$_2$ PAMAM dendrimer nanoparticles using a microfluidic mixing device as described in Examples 5 and 6. If G5 or G9 NH$_2$ PAMAM dendrimers are utilized, they are optionally modified by fluorination.

Replicons are then packaged onto the microneedle array using a microfluidic dispensing device (e.g., BioDot). Optionally, replicons or replicon-dendrimer nanoparticles are packaged (e.g., embedded) into a microneedle array. If replicons are packaged into a microneedle array, a polymer is chosen such that it is dissolvable upon contact with the interstitial fluid of the dermis. The replicon is mixed with the polymer prior to polymerization. The polymer mixture is poured into a mold and polymerized.

The microneedle is then packaged and shipped to a medical facility at room temperature. The vaccine is applied to an individual. The microneedle is applied to the dermal surface of the individual's arm such that the microneedle pierces the dermal surface of the skin. The microneedle is applied for five minutes. If replicons are packaged into a dissolvable microneedle array, the polymer mixture containing the replicon is dissolved within the five minutes, such that the replicon is delivered to the immune cells of the skin.

Example 11—Generating and Administering an Oral Influenza Vaccine

An oral vaccine designed to immunize a human subject against influenza virus is described. Briefly, a plurality of alphavirus replicons are produced, each expressing a different hemagglutinin (HA); HAs derived from: an influenza A virus H1N1 strain, an influenza A virus H3N2 strain, and two separate influenza B virus lineages. The strains used will depend upon the predicted dominant influenza virus strains for that given season. HA replicon RNA sequences are generated as described in Examples 1 and 2. Each HA replicon is then encapsulated in liposomes and lyophilized. Alternatively, the HA replicon could be encapsulated in SNALPs. The lyophilized and encapsulated replicon is packaged into an enteric-coated capsule for oral administration. The vaccine is administered to a subject such that the replicon is delivered to the small intestine.

Example 12—A Heterologous Prime-Boost Regimen for Influenza Vaccination

A dosing regimen for vaccinating a human subject with an influenza virus vaccine is described. Briefly, a capsule comprising an alphavirus replicon encoding hemagglutinin (HA) derived from influenza A virus strain H1N1 is administered orally to a human subject to prime the subject's immune system. Two weeks later, the alphavirus replicon encoding the HA is re-administered intradermally to the subject with a microneedle, thereby selectively boosting the subject's immune response.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A microneedle device for administering a recombinant alphavirus replicon, comprising:
   (a) a dehydrated composition comprising the recombinant alphavirus replicon encoding an exogenous polypeptide; and
   (b) a substrate comprising a sheet and a plurality of microneedles extending therefrom, each of said microneedles comprising a tip, a base, a hinge at the base connecting the microneedle to the sheet, and a well comprising the dehydrated composition.

2. The microneedle device of claim 1, wherein the exogenous polypeptide is an antigen associated with an infectious agent.

3. The microneedle device of claim 1, wherein the recombinant alphavirus replicon is present in an amount effective to induce an immune response in an individual in need thereof to the exogenous polypeptide following expression of the exogenous polypeptide by the recombinant alphavirus replicon.

4. The microneedle device of claim 1, wherein the exogenous polypeptide is an influenza virus HA or NA polypeptide.

5. The microneedle device of claim 4, wherein the influenza virus HA polypeptide is an influenza A virus HA polypeptide or an influenza B virus HA polypeptide.

6. The microneedle device of claim 5, wherein the influenza virus HA polypeptide is from a viral strain of a group 1 influenza A virus subtype selected from H1, H2, H5, H6, H8, H9, H11, H12, H13, H16, H17, or H18.

7. The microneedle device of claim 5, wherein the influenza virus HA polypeptide is from a viral strain of a group 2 influenza A virus subtype selected from H3, H4, H7, H10, H14, or H15.

8. The microneedle device of claim 5, wherein the influenza virus HA polypeptide is from a viral strain of an influenza B virus.

9. The microneedle device of claim 6, wherein the influenza virus HA polypeptide is from a viral strain of an influenza A virus H1 subtype.

10. The microneedle device of claim 7, wherein the influenza virus HA polypeptide is from a viral strain of an influenza A virus H3 subtype.

11. The microneedle device of claim 8, wherein the influenza virus HA polypeptide is from a viral strain of an influenza B virus Yamagata or Victoria lineage.

12. The microneedle device of claim 1, wherein the recombinant alphavirus replicon encodes an exogenous polypeptide comprising:
   a) an HA polypeptide from a viral strain of an influenza A virus H1 subtype;
   b) an HA polypeptide from a viral strain of an influenza A virus H3 subtype;
   c) an HA polypeptide from a viral strain of an influenza B virus Yamagata lineage;
   d) an HA polypeptide from a viral strain of an influenza B virus Victoria lineage; or
   e) any combinations thereof.

13. The microneedle device of claim 12, wherein the recombinant alphavirus replicon encodes at least two exogenous polypeptides comprising:
   a) an HA polypeptide from a viral strain of an influenza A virus H1 subtype;
   b) an HA polypeptide from a viral strain of an influenza A virus H3 subtype;
   c) an HA polypeptide from a viral strain of an influenza B virus Yamagata lineage; or
   d) an HA polypeptide from a viral strain of an influenza B virus Victoria lineage.

14. The microneedle device of claim 13, wherein each of the exogenous polypeptides are encoded on a single recombinant alphavirus replicon.

15. The microneedle device of claim 13, wherein the exogenous polypeptides are encoded on different recombinant alphavirus replicons.

16. The microneedle device of claim 1, wherein the exogenous polypeptide is a hepatitis B virus surface antigen (HBsAg).

17. The microneedle device of claim 1, wherein the recombinant alphavirus replicon is formulated as a dendrimer-replicon nanoparticle.

18. The microneedle device of claim 17, wherein the dendrimer is a PAMAM dendrimer.

19. The microneedle device of claim 18, wherein the PAMAM dendrimer comprises amino surface reactive groups.

20. The microneedle device of claim 19, wherein the PAMAM dendrimer is a G5 or G9 PAMAM dendrimer comprising amino surface reactive groups.

21. The microneedle device of claim 19, wherein the PAMAM dendrimer comprises modified amino surface reactive groups.

22. The microneedle device of claim 17, wherein the dendrimer-replicon nanoparticle is formulated by a microfluidic mixing device.

23. The microneedle device of claim 17, wherein the composition further comprises a pharmaceutically acceptable excipient.

24. The microneedle device of claim 1, wherein the tip is bent about 90 degrees from the sheet about the hinge.

25. The microneedle device of claim 1, wherein the dehydrated composition is loaded onto the well of each microneedle by a microfluidic dispensing device.

26. The microneedle device of claim 1, wherein each well comprises a coating comprising the dehydrated composition.

27. The microneedle device of claim 1, wherein each well comprises a printed coating comprising the dehydrated composition.

* * * * *